United States Patent
Sims, Jr. et al.

(10) Patent No.: US 12,251,502 B2
(45) Date of Patent: Mar. 18, 2025

(54) ULTRAVIOLET LIGHT RADIATION DISINFECTION FIXTURE

(71) Applicants: Dewey McKinley Sims, Jr., Royal Oak, MI (US); Dewey McKinley Sims, III, Berkely, MI (US)

(72) Inventors: Dewey McKinley Sims, Jr., Royal Oak, MI (US); Dewey McKinley Sims, III, Berkely, MI (US)

( * ) Notice: Subject to any disclaimer, the term of this patent is extended or adjusted under 35 U.S.C. 154(b) by 368 days.

(21) Appl. No.: 17/711,636

(22) Filed: Apr. 1, 2022

(65) Prior Publication Data

US 2023/0310687 A1    Oct. 5, 2023

(51) Int. Cl.
*A61L 9/20*    (2006.01)
*F24F 8/22*    (2021.01)

(52) U.S. Cl.
CPC .............. *A61L 9/20* (2013.01); *F24F 8/22* (2021.01); *A61L 2209/134* (2013.01); *A61L 2209/16* (2013.01)

(58) Field of Classification Search
CPC ........ F24F 8/22; A61L 9/20; A61L 2209/134; A61L 2209/16; A61L 2202/12
See application file for complete search history.

(56) References Cited

U.S. PATENT DOCUMENTS

| | | | |
|---|---|---|---|
| 2,418,195 A * | 4/1947 | Rolph | F21V 7/005 362/217.08 |
| 2,569,772 A * | 10/1951 | Olsen | A61L 9/20 362/217.13 |
| 4,422,824 A | 12/1983 | Eisenhardt, Jr. | |
| 4,596,935 A | 6/1986 | Lumpp | |
| 5,326,542 A * | 7/1994 | Sizer | H01J 65/044 422/291 |

(Continued)

FOREIGN PATENT DOCUMENTS

| CN | 111265706 A | * | 6/2020 | ............. A61L 2/10 |
| CN | 111282012 A | * | 6/2020 | ............. A61L 2/10 |

OTHER PUBLICATIONS

Product: VidaShield UV24; Website: https://vidashield.com; Company: Medical Illumination.

*Primary Examiner* — Kun Kai Ma
(74) *Attorney, Agent, or Firm* — Mastrogiacomo PLLC; Patrick Mastrogiacomo, Jr.

(57) ABSTRACT

An ultraviolet-C light radiation disinfection fixture is provided. The ultraviolet-C light radiation disinfection fixture comprises a tray, a top plate, at least one louver mount, at least one ultraviolet-C light radiation source to disinfect and sterilize an air flow, a sterilization field outside the ultraviolet-C light radiation disinfection fixture, a sterilization chamber within the ultraviolet-C light radiation disinfection fixture, a plurality of ultraviolet-C light radiation reflective louvers, the plurality of reflective louvers sized and positioned proximate one another, to direct ultraviolet-C light radiation from the ultraviolet-C light radiation source to create the sterilization field and the sterilization chamber to eradicate bacterial, viral or pathogen particles from the air flow and wherein the plurality reflective louvers are positioned to limit the scatter of ultraviolet-C light radiation outside the ultraviolet-C light radiation disinfection fixture to protect humans and animals present in an enclosure while the ultraviolet-C light radiation disinfection fixture is operational.

11 Claims, 56 Drawing Sheets

(56) References Cited

U.S. PATENT DOCUMENTS

| | | | |
|---|---|---|---|
| 5,788,940 A * | 8/1998 | Cicha | B65B 55/08 |
| | | | 53/425 |
| 5,891,399 A * | 4/1999 | Owesen | A61L 9/20 |
| | | | 422/121 |
| 6,457,846 B2 * | 10/2002 | Cook | F26B 3/28 |
| | | | 356/322 |
| 6,497,840 B1 * | 12/2002 | Palestro | A61L 9/20 |
| | | | 422/4 |
| 6,656,424 B1 | 12/2003 | Deal | |
| 6,805,733 B2 | 10/2004 | Engel et al. | |
| 7,922,351 B2 | 4/2011 | Welker | |
| 8,080,203 B2 | 12/2011 | First et al. | |
| 8,162,504 B2 * | 4/2012 | Zhang | F21V 7/0091 |
| | | | 362/217.05 |
| 8,350,228 B2 | 1/2013 | Welker | |
| 8,439,517 B2 | 5/2013 | Welker | |
| 8,921,813 B2 * | 12/2014 | Palmer | H01J 61/025 |
| | | | 250/504 R |
| 9,358,313 B2 | 6/2016 | Deal | |
| 10,603,394 B2 | 3/2020 | Farren et al. | |
| 10,753,626 B2 | 8/2020 | Skelton | |
| 11,154,634 B1 * | 10/2021 | Sims, Jr. | A61L 9/20 |
| 2009/0129974 A1 | 5/2009 | McEllen | |
| 2017/0007736 A1 | 1/2017 | Engelhard | |
| 2022/0034526 A1 * | 2/2022 | Sims, Jr. | F24F 9/00 |
| 2022/0047765 A1 * | 2/2022 | D'Antonio | A61L 9/20 |

* cited by examiner

PRIOR ART

PRIOR ART

PRIOR ART

PRIOR ART

PRIOR ART

ULTRAVIOLET LIGHT RADIATION DISINFECTION FIXTURE

CROSS REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON COMPACT DISC

Not Applicable

BACKGROUND OF THE INVENTION

1. Field of the Invention

The present invention relates generally to a light fixture and, more particularly, to a light fixture that incorporates an ultraviolet light radiation source and safety features that enable the use of the ultraviolet light radiation source within an enclosed area to disinfect the air by killing airborne bacteria, viruses and pathogens that are harmful to humans and animals while humans and animals are present during the operation of the ultraviolet light.

2. Background Art

A threat to the respiratory systems of humans and animals is the Severe Acute Respiratory Syndrome Coronavirus 2 (SARS-CoV-2) virus and subsequent Coronavirus Disease (COVID-19). One means of transmitting the SARS-CoV-2 virus is by exposing or passing infectious viral particles in aerosols or water droplets from one individual to other individuals within the same enclosed area. Examples or an enclosed area may be an indoor restaurant, a working manufacturing plant or a conference room in an office building. A single infected individual may transmit the infectious viral particles to other healthy individuals through breathing, talking, yelling, singing, coughing and/or sneezing within the enclosed area. The healthy individuals merely need to have their mouth, nose or eyes in the pathway of the cloud or aerosol of infectious viral particles contained in water droplets produced by the infected individual to have the infected particles enter into a healthy individual.

As stated above, the infectious viral particles may be released into the environment by a single infected individual through breathing, talking, yelling, singing, coughing and/or sneezing within the enclosed area. However, the different aspects of expelling the viral particles may be done so in drastically different amounts of the viral particles and at varying speeds of expulsion. A single sneeze releases about 30,000 droplets that may contain the infectious viral particles at about 200 miles per hour. A SARS-CoV-2 virus cloud created by the single sneeze may move about 20 inches in 0.3 seconds. After the initial virus cloud is created by the single sneeze, the cloud will move at the speed of the air flow in the room. If there is little to no air flow in the room, the virus cloud will grow in size and remain infectious for hours. Many droplets are small and may travel great distances, easily across and filling an enclosed room in a few minutes.

A single cough releases about 3,000 droplets that may contain the infectious viral particles at about 50 miles per hour. A SARS-CoV-2 virus cloud created by the single cough may move about 20 inches in 0.3 seconds. After the initial virus cloud is created by the single cough, the cloud will move at the speed of the air flow in the room (see FIGS. 1A-1F for an illustration on how the infectious cloud of viral particles may move across a room while expanding exposing several individuals to the SARS-CoV-2 virus). If there is little to no air flow in the room, the virus cloud will grow in size and remain infectious for hours. Many droplets are large and fall quickly to the ground under the force of gravity, but many do stay in the air and may travel across an enclosed room in a few minutes.

A single breath releases 50 to 5000 droplets that may contain the infectious viral particles, but they are expelled at a very low velocity and fall to the ground quickly under the force of gravity. Unlike sneezing and coughing which release a large amount of viral material due to the exhalation force of a sneeze or cough, breathing droplets will contain less of the viral material due to a lower exhalation force. Talking increases the release of droplets about ten-fold and singing even more. There is a large amount of infectious viral material that can be introduced into an enclosed area through normal human actions that can easily fill an enclosed area. Traditional building ventilation systems with typical filtering capability merely help to fill an enclosed area with the infectious viral particles faster and may increase the chances of other individuals contracting the infection and causing the exponential spread of the SARS-CoV-2 virus.

Means have been developed to interrupt the path of the aerosol of infectious viral particles. Many stores and places of business that deal with the public on a daily basis have installed a plexiglass barrier to prevent any infectious viral particles from passing from an infected person to the individual on the other side of the plexiglass barrier. The plexiglass barrier stops the path of the infectious viral particles from reaching the individual behind the barrier. As the infectious person stands in front of the plexiglass barrier for several minutes, the individual could be creating a large cloud of infectious viral particles though breathing, talking, yelling, singing, coughing and/or sneezing within the enclosed area. As the next person in line moves forward, they will move into the cloud of infectious viral particles and increase their chances of becoming infected. The cloud of viral particles may remain infectious for several hours. If there is little to no air flow to move the cloud, the cloud of infectious viral particles may remain to infect several individuals as they move through the cloud. Further, while the plexiglass barrier stands in the path of the infectious viral particles, the viral particles have been deposited onto the surface of the plexiglass barrier. The plexiglass barrier requires a thorough cleaning with cleaners and disinfectants to adequately kill the virus. Still further, there is nothing to prevent other individuals in line from the pathway of the viral particles or touching the plexiglass surface and then their own mouth, nose or eyes and contracting the infection.

Masks and shields are other means to slow the transmission of the infectious viral particles from person to person. Masks covering the mouth and nose area are an effective means to prevent transmission of the viral particles by mouth or nose, but the mask does not cover the eyes. Shields adequately cover the eyes, nose and mouth, but may not be practical for everyday use. Further, all individuals may not be wearing masks or shields and even if they are being worn, they may not be worn correctly or people may continue to touch their eyes, mouth or nose with hands and fingers that may be infected with the infectious viral particles while adjusting the mask or shield. There have been several reports that a community choir group sang for 2.5 hours in a hall roughly the size of a volley ball court. The participants avoided the usual personal contact (handshakes, hugs, etc.) and they brought their own music to avoid sharing. The participants also social distanced themselves during practice. A single asymptomatic carrier infected 45 of the 60 choir members and two dies. Some of the participants that were infected were approximately 50 feet from the infected person.

Many are practicing social distancing by maintaining a distance of six feet from one another and limiting the number of individuals in an enclosed room. But, as described above, a single infected person may fill a room or even infect a socially distanced person with infectious viral material with a single sneeze.

Others may be shutting down their ventilation systems to limit the flow of aerosols of infectious viral particles in an enclosed room and even opening windows to allow fresh outside air into an enclosed room to dilute the cloud of infectious viral material. However, as the weather changes and heating and air conditioning is required for the comfort of the individuals in the enclosed room, ventilation system will have to be reactivated and windows closed.

Many of the above actions are being put in place in an effort to open restaurants, business and schools. However, as stated above, there are many drawbacks to these efforts to protect individuals from coming into contact with SARS-CoV-2 virus. If one examines the individual protections being proposed for schools as an example, one will quickly determine that the protections have serious drawbacks. All students and faculty will be required to wear masks or face coverings of some type as well as maintain social distancing at the requisite distance. There are several issues with this proposal. First, wearing a mask may greatly interfere with communication between the teacher and students and between the students themselves. If the communication between teacher and students is impacted negatively, both teach and students will become frustrated to a point where learning will be impacted negatively. Even worse, a teacher may remove their mask to communicate better with the students. An unmasked infected teacher may become a super spreader of the disease. An infected teacher speaking loudly for several hours may fill a classroom with many clouds of infectious viral particles in little time. Students wearing masks will still be subject to the infectious viral material contained in the room. Infectious viral particles smaller than 5 microns will pass through any mask that is not N95 certified. Even if N95 masks are required by schools, the exterior surface of the mask or any type of face covering will be contaminated with infectious viral particles. Students may touch the exterior surface when removing the mask (at the end of the day, eating lunch, etc.) or adjusting the mask with their fingers and then touch their eyes, nose or mouth thereby subjecting themselves to potential infection. Further, the cost of replacing the mask every few days is expensive and still further, there may be a shortage of masks to provide to school children and others working in a public business. Prolonged mask usage may cause hypercapnia, a condition arising from too much carbon dioxide in the blood. Symptoms of hypercapnia include dizziness, drowsiness, fatigue, headaches, felling disorientated, flushing of the skin, shortness of breath, increased heart rate and increased blood pressure (N95 masks reduce oxygen intake by approximately 5% to 20%). If one were to wear a mask long enough, it may damage the lungs. For a patient in respiratory distress, wearing a mask for a prolonged period of time may be life threatening. Students wearing face shields may alleviate the breathing issues of wearing a mask, but many of the issues discussed above, will not be improved.

Students and teachers will practice social distancing. A typical desk in a classroom is approximately two feet from a neighboring desk. This allows for a classroom to house approximately 30-35 desks depending on the size of the classroom. Social distancing dictates that there must be at least six feet between individuals. With that requirement, the number of desks and, therefore, students will be reduced to approximately 8-9 in the classroom. The other 22-26 students will have to be relocated into at least three other classrooms thereby requiring more classrooms and teachers.

Another proposal to keep students and faculty safe from the transmission of the SARS-CoV-2 virus is to add transparent plastic or plexiglass barriers between teacher and students and between students. The plastic barriers may greatly interfere with communication between the teacher and students and between the students themselves. If the communication between teacher and students is impacted negatively, both teach and students will become frustrated to a point where learning will be impacted negatively. Further, it will be difficult to move around the classroom for the teacher and the students especially if they all had to exit the classroom quickly due to an emergency. The plastic barriers would be a costly solution and the space required to position the barriers between desks within the classroom would reduce the number of desks and students in the room. As discussed above the plastic barriers may become contaminated with infectious viral particles and would require daily cleaning to remove any particles. Students and teachers may still face the possibility of infection either by existing infectious clouds of viral particles that are in the room or the viral particles present on the plastic barriers.

Still another proposal is to transform a traditional classroom into a clean room much like that of a hospital operating room. A drop ceiling may be installed in each class room with the ceiling including a plurality of high-efficiency particulate absorbing (HEPA) filters to trap the SARS-CoV-2 virus particles. Clean air may be forced downward from the ceiling driving any infectious viral particles out of the ingestion zone of students' mouth, nose and eyes and downward to the floor. The air and infectious viral particles at the floor may be forced to the walls of the clean room and sent through the gap between the walls of the clean room and the classroom back to the drop ceiling and the HEPA filters to filter out the infectious viral particles and return clean air to the room. There are several drawbacks with this proposal. The size of the clean room would still limit the number of desks and therefore students in the room. Creating a clean room will be costly and HEPA filters must be changed on a regular basis which may also be quite expensive. Further, there is a risk that those changing the filters may become infected just by handling the filters and infectious viral particles. Lastly, a continual source of HEPA filters would have to be developed to accommodate all schools and business and it may take several years to outfit and construct clean rooms for all schools and businesses.

The use of ultraviolet-C light radiation is well known for its use a disinfectant. The Centers for Disease Control ("CDC") "verifies that ultraviolet-C light radiation germicidal irradiation has been employed in the disinfection of drinking water, air, titanium implants, contact lens and the healthcare environment (i.e., operating rooms, isolation rooms, and biological safety cabinets) for both destruction of airborne organisms or inactivation of microorganisms on surfaces." (from Centers for Disease Control—Infection Control https://www.cdc.gov). Ultraviolet-C light radiation can be adapted for use in commercial and residential buildings globally along with the ventilation system of the building to eradicate airborne viruses and bacteria including coronaviruses such as SARS-CoV-2 which causes COVID19. Ultraviolet-C light radiation light in the 254 nm wavelength inactivates coronaviruses by damaging their DNA and RNA genetic material. (from Centers for Disease Control https://www.cdc.gov and Food & Drug Administration https://www.fda.gov).

Several prior art references discuss the benefits of ultraviolet-C light radiation for the eradication of airborne pathogens, viruses and bacteria. U.S. Pat. No. 2,569,772 entitled "Germicidal Lamp Mounting and Reflector" issued to Olsen requires an ultraviolet-C light radiation lamp to be held in a horizontal position. Every point along the axis of the lamp emits radiation in a 360-degree plan normal to the axis of the lamp. The desired effect of the invention is to have the ultraviolet-C light radiation travel outward and away from the ultraviolet-C light radiation lamp in a horizontal plane. The invention calls for the use of parabolic reflectors to direct the ultraviolet-C light radiation into a horizontal plane for use in disinfecting a particular area. Of the 360-degree output of the lamp, about 260-degrees of the output is redirected into a horizontal plane for use in disinfecting the area. The reflectance off the reflectors is approximately 70% which, in turn, means approximately 22% of the total output of the lamp, the total ultraviolet-C light radiation, is lost or wasted due to reflectance. Further, of the 100-degrees of radiation that is not reflected off the parabolic reflectors, approximately 98% of that radiation is absorbed by the louvers and shields of the invention leading to additional wasted energy of approximately 27% which results in a total loss of unusable radiation of approximately 49%. Almost half of the ultraviolet-C light radiation is ineffective for disinfecting the area.

Another drawback of the present invention is that air will not flow through the fixture, meaning that the high intensity radiation near the source of the ultraviolet-C light radiation is not being used for disinfecting the air. Only the air flowing away from the fixture and passing through the ultraviolet-C light radiation in front of the fixture is being disinfected. As is known in the art, the intensity of the ultraviolet-C light radiation decreases by the square of the distance from the ultraviolet-C light radiation source or lamp. The distance the radiation travels from the lamp to the outer edges of the fixture is about 6 inches. Therefore, the intensity of the radiation exiting the lamp may be reduced by a factor of 36 times thereby resulting in a significant reduction in the quality of disinfection the fixture can produce.

U.S. Pat. No. 6,656,424 entitled "Ultraviolet Area Sterilizer And Method Of Area Sterilization Using Ultraviolet Radiation" issued to Deal discloses a ultraviolet-C light radiation sterilizer for use in disinfecting a room. The drawback with this particular invention is the requirement that all human and animals must be out of the room or building during the disinfection process due to the harmful ultraviolet-C light radiation to humans and animals. Furthermore, disinfection only occurs when the invention is deployed into a room. If an individual carries harmful pathogens, viruses or bacteria into a room, the room will become infected along with the potential to infect others in the room before the room can be disinfected with ultraviolet-C light radiation. U.S. Pat. No. 9,358,313 titled "Ultraviolet Radiation Emitting Fixture" also issued to Deal discloses a ultraviolet-C light radiation fixture for use in disinfecting a room. As described above in '424, the main drawback with this particular invention is the requirement that all human and animals must be out of the room or building during the disinfection process due to the harmful ultraviolet-C light radiation to humans and animals. The same issues described above with a lack of continuous ultraviolet-C light radiation eradication also apply to this invention as well.

Ultraviolet-C light radiation's germicidal effectiveness is influenced by UV intensity, which is affected by distance away from the ultraviolet-C light radiation. (from Food & Drug Administration https://www.fda.gov). U.S. Pat. No. 8,921,813 entitled "Reflector For Ultraviolet Sterilizer Fixture" issued to Palmer et al. includes an elaborate system of parabolic reflectors and baffles to reflect the ultraviolet-C light radiation laterally to protect the occupants of the room (see FIGS. 17A-17C). The execution of the present invention is similar to the execution of the Olsen invention discussed above and is saddled with similar drawbacks. Typically, these units are attached at the wall to ensure the baffles extend laterally. A number of units and, therefore, expense, are required to ensure adequate ultraviolet-C light radiation coverage to disinfect the air. Furthermore, as discussed above, the intensity of the ultraviolet-C light radiation decreases the further away from the source the ultraviolet-C light radiation must travel, thereby making it less likely the above invention would be capable of using ultraviolet-C light radiation to disinfect the center of a larger room.

Both the Palmer et al. and Olsen inventions rely on the use of parabolic reflectors to enable their respective inventions. Parabolic reflectors require very tight tolerances and the surface must be a highly polished metal such as aluminum or steel to ensure reflections which results in a very expensive component. Furthermore, the smallest error (approximately 1-degree to 2-degrees) in location of the parabolic reflectors or the location of the bulb may result in all the ultraviolet-C light radiation produced by the lamp being absorbed into the fixture prior to having the opportunity to disinfect the area.

U.S. Pat. No. 8,080,203 entitled "Air Sterilization Apparatus" issued to First et al. discloses an air sterilization apparatus that may direct air across ultraviolet-C light radiation field to sterilize the air. A baffle may also be provided to shield the eyes of occupants of the room from ultraviolet-C light radiation in the radiation field. In this particular invention, much of the ultraviolet-C light radiation from the lamp (more than 290 degrees of the 360-degree output of the ultraviolet-C light radiation lamp) is absorbed by the baffle and the base resulting in approximately 80% of the output of the ultraviolet-C light radiation lamp being lost and wasted. Also, less than 10 degrees of the lamp output shines horizontally outward to disinfect the air. Further, the air approaching the fixture will not be disinfected and the air is not forced to flow into the fixture and around the ultraviolet-C light radiation bulb where the highest intensity ultraviolet-C light radiation may be found.

United States Patent Application No. 2009/0129974 entitled "Air Quality Enhancing Ceiling Paddle Fan" issued to McEllen discloses a ceiling paddle fan fixture having a ultraviolet-C light radiation source to sterilize room air while the fixture is in use. Sterilization of room air is achieved by the passage of a high volume of air at a relatively slow speed through a relatively low intensity ultraviolet-C light radiation field. The main drawback with the McEllen disclosure is the small opening to allow air and light to pass through. The opening is between 10 degrees and 45 degrees. An opening of 10 degrees results in 350 degrees of the ultraviolet-C light radiation from the lamp being absorbed by the fixture meaning the fixture is approximately 3% effective for eradication of any virus, bacteria or pathogen from the air near the lamp. An opening of 45 degrees increases the effectiveness of the ultraviolet-C light radiation from the lamp to approximately 13%. This leads to a coverage area of approximately 50 square feet for a single fixture meaning a number of fixtures and expense will be required to sterilize the air in a large room.

U.S. Pat. No. 10,753,626 entitled "Air Treatment Unit" issued to Skelton discloses an air treatment unit having a ultraviolet-C light radiation source configured to disinfect air (see FIGS. 17D and 17E). Air from a duct or within a space is directed into a volume that has ultraviolet-C light radiation rays from the source of the ultraviolet-C light radiation therein capable of disinfecting air. The main disadvantage of this invention is the ultraviolet-C light radiation leaving the source lamp is absorbed by the surface of the ceiling, the bottom wall and the edges of the louvers. Approximately 10 degrees of the 360-degree output of the ultraviolet-C light radiation lamp will pass through the spaces between the louvers meaning this fixture is about 3% effective at eradicating viruses, bacteria and pathogens from the air around the fixture leading to the need for a large number of fixtures, and, thus expense, to adequately sterilize the air in a room.

Therefore, a need exists for an inexpensive and practical ultraviolet light radiation disinfection fixture that enables constant operation of the ultraviolet light within an enclosed area or room during the presence of humans and animals to kill and eliminate the infectious viral and bacterial particles and pathogens. A need also exists for a number of inexpensive disinfection fixtures to be deployed in the enclosed area such that the entire area may be covered with adequate ultraviolet radiation to disinfect and sterilize the air in the entire room while at the same time safely allowing the presence of humans and animals within the room during the disinfection process. Furthermore, a need exists for a highly effective ultraviolet light disinfection fixture that allows a significant portion of the ultraviolet radiation to travel outside the fixture to disinfect and sterilize a large area with a minimal number of fixtures to kill and eliminate the infectious viral and bacterial particles and pathogens.

BRIEF SUMMARY OF THE INVENTION

An ultraviolet-C light radiation disinfection fixture is provided, the ultraviolet-C light radiation disinfection fixture comprises a tray, the tray including a base plate, at least one side wall, the at least one side wall is positioned at a ten degree outward angle relative to a perpendicular vertical that extends upward from the base plate, and at least one end plate. The fixture further comprises a top plate, at least one louver mount, at least one ultraviolet-C light radiation source to disinfect and sterilize an air flow, a sterilization field outside the ultraviolet-C light radiation disinfection fixture, a sterilization chamber within the ultraviolet-C light radiation disinfection fixture, a plurality of ultraviolet-C light radiation reflective louvers, the plurality of ultraviolet-C light radiation reflective louvers sized and positioned proximate one another, to direct ultraviolet-C light radiation from the ultraviolet-C light radiation source to the exterior of the ultraviolet-C light radiation disinfection fixture to create the sterilization field outside the ultraviolet-C light radiation disinfection fixture to eradicate bacterial, viral or pathogen particles from the air flow surrounding the ultraviolet-C light radiation disinfection fixture, the plurality of ultraviolet-C light radiation reflective louvers sized and positioned proximate one another to direct ultraviolet-C light radiation from the ultraviolet-C light radiation source in the interior of the ultraviolet-C light radiation disinfection fixture to create the sterilization chamber inside the ultraviolet-C light radiation disinfection fixture and the plurality of ultraviolet-C light radiation reflective louvers sized and positioned proximate one another to allow passage of the air flow containing a cloud of infectious bacterial, viral or pathogen particles to pass through the sterilization chamber within the ultraviolet-C light radiation disinfection fixture to eradicate bacterial, viral or pathogen particles from the air flow and wherein the plurality of ultraviolet-C light radiation reflective louvers are positioned to limit the scatter of ultraviolet-C light radiation outside the ultraviolet-C light radiation disinfection fixture to protect humans and animals present in an enclosure while the ultraviolet-C light radiation disinfection fixture is operational.

BRIEF DESCRIPTION OF THE SEVERAL VIEWS OF THE DRAWINGS

The features and inventive aspects of the present invention will become more apparent from the following detailed description, claims, and drawings, of which the following is a brief description:

Figure 1A:
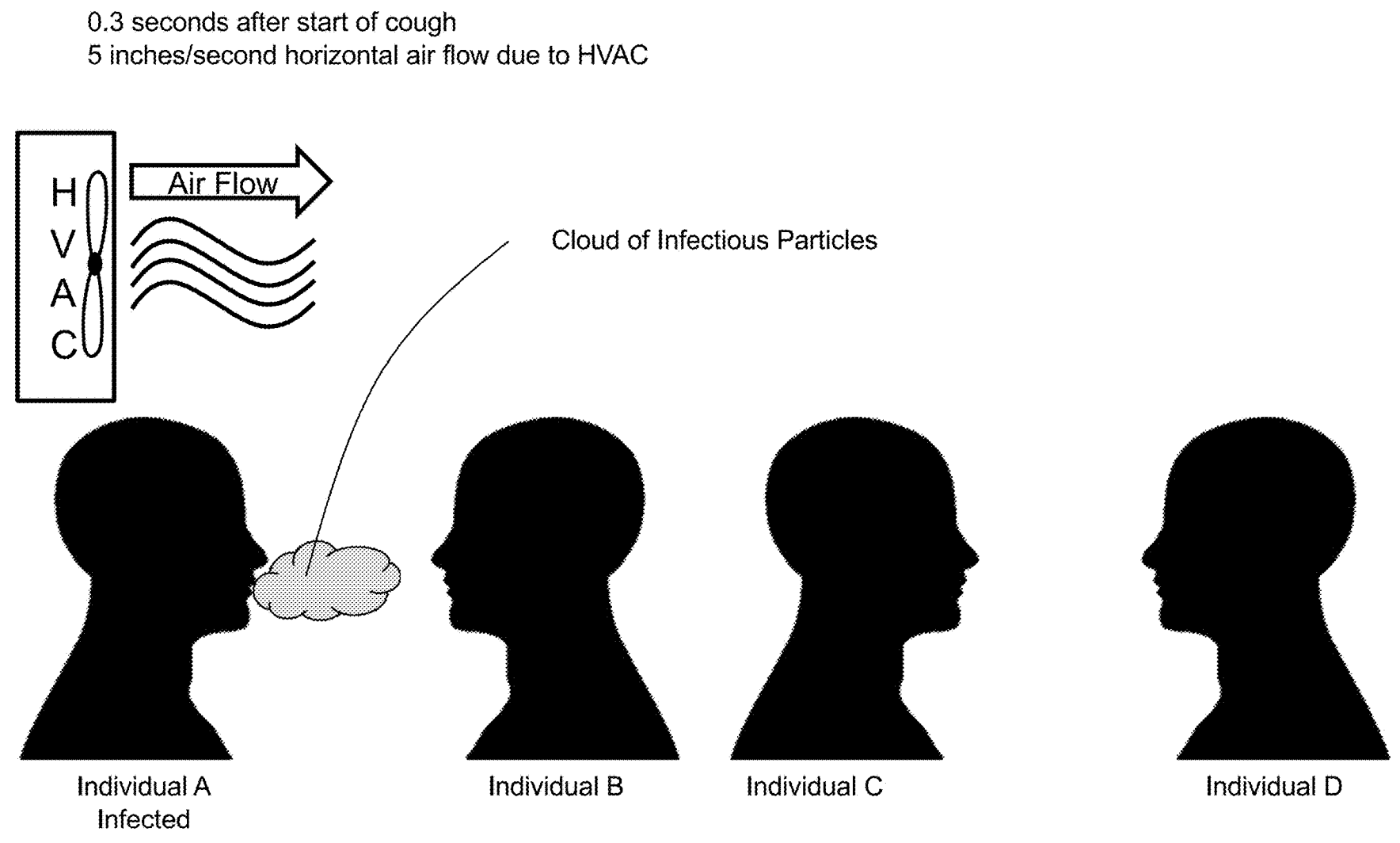

FIGS. 1A-1F are side views illustrating how a cloud of infectious viral particles may pass from an infected individual to expose subsequent individuals in a typical room under the operation of a typical heating, ventilation and air conditioning (HVAC) system with a horizontal air flow;

FIG. 16 is a table illustrating the intensity of the ultraviolet light at a particular distance from the ultraviolet light disinfection fixture of the present invention.

DETAILED DESCRIPTION OF THE INVENTION

Figure 1B:
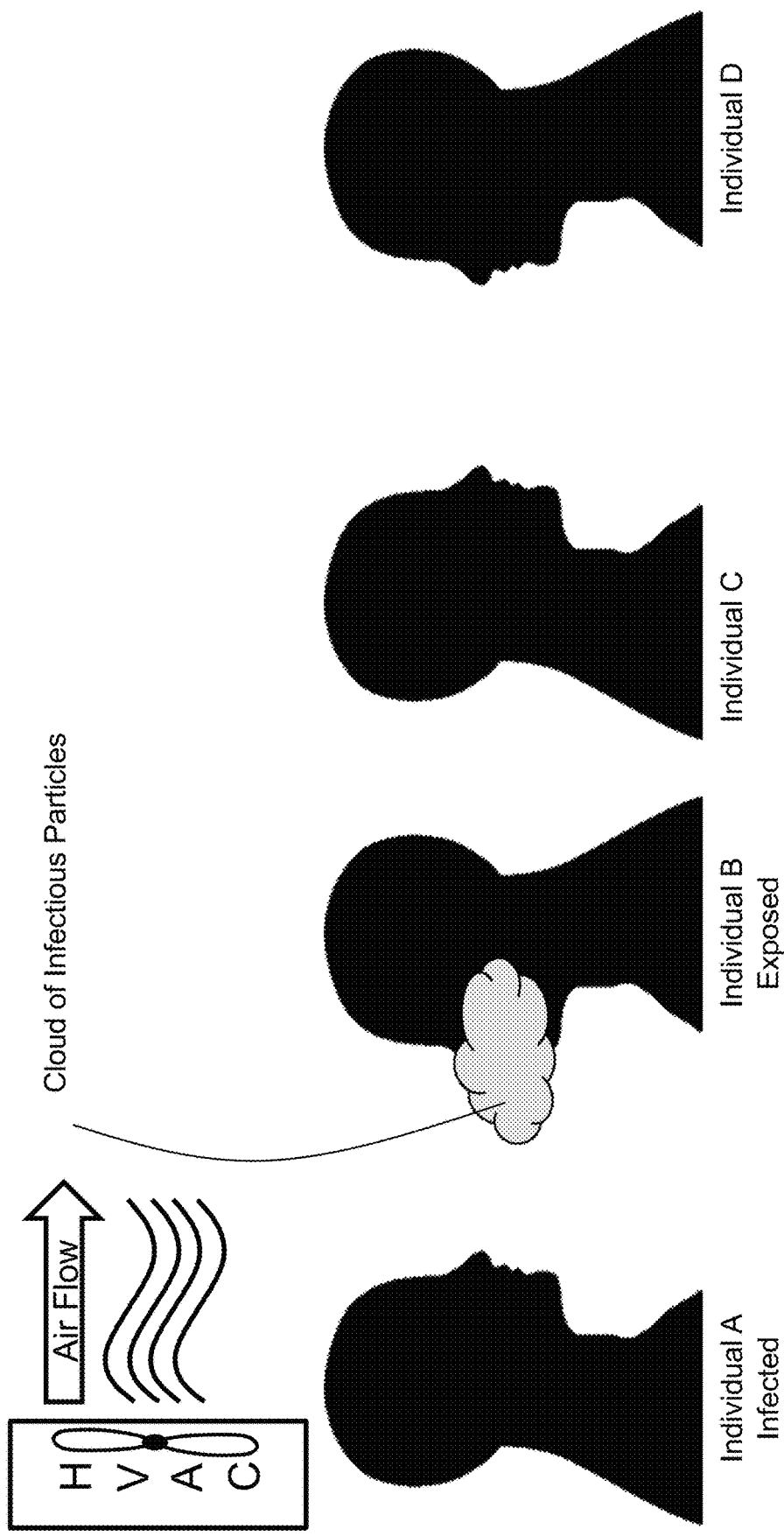
Figure 1C:
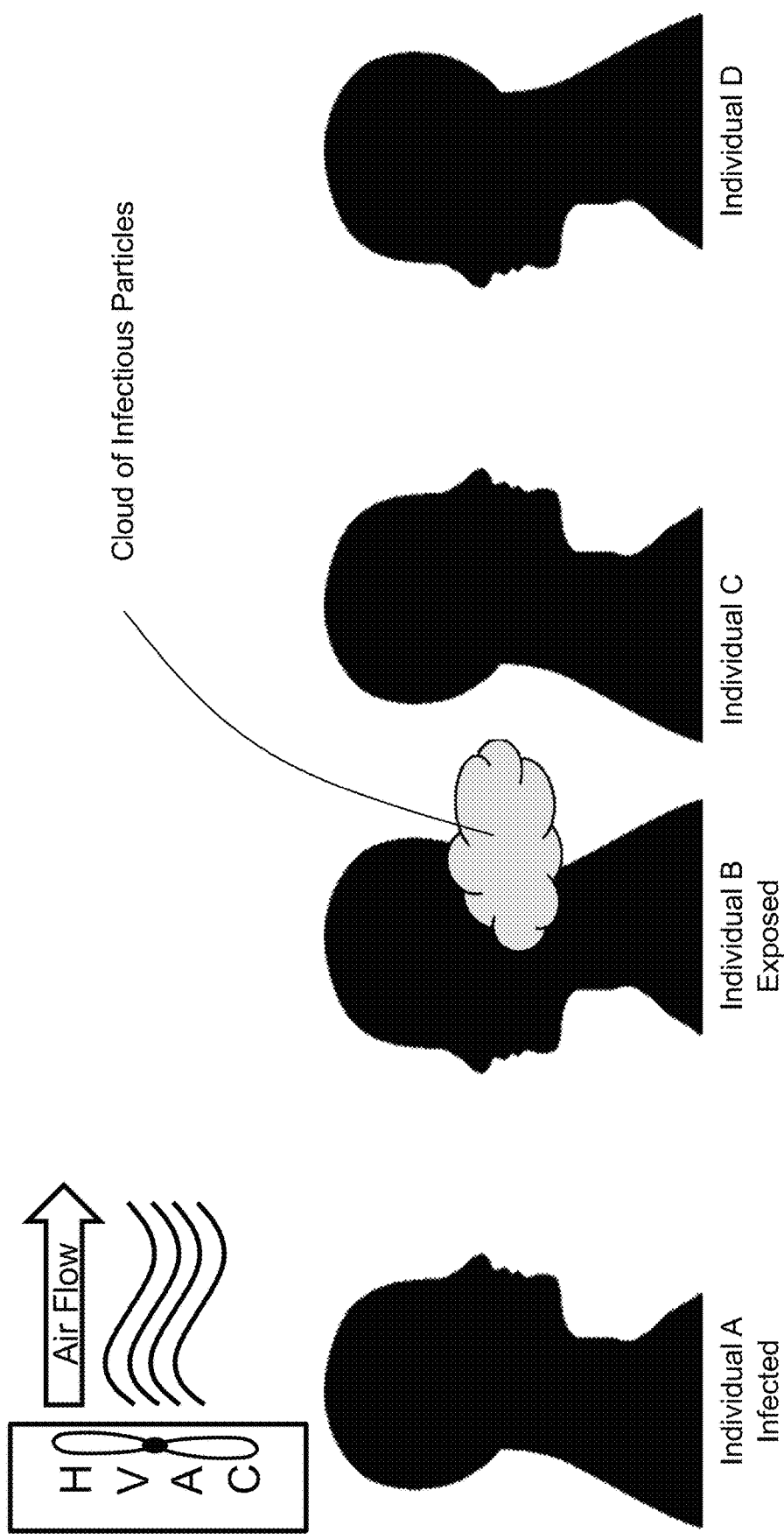
Figure 1D:
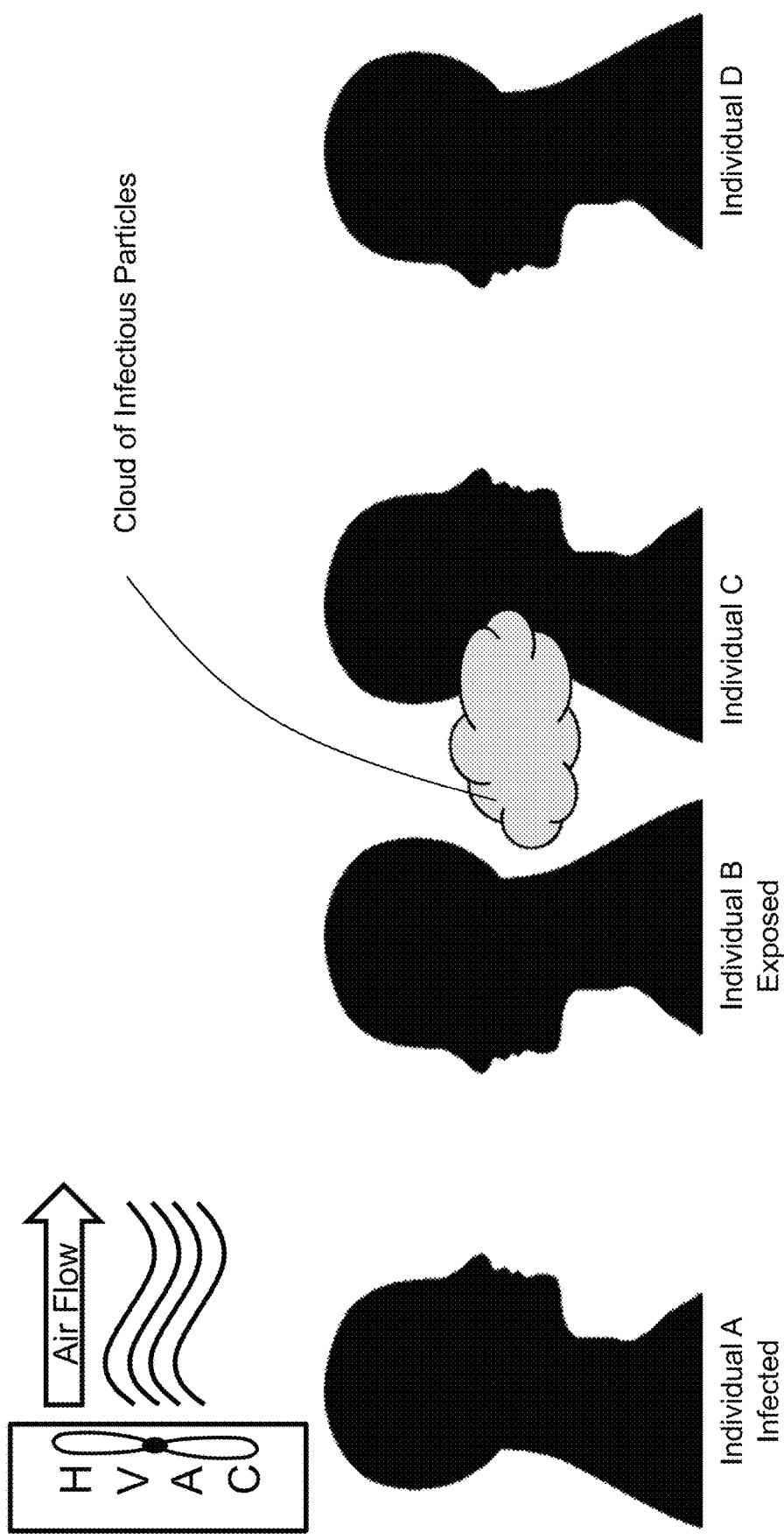
Figure 1E:
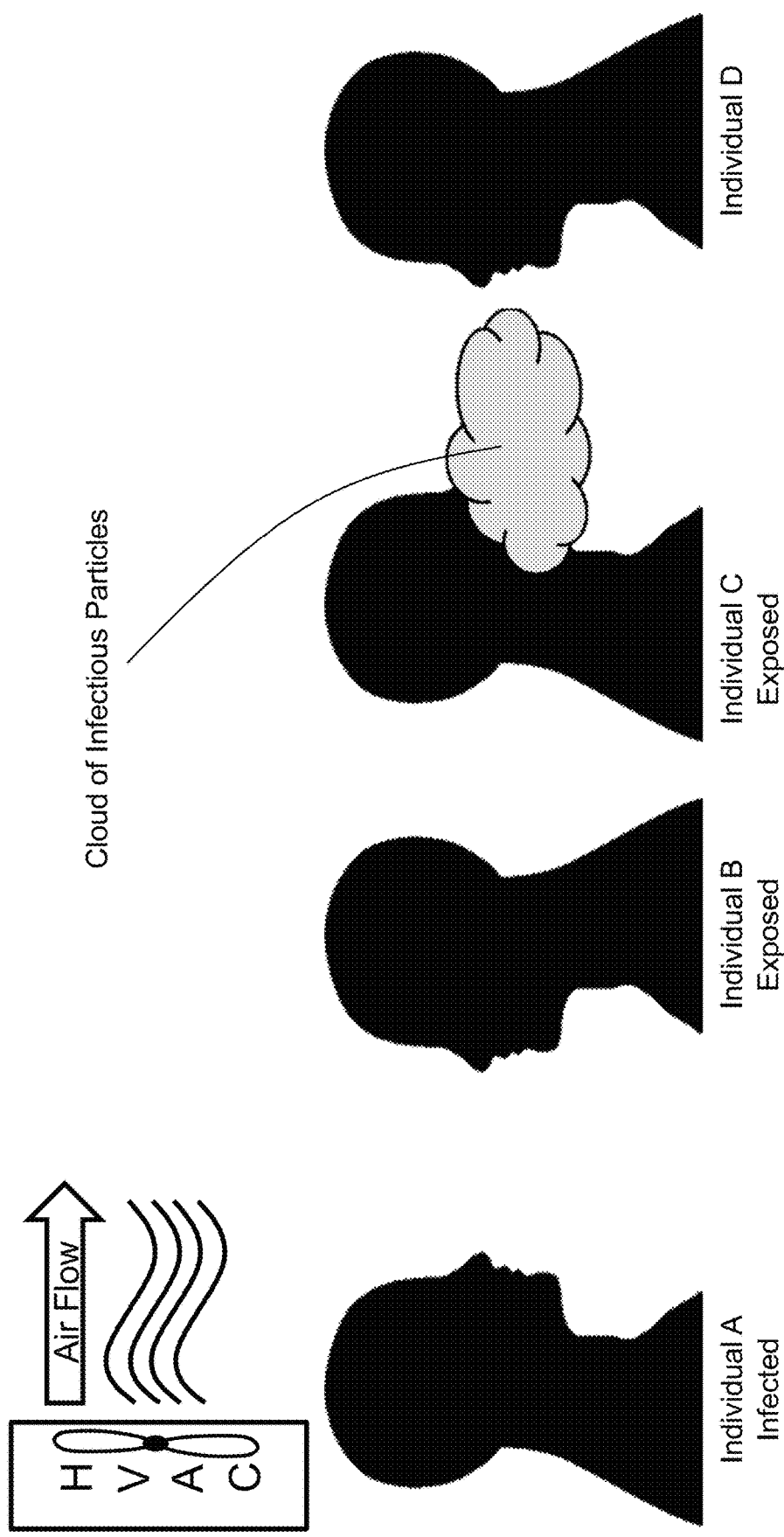
Figure 1F:
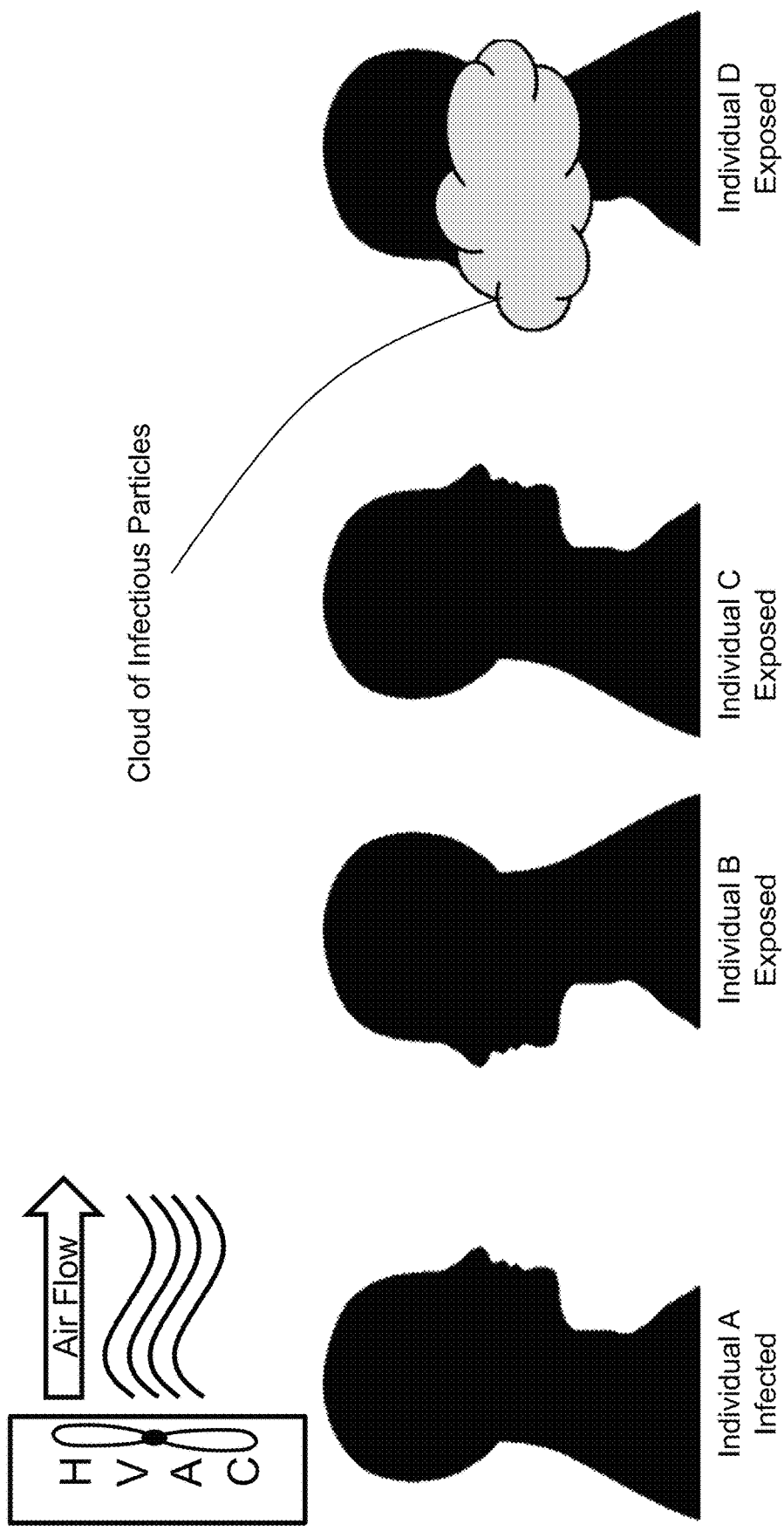
Figure 2:
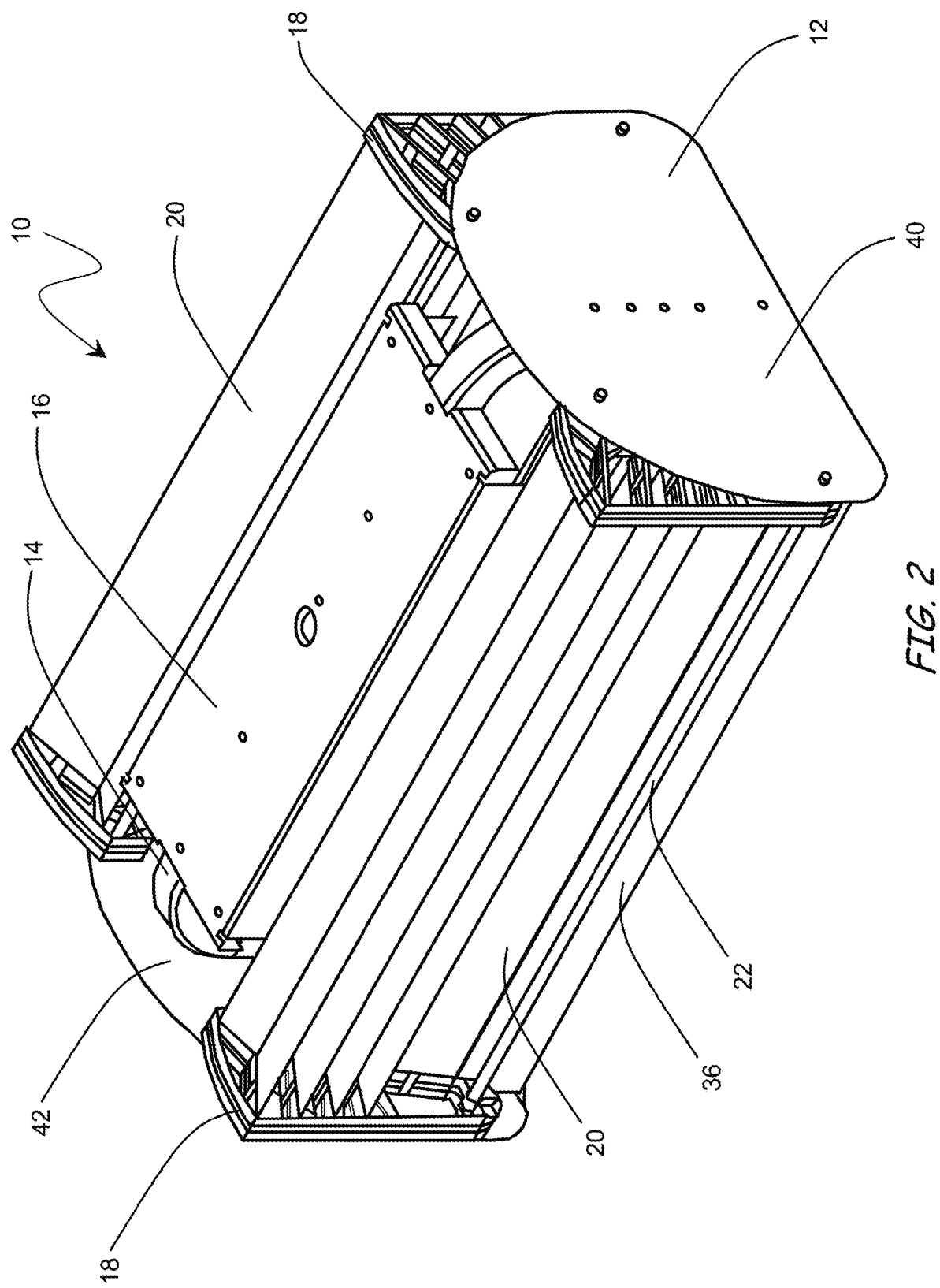
FIG. 2 is an isometric view of an ultraviolet light disinfection fixture according to an embodiment of the present invention.
Figure 3:
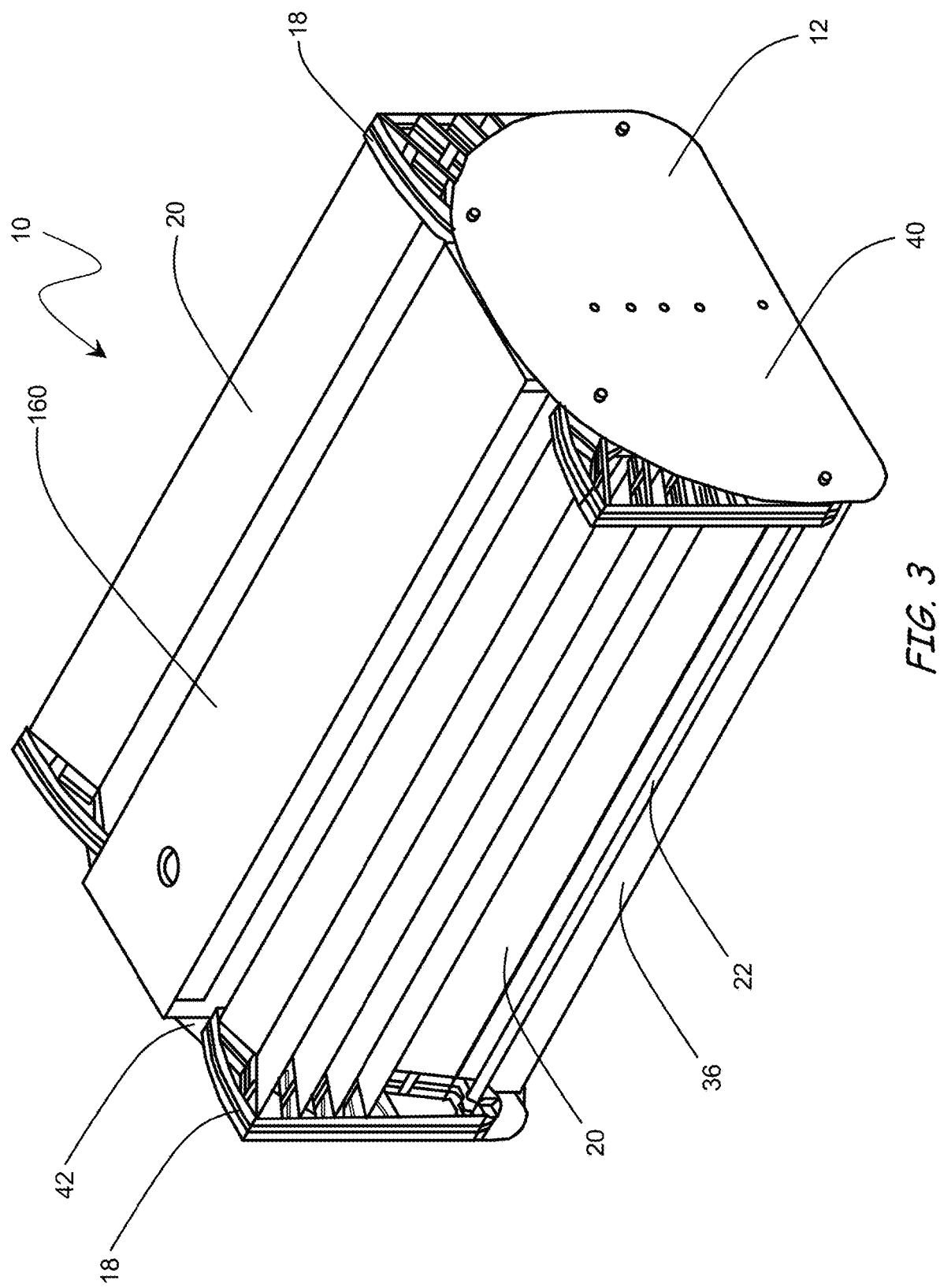
FIG. 3 is an isometric view of an ultraviolet light disinfection fixture according to another embodiment of the present invention.

Referring now to the drawings, preferred illustrative embodiments of the present invention are shown in detail. Although the drawings represent embodiments of the present invention, the drawings are not necessarily to scale and certain features may be exaggerated to better illustrate and explain the present invention. Further, the embodiments set forth herein are not intended to be exhaustive or otherwise to limit or restrict the invention to the precise forms and configurations shown in the drawings and disclosed in the following detailed description.

The wearing of masks, other face coverings and shields as well as the use of plexiglass barriers and social distancing all work to help limit the transmission of infections and viruses such as influenza and SARS-CoV-2, however, these tools will not kill and eliminate the infectious viral and bacterial particles and pathogens. The present invention provides an ultraviolet light disinfection fixture 10 that will provide ultraviolet light radiation having a wavelength of 200 nanometers-280 nanometers, also known as ultraviolet-C light radiation. When operational, ultraviolet light disinfection fixture 10 will enable an ultraviolet-C light radiation disinfection/sterilization field throughout fixture 10 and in the surrounding area to eradicate infectious viral material, bacteria and pathogens, such as a cloud of infectious influenza or SARS-CoV-2 particles and the like. Light disinfection fixture 10 will direct the ultraviolet-C light radiation in a manner such that any humans or animals present in the area during operation of an ultraviolet-C lamp will not be harmed by the ultraviolet-C light radiation.

According to an embodiment of the present invention, ultraviolet light disinfection fixture 10 includes a tray 12, a tube 14 and a top plate 16 as illustrated in FIGS. 2, 5A-7 and 9. Fixture 10 further includes a plurality of louver mounts 18, a plurality of ultraviolet-C light radiation reflective louvers 20 and a plurality of rods 22. At least one ultraviolet-C light source such as a bulb 24 or fluorescent tube 128 and socket 26 are also included in fixture 10 (see FIGS. 5B-5D and 11A-12F).

Figure 4A:
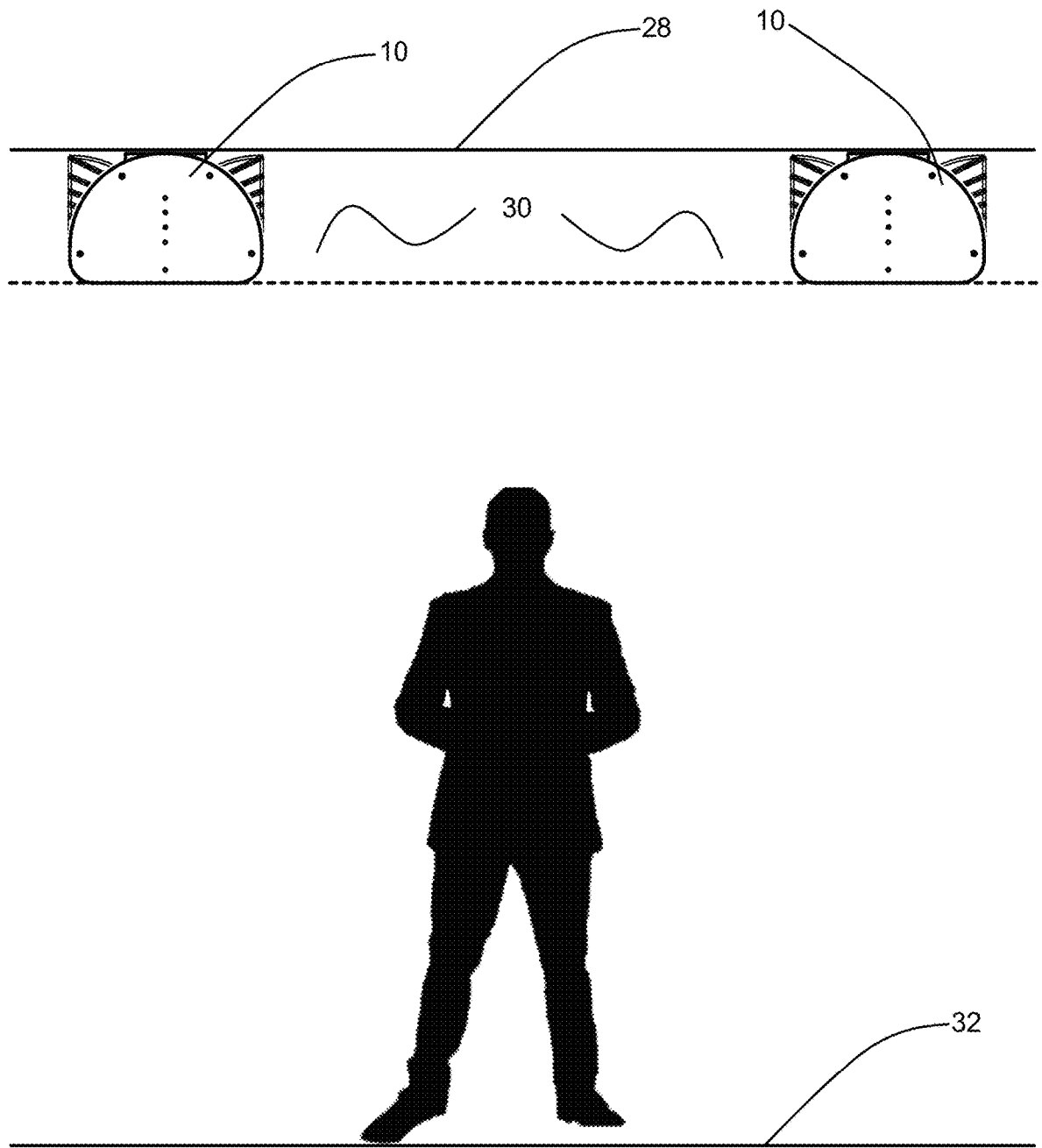
FIGS. 4A and 4B are environmental views of a number of the ultraviolet disinfection fixtures shown deployed in a typical room to achieve maximum ultraviolet-C radiation exposure to eradicate pathogens, viral particles and bacteria in the room.
Figure 4B:
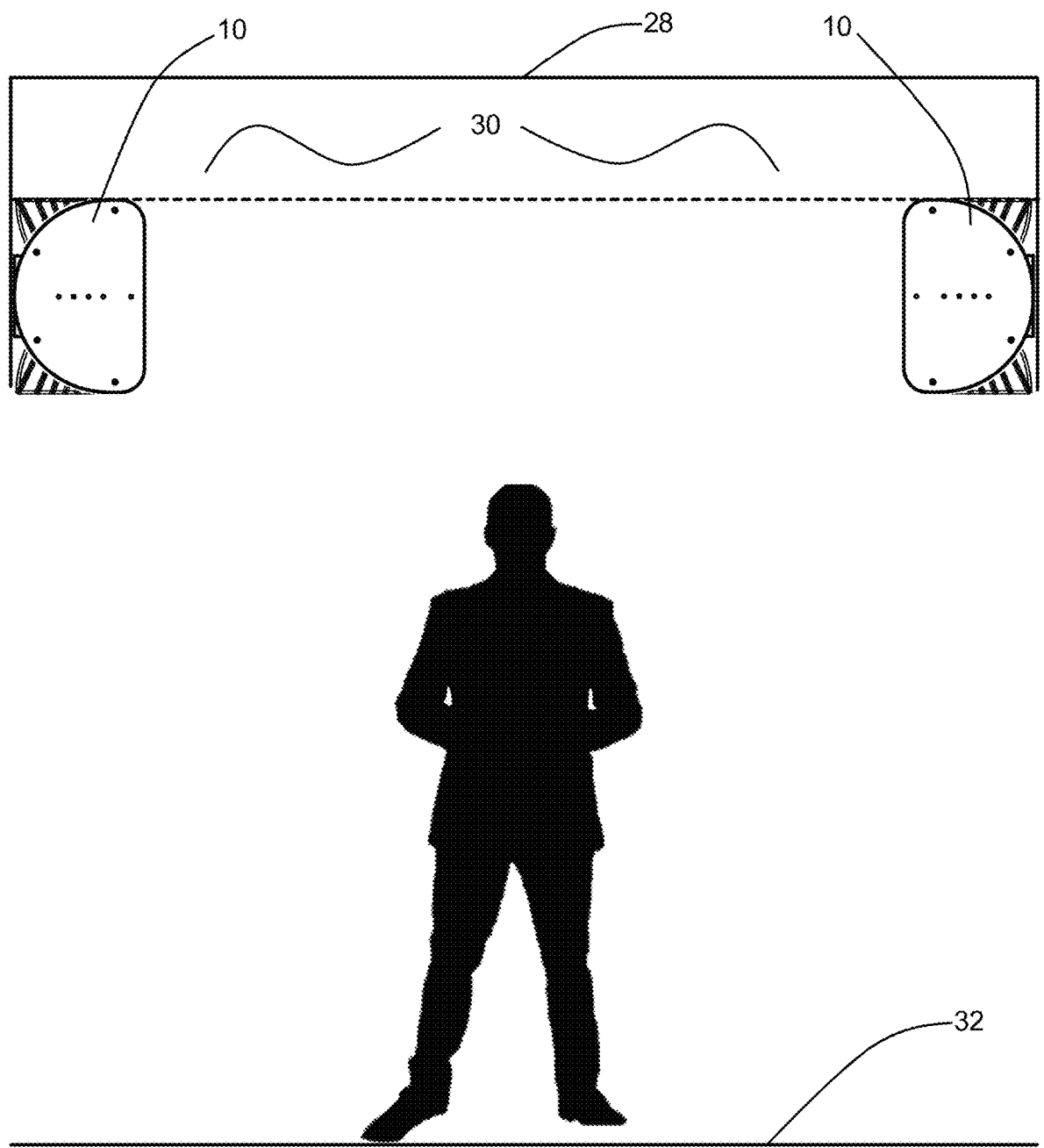

FIGS. 4A and 4B illustrate how fixture 10 along with an ultraviolet-C bulb 24, may be deployed in a typical room setting to sterilize and disinfect the air in the room. Fixture 10 may be secured to a ceiling 28 such that fixture 10 directs any ultraviolet-C light radiation from bulb 24 outward from fixture 10 to create a disinfection/sterilization field 30. Fixture 10 also directs ultraviolet-C light radiation away from any humans and animals that may be present in the room and standing on a floor 32. In this particular embodiment of the present invention, bulb 24 may be mounted horizontally within fixture 10. Fixture 10 may be configured to direct ultraviolet-C light radiation to the interior of fixture 10 and approximately 80% of ultraviolet-C light radiation outward to the exterior and generally horizontal from fixture 10 to disinfect and sterilize any air flowing within and outside of fixture 10. Fixture 10 may be mounted in areas or rooms with a ceiling height of eight feet or more to ensure ultraviolet-C light radiation is at a safe level above humans and animals and away from eyes that may be damaged by ultraviolet-C light radiation. Fixture 10 will work with the room's heating, ventilation and air conditioning (HVAC) system as well as in rooms with ceiling fans to ensure the air flowing within the room is disinfected and sterilized and any viruses, bacteria and pathogens are eradicated from the air to help maintain the health of those individuals in the room.

Now referring to FIGS. 5A-9 and 11A-12E, tray 12 is illustrated. According to an embodiment of the present invention, tray 12 may be formed from a single sheet of metal, such as aluminum, steel and the like. In this particular embodiment of the present invention, tray 12 may be manufactured from polished aluminum to provide a maximum reflectance of the ultraviolet-C light radiation. Tray 12 includes a base plate 34 that may be generally rectangular in shape. A pair of opposing side walls 36 and 38 intersect base plate 34 and extend generally upward from base plate 34. Side walls 36, 38 may be positioned at approximately a ten (10) degree outward angle relative to a perpendicular vertical that extends upward from base plate 34 (see FIGS. 14A-14J). Side wall 36 includes a wing 120 that protrudes outward from a top edge of side wall 36 and wing 120 extends a length of side wall 36. Side wall 38 includes a wing 122 that protrudes outward from a top edge of side wall 38 and wing 122 extends a length of side wall 38. Wings 120, 122 may be angled downward approximately four (4) degrees relative to base plate 34 (see FIGS. 14A-14J).

Tray 12 also includes a pair of opposing end plates 40 and 42, each of end plates 40, 42 intersect base plate 34 and extend generally upward from base plate 34. End plates 40, 42 may be generally rectangular in shape and include rounded edges. Each of side walls 36, 38 and end plates 40, 42 may be folded upward from base plate 34 to create tray 12. End plates 40, 42 intersect side walls 36, 38 to form tray 12 and end plates 40, 42 and side walls 36, 38 may be welded at the intersection to secure end plates 40, 42 to side walls 36, 38. Forming tray 12 from a single sheet of metal improves the quality of tray 12 and limits manufacturing costs. However, it is important to note that tray 12 and its side walls 36, 38 and end plates 40, 42 may be manufactured any material such as polymers, wood, and the like and be manufactured by any means including typical blow molding, stamped components, welding, gluing, fasteners and the like while still embodying the present invention. An ultraviolet-C light radiation absorption pad 44 may also be included with tray 12. Pad 44 is positioned and secure within tray on base plate 34 (see FIGS. 14A-14F and 14H-14J). Forming tray 12 in this manner will also create a disinfection/sterilization chamber 118 within tray 12 and the interior of fixture 10.

Tube 14 may be generally rectangular in cross-sectional shape and extend a length of tray 12 between end plates 40 and 42. Tube 14 may be manufactured from any material such as aluminum, steel, wood, a polymer and the like. In this particular embodiment of the present invention, tube 14 may be manufactured from polished aluminum to provide a maximum reflectance of the ultraviolet-C light radiation. The cross-sectional area of tube 14 may be sized to allow a typical three wire or four wire insulated electrical wire bundle 130 to pass through to fixture 10 from an electrical box 134 to provide electrical power to fixture 10. Tube includes legs 46 and 48 that interface with end plates 40, 42. Leg 46 includes a plurality of holes 50 to align with a plurality of holes 54 of end plate 40. Leg 48 includes a plurality of holes 52 to align with a plurality of holes 56 of end plate 42. When legs 46, 48 of tube 14 are positioned proximate end plates 40, 42 and holes 50 and 54 are aligned and holes 52 and 56 aligned, fasteners, such as a screw, bolt and nut, rivets and the like may be used to secure tube 14 to end plates 40, 42 at holes 50, 54 and holes 52, 56 and provide a rigid mounting structure for fixture 10. Although depicted as having a cross-sectional shape as generally rectangular, it is important to note that tube 14 may have any other cross-sectional shape such as circular, oval, triangular and the like and may be used to secure end plates 40, 42 and support fixture 10.

Figure 13A:
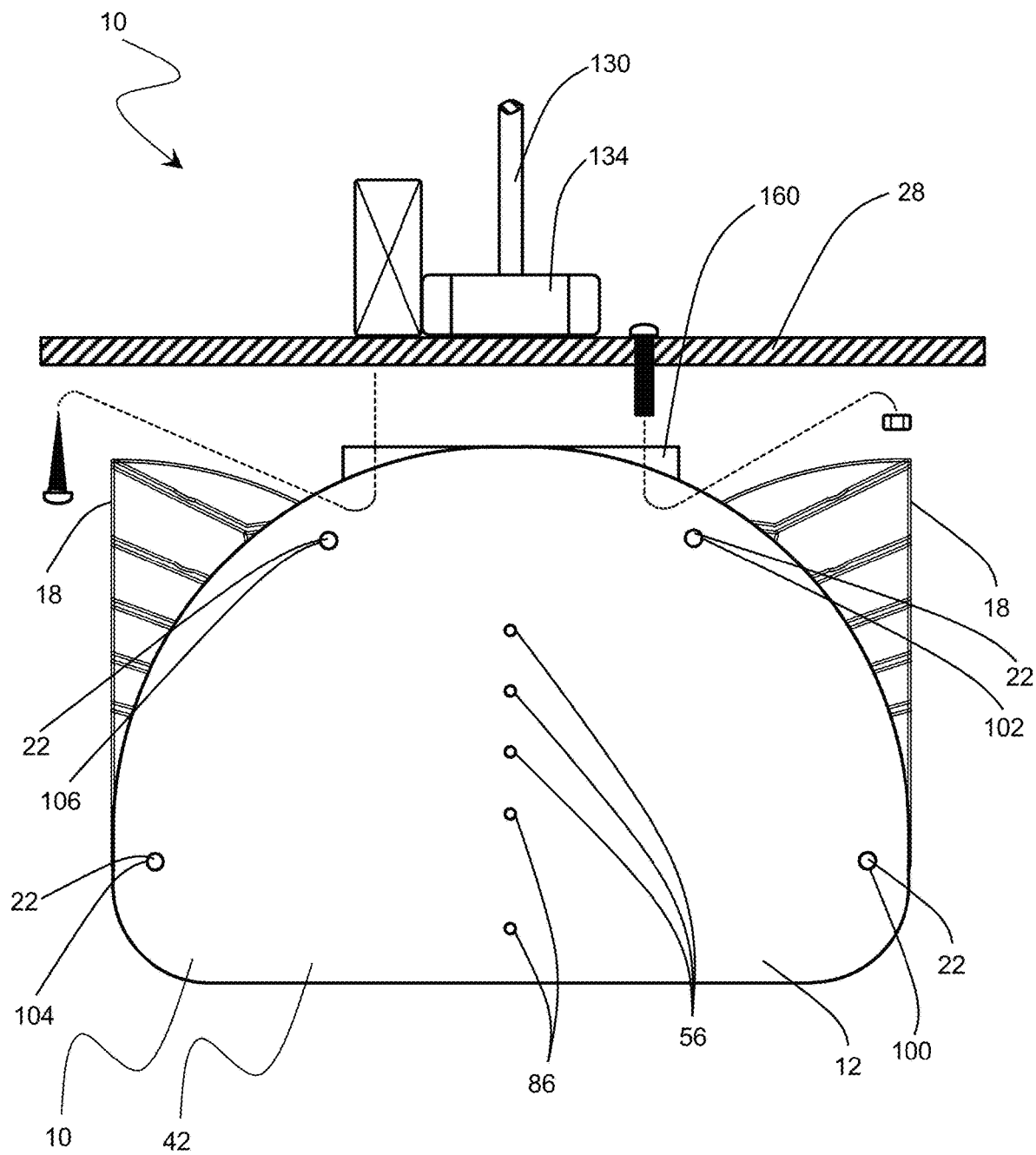
FIGS. 13A and 13B are side views of the of the ultraviolet light disinfection fixture according to the embodiment of the present invention illustrating alternative mounting means to a structure.
Figure 13B:
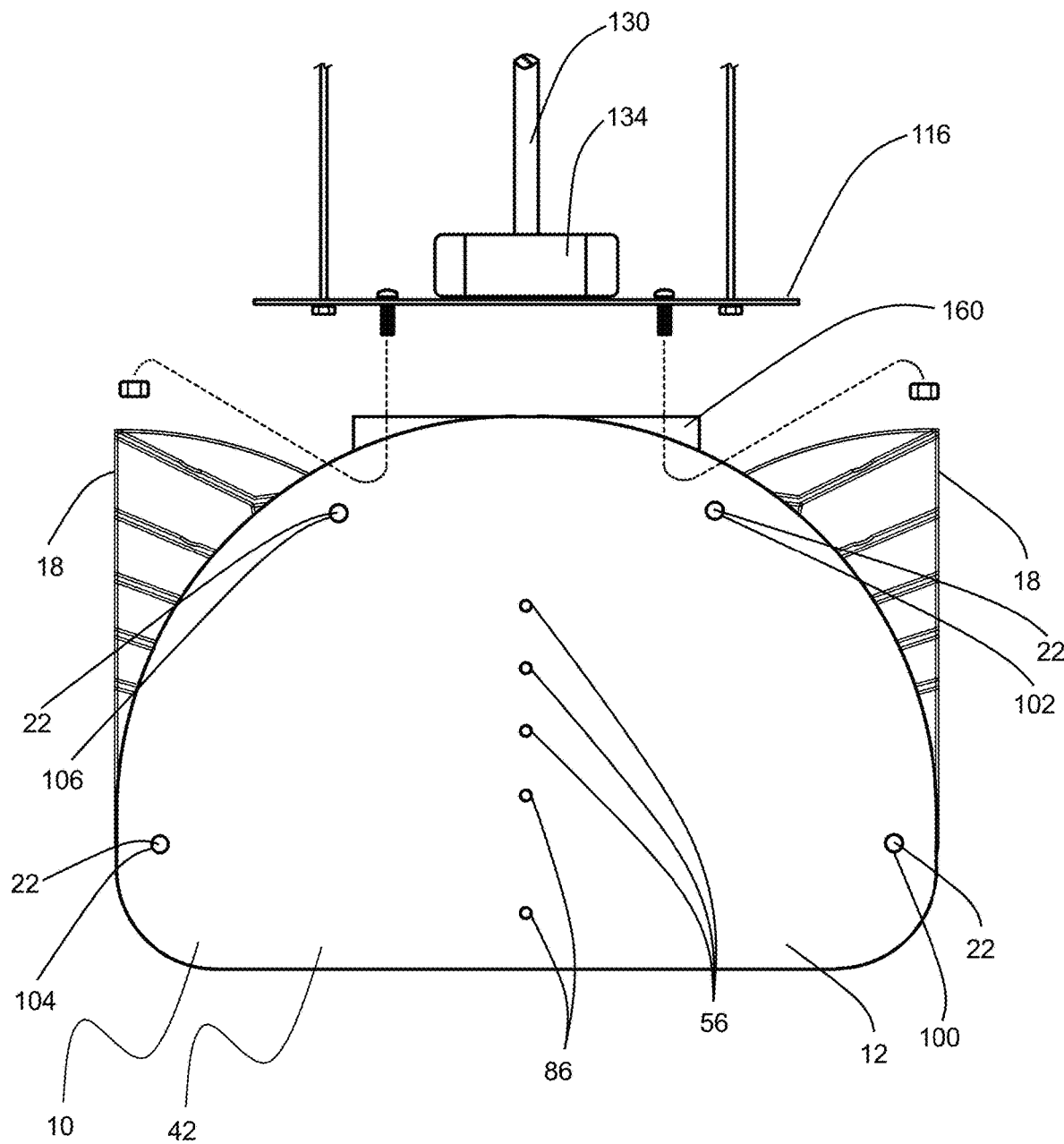

Top plate 16 may be generally rectangular in shape and include edges 58, 60, 62, and 64 that extend downward from top plate 16 to provide plate 16 with added rigidity, strength and means to reflect ultraviolet-C light radiation. Top plate 16 may be manufactured from any material such as aluminum, steel, wood, a polymer and the like. In this particular embodiment of the present invention, top plate 16, may be manufactured from polished aluminum to provide a maximum reflectance of the ultraviolet-C light radiation. Edges 62, 64 may each include a cut-out 66 and 68 sized to engage tube 14. Top plate 16 may include a plurality of holes 70 to align with a plurality of holes 72 on a top surface 74 of tube 14. When top plate 16 is positioned proximate top surface 74 of tube 14 and holes 70 and 52 are aligned, fasteners, such as a screw, bolt and nut, rivets and the like may be used to secure top plate 16 to tube 14 and further provide a rigid mounting structure for fixture 10. Top plate 16 may include a first aperture 76 that may be sized to align with a second aperture 78 of tube 14. Apertures 76 and 78 may be sized allow a typical three wire or four wire insulated electrical wire bundle 130 to pass through to fixture 10 from electrical box 134 to provide electrical power to fixture 10. Further, top plate 16 may include a plurality of fixture mounting holes 80 used to secure fixture 10 to a structure such as ceiling 28 depicted in FIGS. 4A and 13A or a hanging assembly 116 that extends from a high ceiling a length downward to an acceptable height for the dispersion of ultraviolet-C light radiation as depicted in FIG. 13B. Fasteners, such as a screw, bolt and nut and the like may be used to secure fixture 10 to a structure such ceiling 28, hanging assembly 116 and the like.

According to another embodiment of the present invention, fixture 10 may be configured with a top plate 160 as illustrated in FIGS. 8 and 12A-12F. Top plate 160 may be manufactured from any material such as aluminum, steel, wood, a polymer and the like. In this particular embodiment of the present invention, top plate 160, may be manufactured from polished aluminum to provide a maximum reflectance of the ultraviolet-C light radiation. Further, in this particular embodiment of the present invention, top plate 160 may be generally rectangular in shape and include legs 162, 164 that interface with end plates 40, 42. Leg 162 includes a plurality of holes 170 to align with a plurality of holes 54 of end plate 40. Leg 164 includes a plurality of holes 172 to align with a plurality of holes 56 of end plate 42. When legs 162, 164 of plate 160 are positioned proximate end plates 40, 42 and holes 170 and 54 are aligned and holes 172 and 56 aligned, fasteners, such as a screw, bolt and nut, rivets and the like may be used to secure top plate 160 to end plates 40, 42 at holes 170, 54 and holes 172, 56 and provide a rigid mounting structure for fixture 10. Top plate 160 further includes edges 166, 168 that extend downward from top plate 160 to provide top plate 160 with added rigidity, strength and means to reflect ultraviolet-C light radiation. Top plate 160 further includes an aperture 174 sized to allow the passage of a typical three wire or four wire insulated electrical wire bundle 130 into fixture 10 at an electrical box 134 to provide electrical power to fixture 10. Further, top plate 160 may include a plurality of fixture mounting holes 176 used to secure fixture 10 to a structure such as ceiling 28 depicted in FIGS. 4A and 13A or a hanging assembly 116 that extends from a high ceiling a length downward to an acceptable height for the dispersion of ultraviolet-C light radiation as depicted in FIG. 13B. Fasteners, such as a screw, bolt and nut and the like may be used to secure fixture 10 to a structure such ceiling 28, hanging assembly 116 and the like.

Figure 13C:
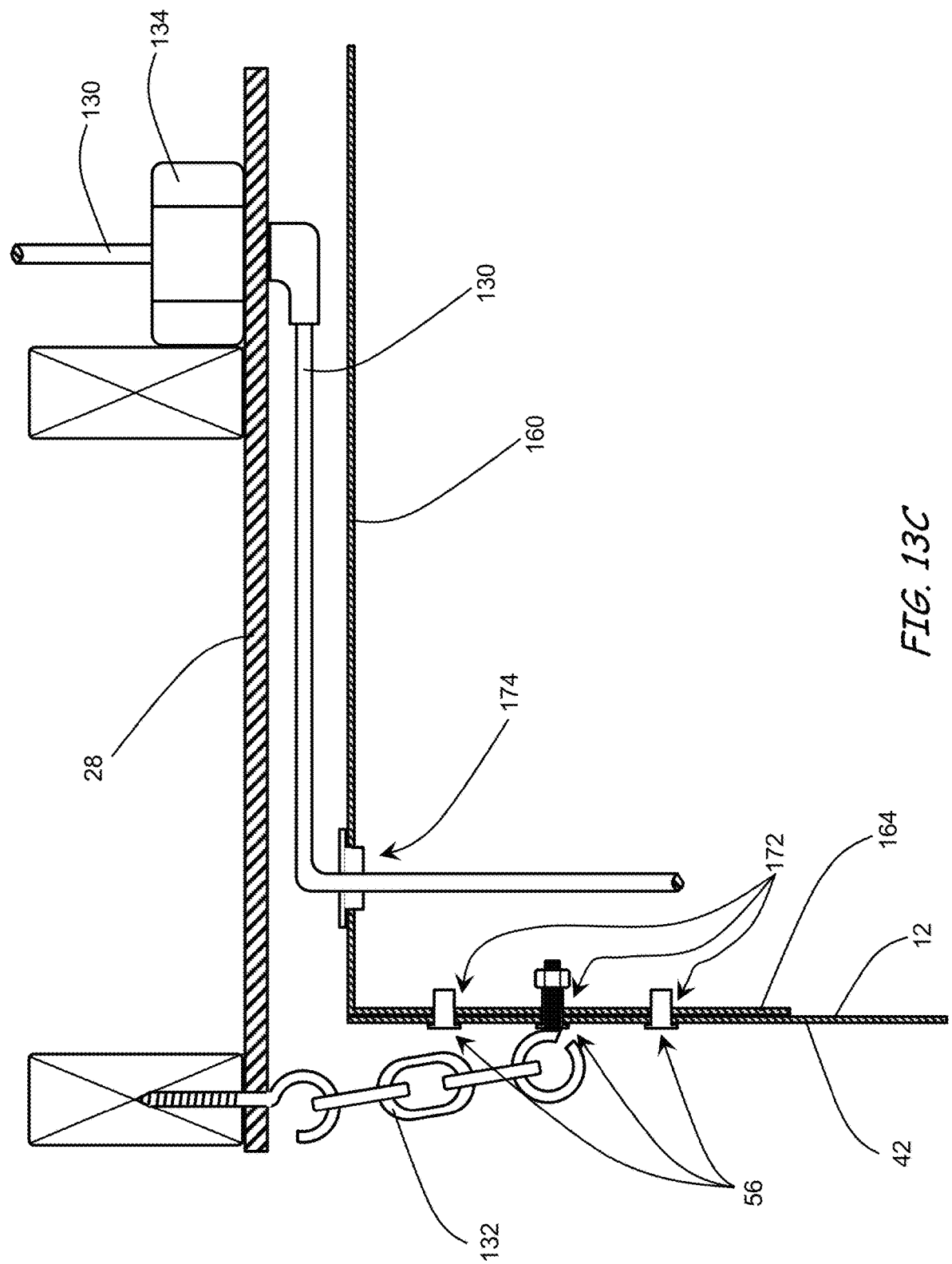
FIG. 13C is a cross-sectional view of the of the ultraviolet light disinfection fixture according to the embodiment of the present invention illustrating still another alternative mounting means to a structure.

FIG. 13C illustrates yet another alternative means for securing fixture 10 to a structure such as ceiling 28. In this particular embodiment of the present invention, a typical eye bolt may be secured to fixture 10 at one of holes 54, 56 of end plates 40, 42 and one of holes 170, 172 of legs 162, 164 of top plate 160. A typical eye screw may be secured to ceiling 28. A standard chain 132 may be used to attach the eye bolt to the eye screw thereby securing fixture 10 to the structure such as ceiling 28. The length of chain 132 may be adjusted to raise and lower fixture 10 to accommodate a variety of ceiling heights relative to the floor of the structure. Securing fixture 10 in this manner will enable fixture 10 to self-level and with respect to the structure to ensure proper alignment of the fixture relative to the structure to maximize exposure of ultraviolet-C light radiation to create the broadest possible disinfection/sterilization field 30 while minimizing ultraviolet-C light radiation to humans and animals present in the room while the fixture is in operation.

Socket 26 may be secured to end plates 40, 42 of tray 14 by way of a typical electrical box 82. End plate 40 includes at least two holes 84 for securing socket 26 and box 82 to end plate 40. End plate 42 includes at least two holes 86 for securing socket 26 and box 82 to end plate 42. When sockets 26 and boxes 82 are positioned proximate end plates 40, 42 and holes 84 and 86 are aligned with mounting holes in sockets 26 and boxes 82, fasteners, such as a screw, bolt and nut, rivets and the like may be used to secure sockets 26 and boxes 82 to end plates 40, 42 at holes 84 and 86. The typical three wire or four wire insulated electrical wire bundle 130 introduced to fixture 10 at electrical box 134 may be connected to sockets 26 through boxes 82 to provide electrical power to sockets 26. Ultraviolet-C light bulb 24 may be secured to socket 26 in typical fashion by rotating the threaded portion of blub 24 into socket 26 until an electrical connection is made between bulb 24 and socket 26 such that bulb 24 is illuminated when power to fixture 10 is actuated. In this particular embodiment of the present invention, two ultraviolet-C bulbs 24 may be used with fixture 10, but it is important to note, that any number of bulbs 24, fluorescent tubes 128, sockets 26 and electrical boxes 82 may be used with fixture 10 to produce ultraviolet-C light radiation to eradicate viruses, bacteria and pathogens. FIG. 5C illustrates a smaller fixture 10 with a single bulb 24 and socket 26 for use in smaller rooms and enclosures. Fixture 10 will become operational when a source of electrical power is connected to fixture 10 at socket 26 to energize and illuminate ultraviolet-C bulbs 24.

Figure 15A:
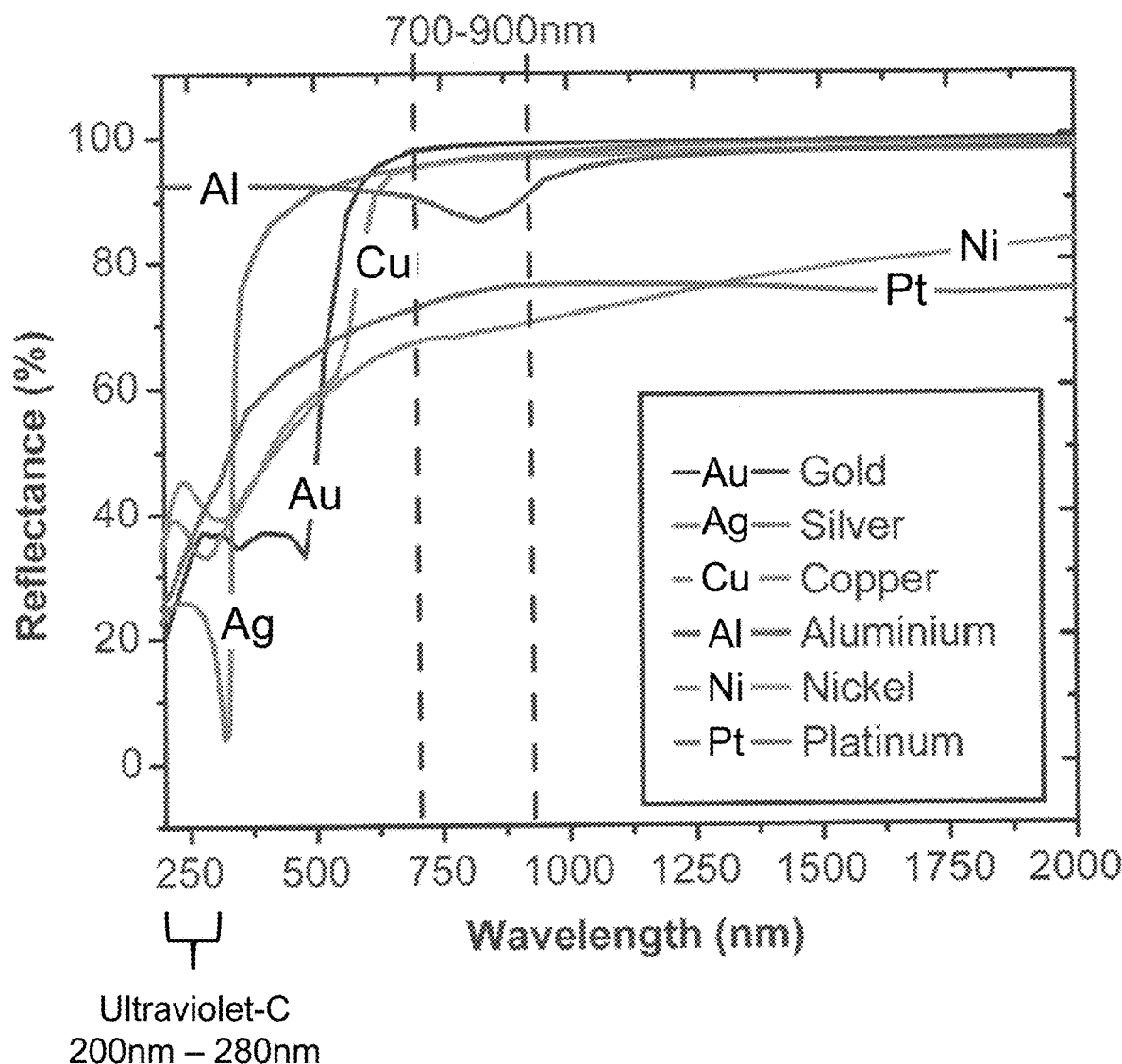
FIGS. 15A and 15B are graphical figures illustrating the reflectance level of aluminum at various wavelengths as compared to other metals.
Figure 15B:
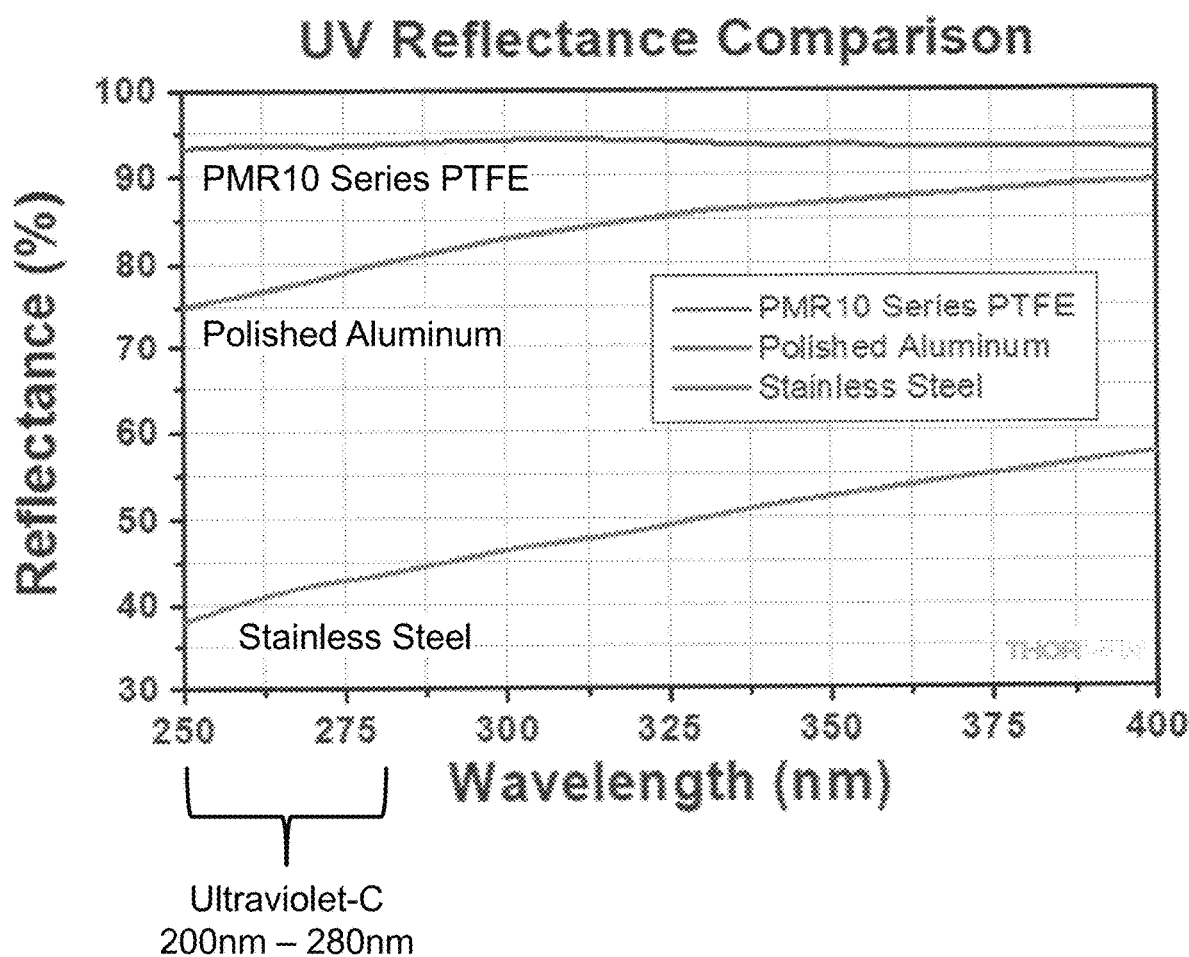

Now referring to FIGS. 10A-10F, a louver assembly 88 of fixture 10 is depicted. Louver assembly 88 includes at least one louver mount 18 and a plurality of ultraviolet-C light radiation reflective louvers 20. Louver mounts 18 may be manufactured from any type of polymer, ceramic, metal, cellulous and like materials. Ultraviolet-C light radiation reflective louvers 20 may be fabricated from any type of material have a high reflectance to ultraviolet-C light. Those materials may include aluminum, gold, silver, copper, nickel, platinum, polytetrafluoroethylene (PTFE) and like materials as illustrated in the graphs of FIGS. 15A and 15B. In this particular embodiment of the present invention, ultraviolet-C light radiation reflective louvers 20 may be fabricated from polished aluminum. Polishing aluminum to a mirror-like finish will increase the reflectance of louvers 20.

In this particular embodiment of the present invention, each louver assembly 88 includes two louver mounts 18*a*, 18*b* and seven ultraviolet-C light radiation reflective louvers 20*a*, 20*b*, 20*c*, 20*d*, 20*e*, 20*f* and 20*g*. Louver mounts 18 may be manufactured of a light weight polymer yet are rigid enough to support each of the seven louvers 20. Louver mount 18 includes seven slots 90*a*, 90*b*, 90*c*, 90*d*, 90*e*, 90*f* and 90*g* sized to secure each of seven louvers 20 to mount 18. Each of seven slots 90 also include a divot 92 to further secure louvers 20 to mount 18. Louvers 20 may be of a shape that is generally rectangular in nature and be of a thickness capable of being seated in slots 90. Each of louvers 20 may be fabricated from aluminum and polished to have a high reflectance of ultraviolet-C light. The table in FIG. 15A illustrates that aluminum has the highest reflectance of ultraviolet-C light versus the other metals in the table. A disinfection fixture including a material such as aluminum having high reflectance of ultraviolet-C light is desired to direct the ultraviolet-C light radiation outside fixture 10 to increase the disinfection/sterilization field exterior to and around fixture 10 and to ensure the ultraviolet-C light radiation exiting fixture 10 is at a suitable level to destroy airborne viruses, bacteria and pathogens a distance away from fixture 10.

Ultraviolet-C light radiation reflective louvers 20 may be assembled to mounts 18 in the following manner. An end 94 of louvers 20 may be inserted into slots 90 of mount 18. Divots 92 will provide a compressive down force on ends 94 as ends 94 are introduced and inserted into slots 90. Divots 92 provide adequate down force against ends 94 of louvers 20 to secure louvers 20 to mount 18 prior to final assembly to fixture 10. When all of seven louvers 20 are secured to a first mount 18*a*, the opposite ends 94 of louvers 20 may be inserted into the slots of a second mount 18*b* in a similar manner as described above for first mount 18*a* to secure louvers 20 to second mount 18*b* and create louver assembly 88 (see FIG. 10F).

Upon fabrication of louver assembly 88, louver assembly 88 may be assembled to tray 12 to create fixture 10. Each mount 18 includes a first aperture 96 and a second aperture 98 sized to allow dowel rod 22 to pass through freely. Each mount 18 also includes a tab 110 that may engage a strike point 108 of edge 68 of top plate 16 or edge 168 of top plate 160 when mount 18 is full assembled to fixture 10. End plates 40, 42 of tray 12 each include holes 100, 102, 104 and 106 and holes 100, 102, 104 and 106 are sized to allow dowel rod 22 to pass through freely. First aperture 96 of each mount 18 of louver assembly 88 may be aligned with holes 100 of end plates 40, 42. Dowel rod 22 may be introduced into hole 100 of end plate 40 and dowel rod 22 may pass thorough first apertures 96 of mounts 18*a*, 18*b* and out of hole 100 of end plate 42. Dowel rod 22 may be secured to tray 12 at end plates 40, 42 with the use of typical fasteners such as c-clips, bolts, and the like to secure dowel rod 22 and louver assembly 88 to tray 12. With louver assembly 88 attached to tray 12 by lower dowel rod 22, louver assembly may be rotated upward about lower dowel rod 22 such that second aperture 98 of each mount 18 of louver assembly 88 may be aligned with holes 102 of end plates 40, 42. Dowel rod 22 may be introduced into hole 102 of end plate 40 and dowel rod 22 may pass thorough first apertures 98 of mounts 18*a*, 18*b* and out of hole 102 of end plate 42. Dowel rod 22 may be secured to tray 12 at end plates 40, 42 with the use of typical fasteners such as c-clips, bolts, and the like to secure dowel rod 22 and louver assembly 88 to tray 12. The same process may be used to secure a second louver assembly 88 to the opposite side of tray 14 to create fixture 10.

Figure 12A:
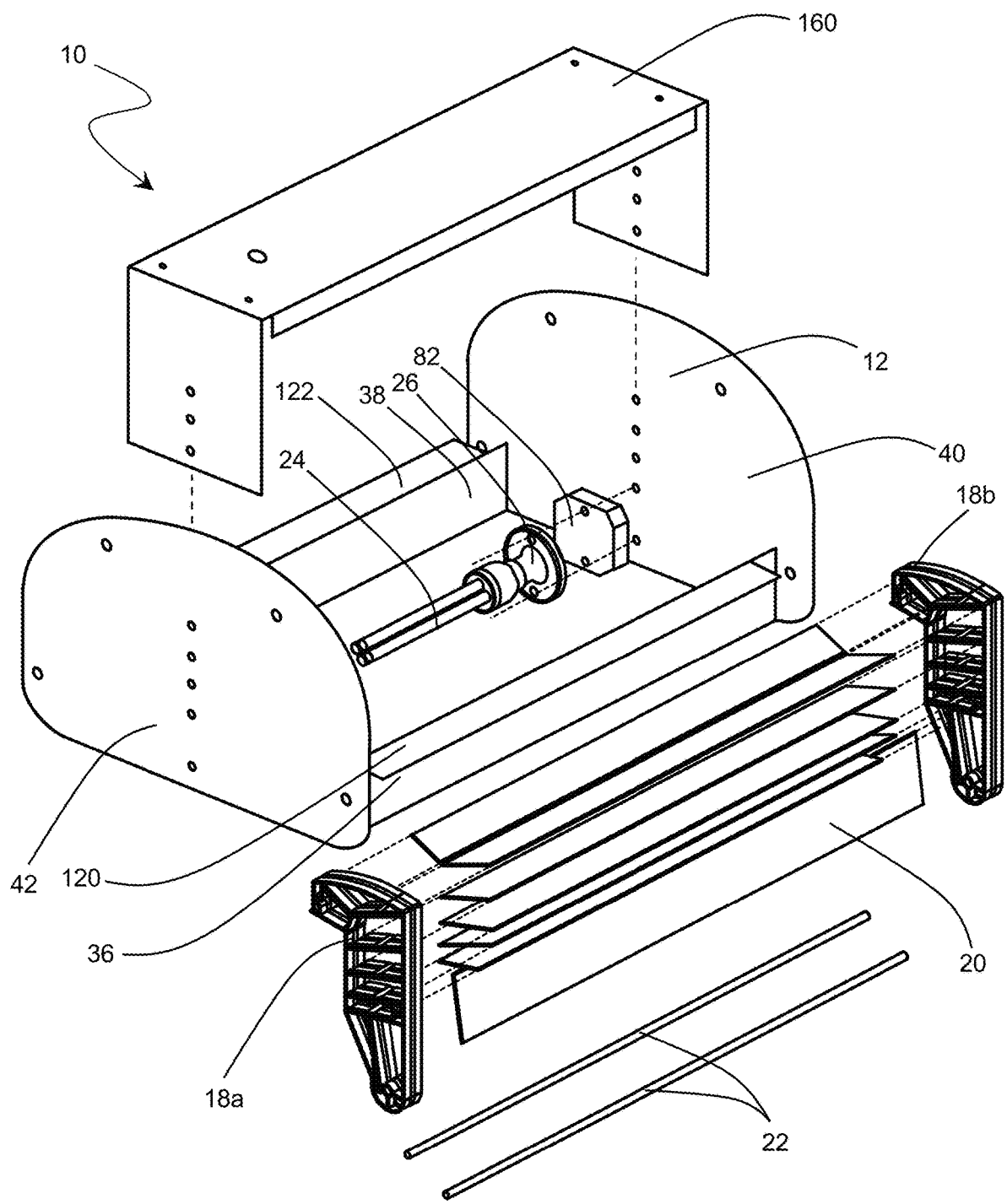
FIGS. 12A-12E are exploded views of the components of the ultraviolet light disinfection fixture of FIG. 3 according to the embodiment of the present invention.
Figure 12B:
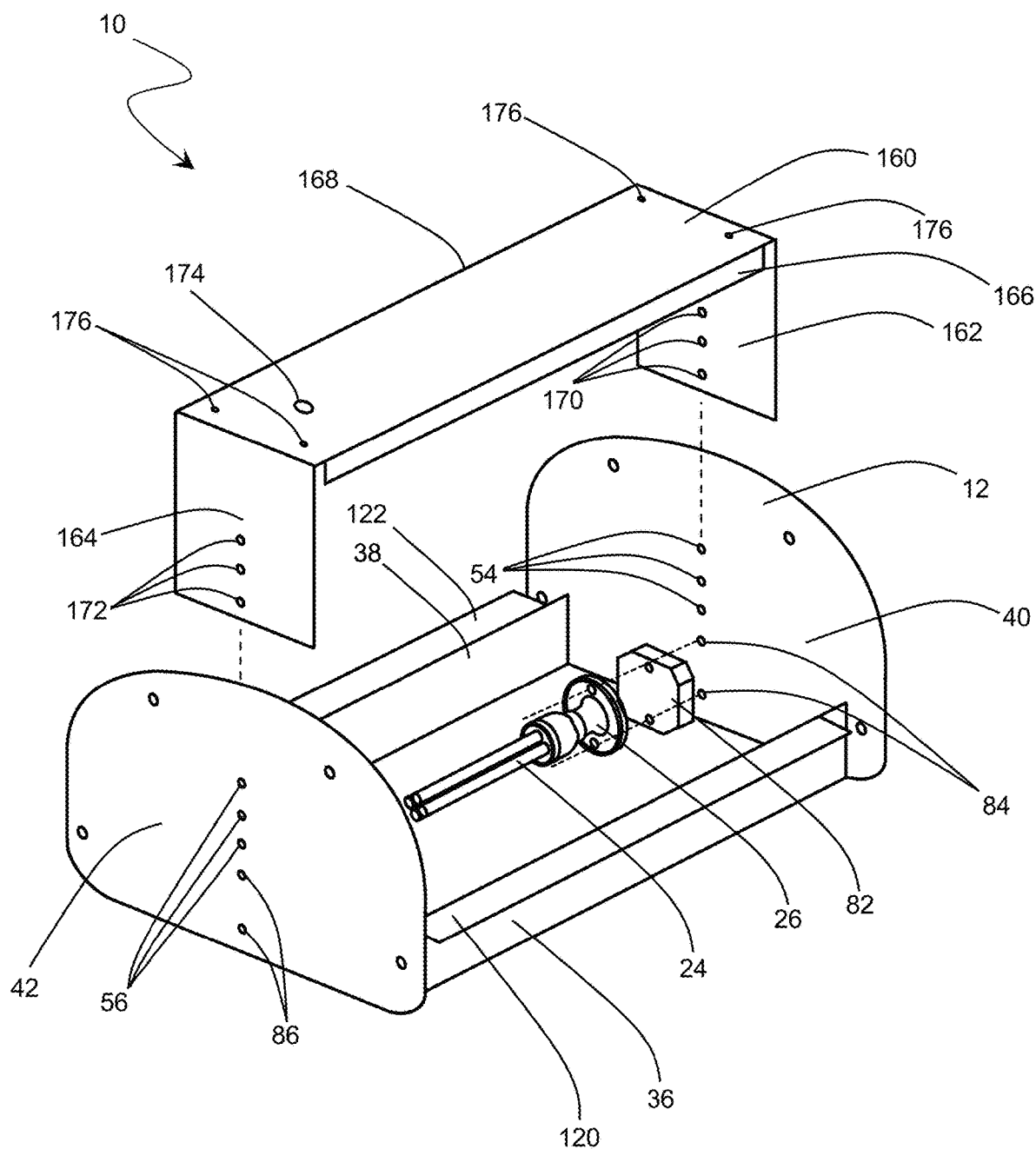
Figure 12C:
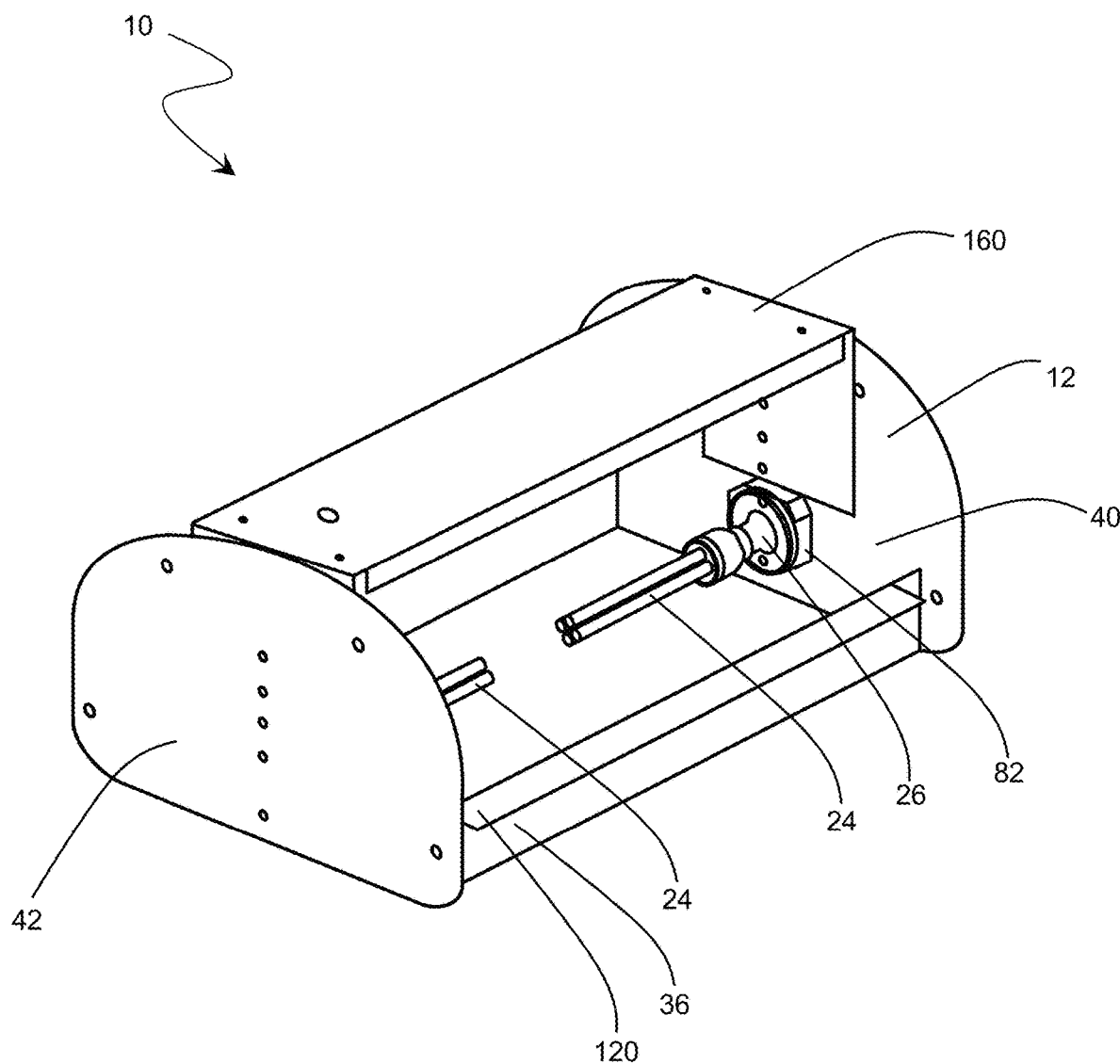
Figure 12D:
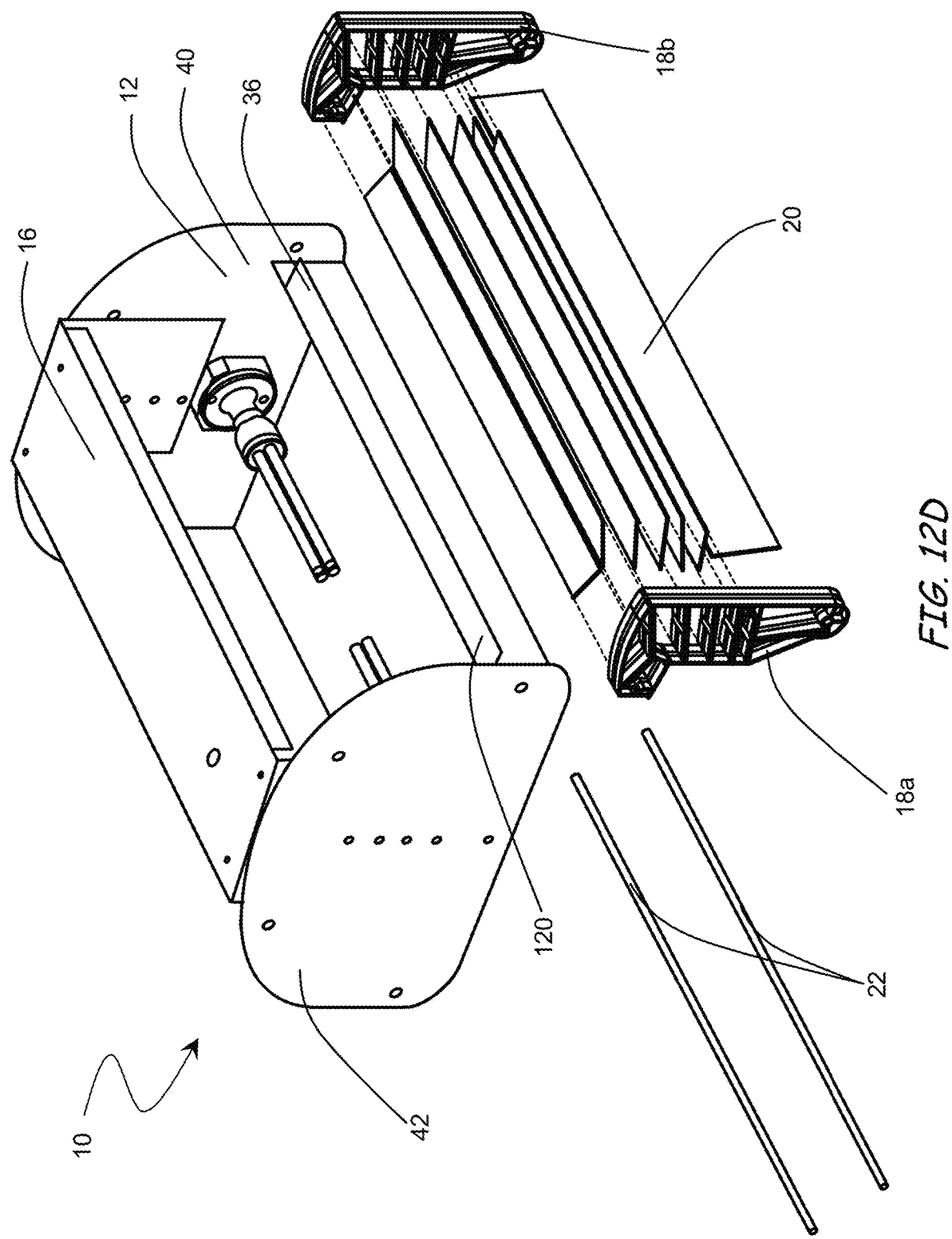
Figure 12E:
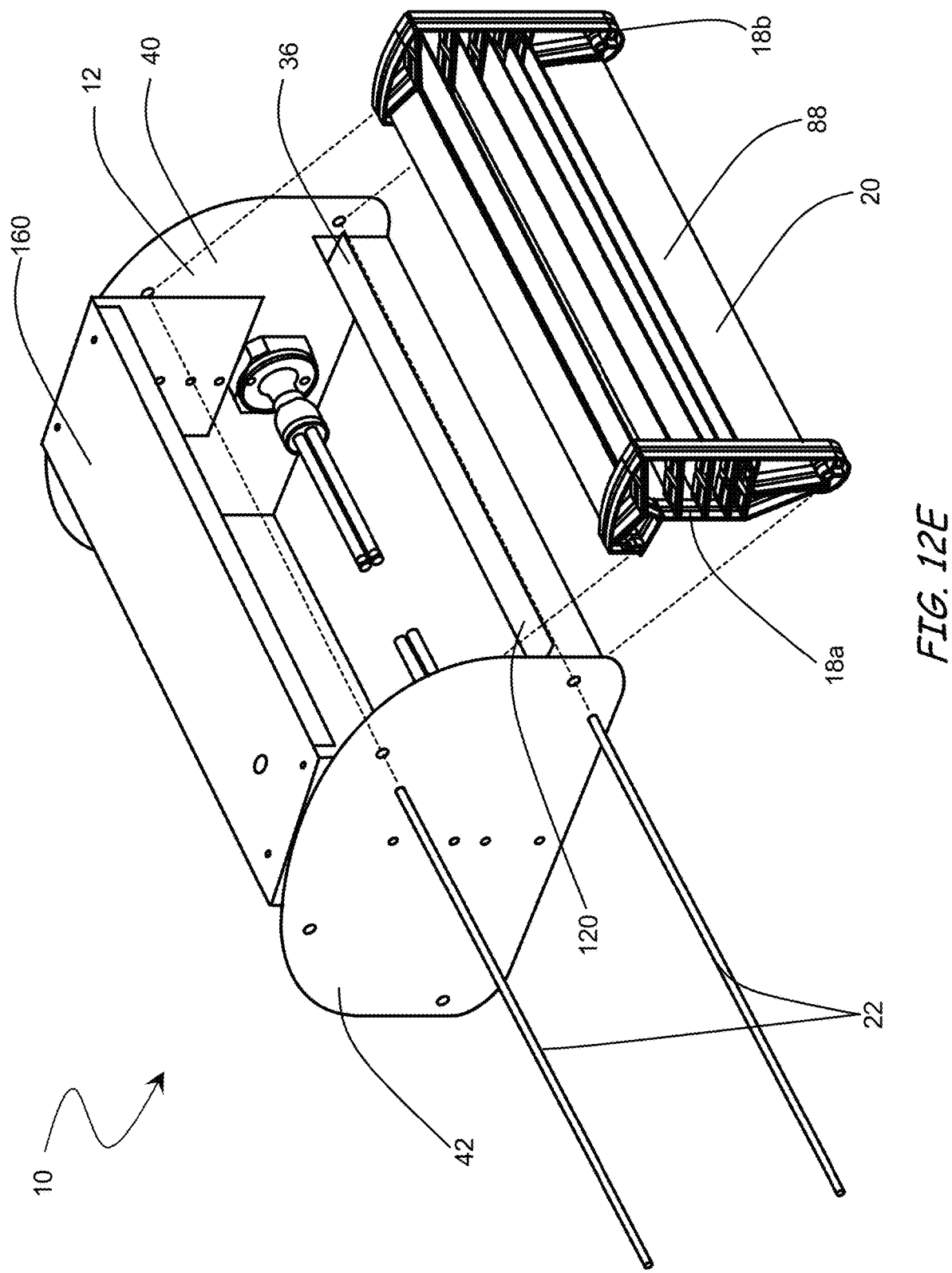
Figure 12F:
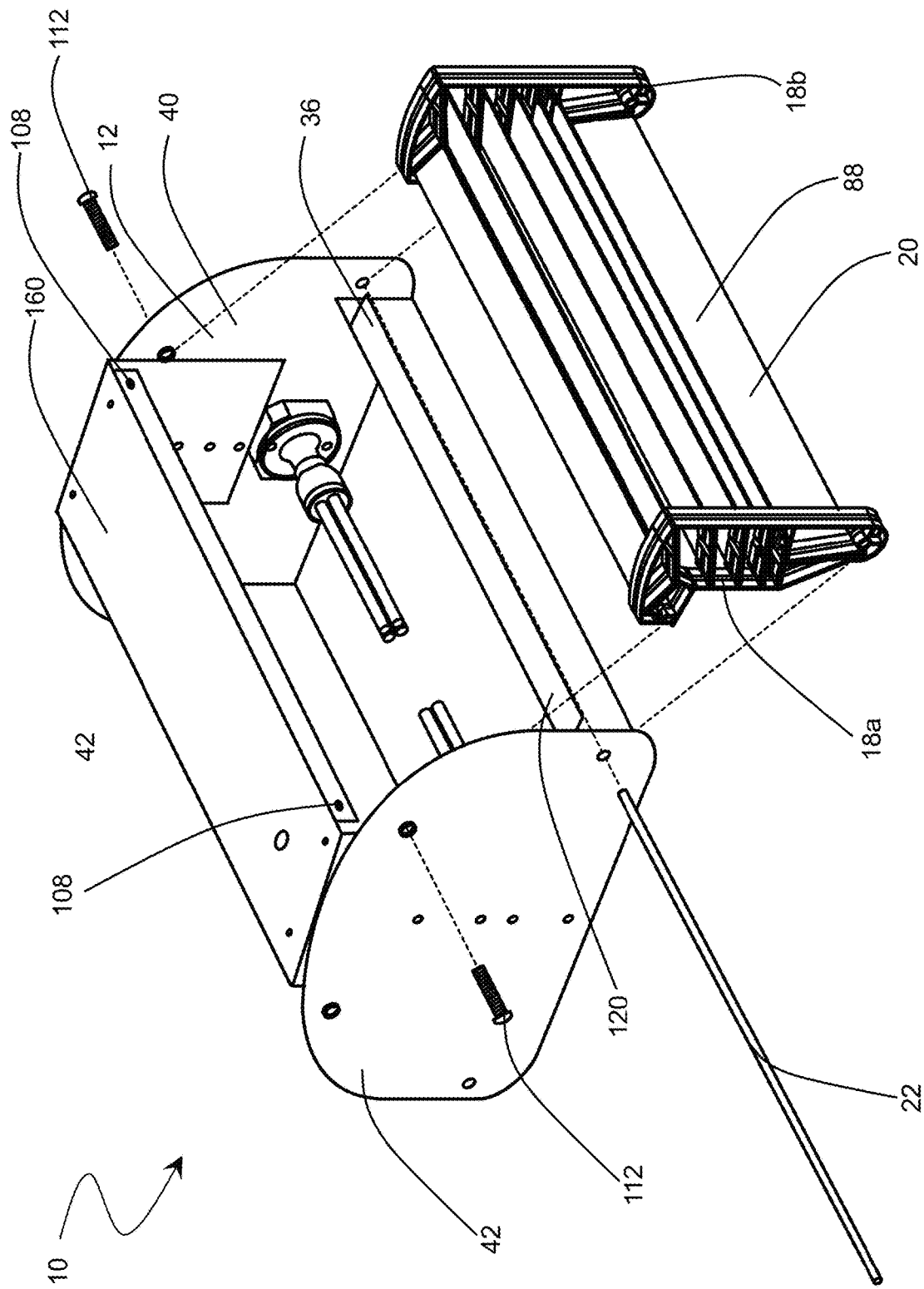
FIG. 12F is an exploded views of the components of the ultraviolet light disinfection fixture of FIG. 3 according to the embodiment of the present invention illustrating an alternative means to attach a louver assembly to a tray.

FIG. 12F illustrates an alternative means for attaching louver assembly 88 to tray 12. In this particular embodiment of the present invention, at least one fastener 112 (fastener 112 may be any typical threaded bolt such as a hurricane bolt and the like, that may be secured to a nut) may be used to secure the upper portion of louver mount 18 at second aperture 98. The upper dowel rod 22 may be removed from fixture 10. Typical rivet nuts having a threaded internal diameter may be attached at holes 102 and 106 of end plates 40, 42 to accept the threaded outer diameter of fastener 112 to secure fastener 112 to end plates 40, 42. Aperture 98 may have a smaller inner diameter than the outer diameter of fastener 112 to create an interference fit between fastener 112 and aperture 98 to secure fastener 112 to mount 18. Aperture 98 may also include a guide having an inner diameter greater than the outside diameter of fastener 112 to guide bolt 112 into aperture 98.

With louver assembly 88 attached to tray 12 by lower dowel rod 22 as described above, louver assembly may be rotated upward about lower dowel rod 22 such tabs 110 of mounts 18a, 18b engage edge 58 of top plate 16 or edge 166 of top plate 160 at strike points 108. This will align second aperture 98 of each mount 18 of louver assembly 88 with holes 102 of end plates 40, 42. Fastener 112 may be introduced into the rivet nut at hole 102 of end plate 40 and fastener 112 may pass thorough the rivet nut and into first aperture 98 of mount 18a. Fastener 112 may be introduced into the rivet nut at hole 102 of end plate 42 and fastener 112 may pass thorough the rivet nut and into first aperture 98 of mount 18b. The same process may be used to secure a second louver assembly 88 to the opposite side of tray 14 to create fixture 10.

Fasteners 112 may also be removed from fixture 10 to allow louver assembly 88 to rotate downward. The ability to remove fasteners 112 and rotate louver assembly 88 downward will provide access to the interior of fixture 10 to perform maintenance (e.g., changing an ultraviolet-C light bulb) or cleaning of fixture 10.

The size, positioning and choice of material for each of ultraviolet-C light radiation reflective louvers 20a, 20b, 20c, 20d, 20e, 20f and 20g is critical to maximize reflectance both within and outside fixture 10 and to direct the ultraviolet-C light radiation such that a maximum amount of ultraviolet-C light radiation is available to kill harmful viruses, bacteria and pathogens while at the same time allowing the presence of humans and animals while fixture 10 is in operation. Regarding choice of material, as described above, any of the materials depicted in FIGS. 15A and 15B may be used in the fabrication of louvers 20. However, the reflectance or intensity of the ultraviolet-C light radiation is dependent on the louver material having a high modulus and being relatively thin. In this particular embodiment of the present invention, aluminum is used as the material for louvers 20. Aluminum has a higher reflectance in the ultraviolet-C wavelength and is much less expensive than silver or gold (see FIG. 15A). While PTFE may have a higher reflectance than aluminum (see FIG. 15B), PTFE is a very low modulus material and would have to be much thicker than aluminum to span the distance between mounts 18a, 18b and maintain rigidity and ensure a uniform angle of reflectance throughout fixture 10. Therefore, aluminum is the choice of material for this particular embodiment of the present invention.

Furthermore, ultraviolet-C light radiation reflective louvers 20 may have a polished mirror-line finish to have a reflectance greater than 85%. Ultraviolet-C light radiation that is not reflected by louvers 20 or other components of fixture 10, may be either absorbed by ultraviolet-C light radiation absorbing pad 44 (see FIGS. 14A-14F) or scattered outside of fixture 10. Pad 44 may be manufactured of any type of material suitable for absorbing ultraviolet-C light radiation including polymers such as glass fiber reinforced polypropylene (PP) or acrylonitrile butadiene styrene (ABS). As stated above, controlling the amount and direction of ultraviolet-C light radiation around the exterior of fixture 10 is critical for creating a disinfection/sterilization field 30 or kill zone capable of killing the maximum number of viruses, bacteria and pathogens without harming humans or animals. Mirrored finished aluminum will limit the scatter to no more than 5 degrees, thereby ensuring ultraviolet-C light radiation will not harm humans and animals while fixture 10 is in operation killing viruses, bacteria and pathogens.

Referring now to FIGS. 14A-14F and regarding the size and positioning of each of ultraviolet-C light radiation reflective louvers 20a, 20b, 20c, 20d, 20e, 20f and 20g, the ultraviolet-C light radiation output from bulbs 24 were used to calculate the louver size, louver location and angle of the louvers relative to base plate 34. Further, the interior widths of top plate 16 and top plate 160, as well as the downward length of edges 58, 60 of top plate 16 and edges 166, 168 of top plate 160 were also determined by the ultraviolet-C light radiation output of bulbs 24. In this particular embodiment of the present invention, two bulbs are used in fixture 10 with each bulb producing 36 watts for a total of 72 watts of ultraviolet-C light radiation. However, it is important to note that any bulb wattage may be used with corresponding changes to the louver sizes and positions to maintain the function of fixture 10. Further, other sources of ultraviolet-C light radiation may be used with fixture 10. For example, FIG. 5D illustrates ultraviolet-C fluorescent tube 128 added to fixture 10 as a source of ultraviolet-C light radiation.

The width of ultraviolet-C light radiation reflective louvers 20a, 20b, 20c, 20d, 20e, 20f and 20g, the angle of 20a, 20b, 20c, 20d, 20e, 20f and 20g relative to base plate 34 of tray 12, the interior widths of top plate 16 and top plate 160, as well as the downward length of edges 58, 62 of top plate 16 and edges 166, 168 of top plate 160 may be designed to maintain a maximum upward angle of reflection of ultraviolet-C light radiation at 14 degrees relative to base plate 34 and a maximum downward angle of reflection of ultraviolet-C light radiation at 5 degrees relative to base plate 34. Limiting the ultraviolet-C light radiation output angles to a maximum of 14 degrees upward and 5 degrees downward is critical for creating the disinfection/sterilization field 30 or kill zone capable of killing the maximum number of viruses, bacteria and pathogens without harming humans or animals.

Further, the width of ultraviolet-C light radiation reflective louvers 20a, 20b, 20c, 20d, 20e, 20f and 20g, the angle of 20a, 20b, 20c, 20d, 20e, 20f and 20g relative to the other louvers and the interior widths of top plate 16 and top plate 160, as well as the downward length of edges 58, 62 of top plate 16 and edges 166, 168 of top plate 160 are also critical to maintaining a maximum upward angle of reflection output of ultraviolet-C light radiation at 14 degrees relative to base plate 34 and a maximum downward angle of reflection output of ultraviolet-C light radiation at 5 degrees relative to base plate 34. Positioning of a top edge or bottom edge of a particular louver to the louver above or below the louver (e.g., louver 20c relative to louver 20b and louver 20d) is also critical to maintaining the maximum upward (14 degrees) and downward (5 degrees) angle of reflection output from fixture 10.

In this particular embodiment of the present invention, ultraviolet-C light radiation reflective louvers 20a, 20b, 20c, 20d, 20e, 20f and 20g may be positioned at the following approximate angles relative to base plate 34 to ensure a maximum upward angle of reflection of ultraviolet-C light radiation at 14 degrees relative to base plate 34 and a maximum downward angle of reflection of ultraviolet-C light radiation at 5 degrees relative to base plate 34.

Louver 20a may angle upward from fixture 10 relative to base plate 34 at approximately 26 degrees to create a range of ultraviolet-C light radiation output angles of between approximately 5 degrees downward and approximately 8 degrees upward.

Louver 20b may angle upward from fixture 10 relative to base plate 34 at approximately 23.5 degrees to create a range of ultraviolet-C light radiation output angles of between approximately 4 degrees downward and approximately 9 degrees upward.

Louver 20c may angle upward from fixture 10 relative to base plate 34 at approximately 20.5 degrees to create a range of ultraviolet-C light radiation output angles of between approximately 4 degrees downward and approximately 9 degrees upward.

Louver 20*d* may angle upward from fixture 10 relative to base plate 34 at approximately 18 degrees to create a range of ultraviolet-C light radiation output angles of between approximately 4 degrees downward and approximately 10 degrees upward.

Louver 20*e* may angle upward from fixture 10 relative to base plate 34 at approximately 15.5 degrees to create a range of ultraviolet-C light radiation output angles of between approximately 4 degrees downward and approximately 10 degrees upward.

Louver 20*f* may angle inward from fixture 10 relative to a vertical extending perpendicular to base plate 34 at approximately 7 degrees to cooperate with louver 20*e* and side walls 36, 38 to limit the range of ultraviolet-C light radiation output angles of between approximately 5 degrees downward and approximately 14 degrees upward.

Louver 20*g* may angle upward from fixture 10 relative to base plate 34 at approximately 26 degrees to create a range of ultraviolet-C light radiation output angles of between approximately 4 degrees downward and approximately 10 degrees upward.

Still further, the angles of side walls 36, 38 and wings 120, 122 of tray 12 relative to base plate 34 are also critical to maintaining the maximum upward (14 degrees) and downward (5 degrees) angle of reflection output from fixture 10. In this particular embodiment of the present invention, side walls 36, 38 may angle outward from fixture 10 relative to a vertical extending perpendicular to base plate 34 at approximately 10 degrees.

Figure 14A:
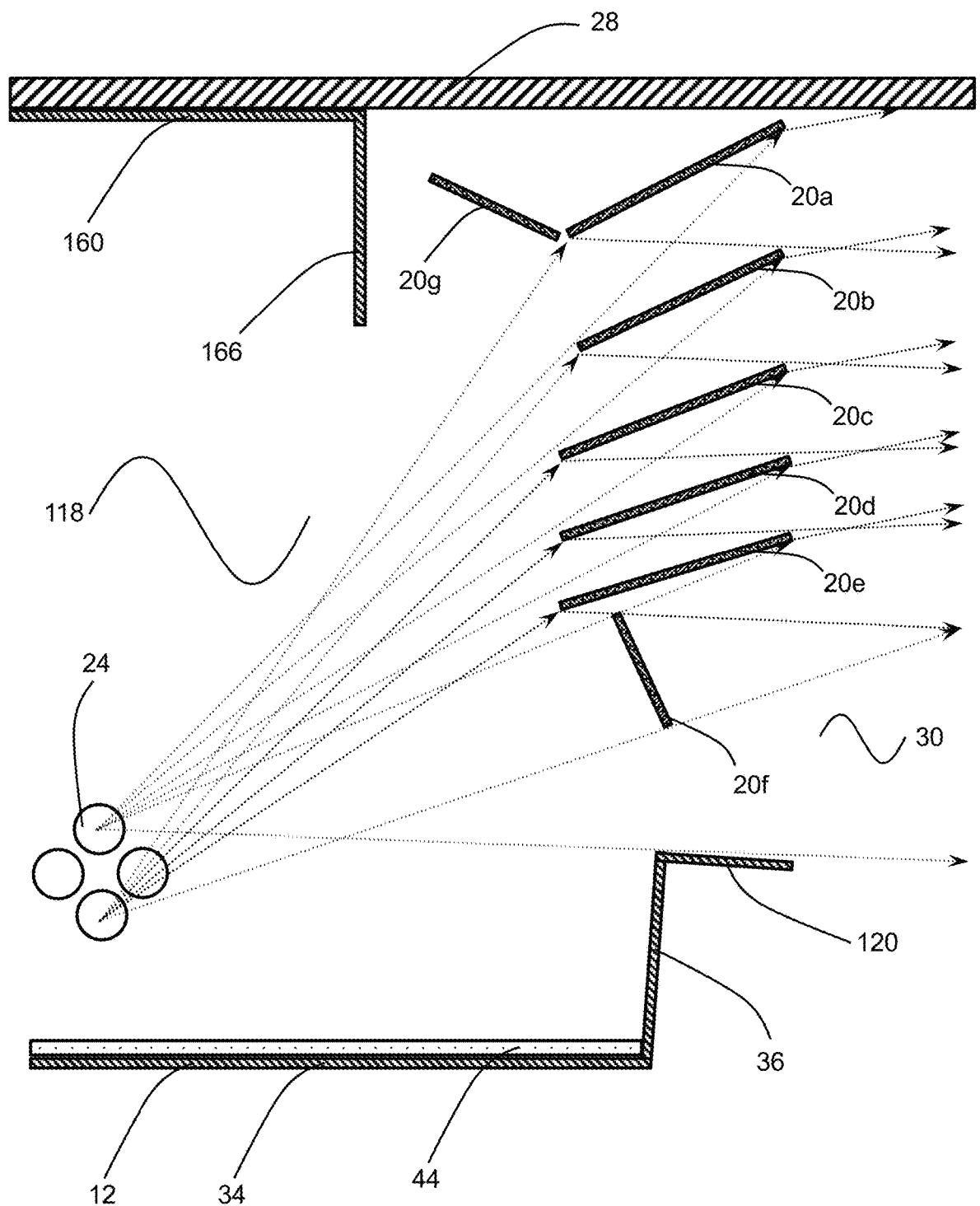
FIGS. 14A-14G are cross-sectional views of the ultraviolet light disinfection fixture according to the embodiment of the present invention illustrating the reflectance of ultraviolet light within the fixture and exiting the fixture.
Figure 14B:
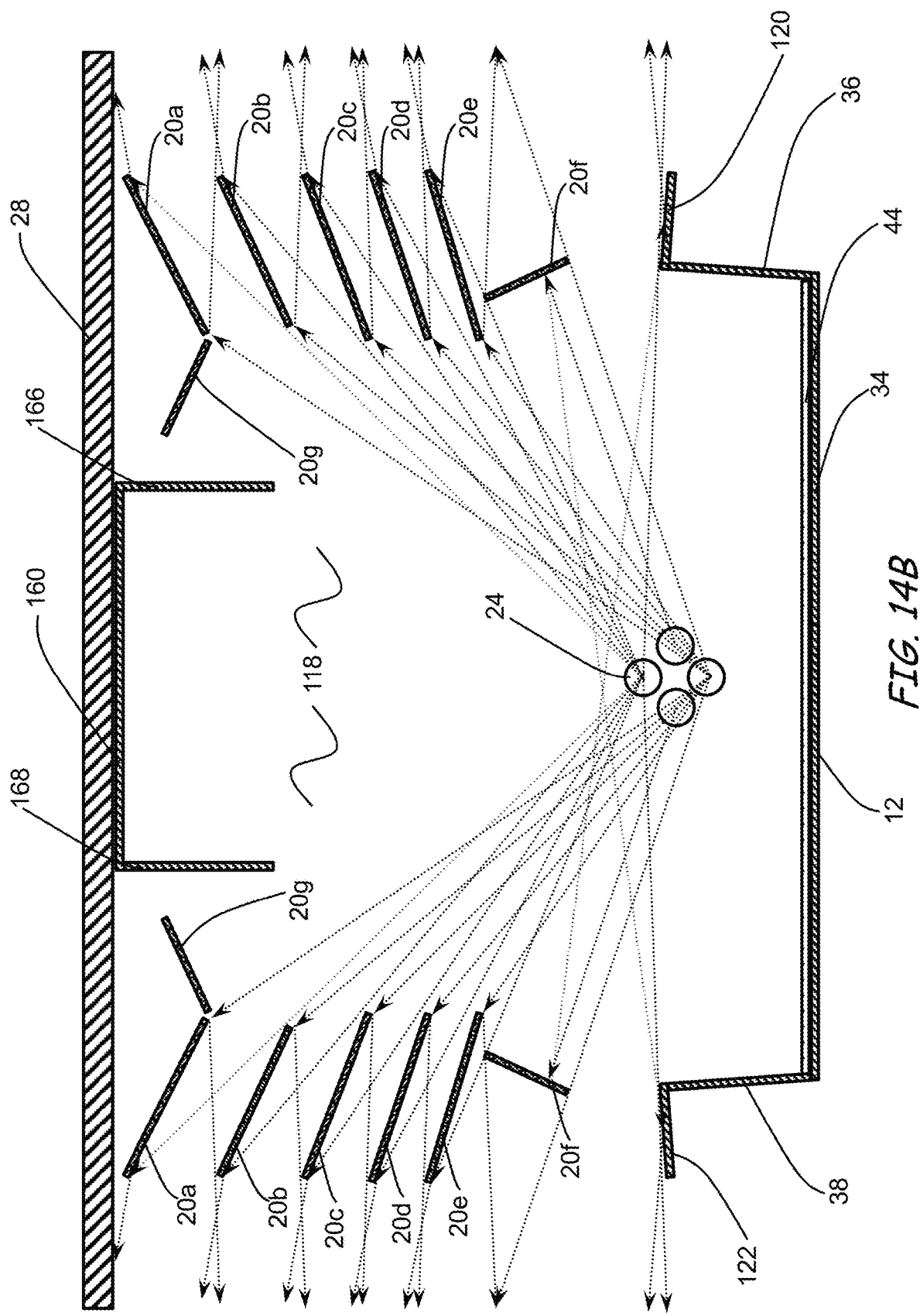
Figure 14C:
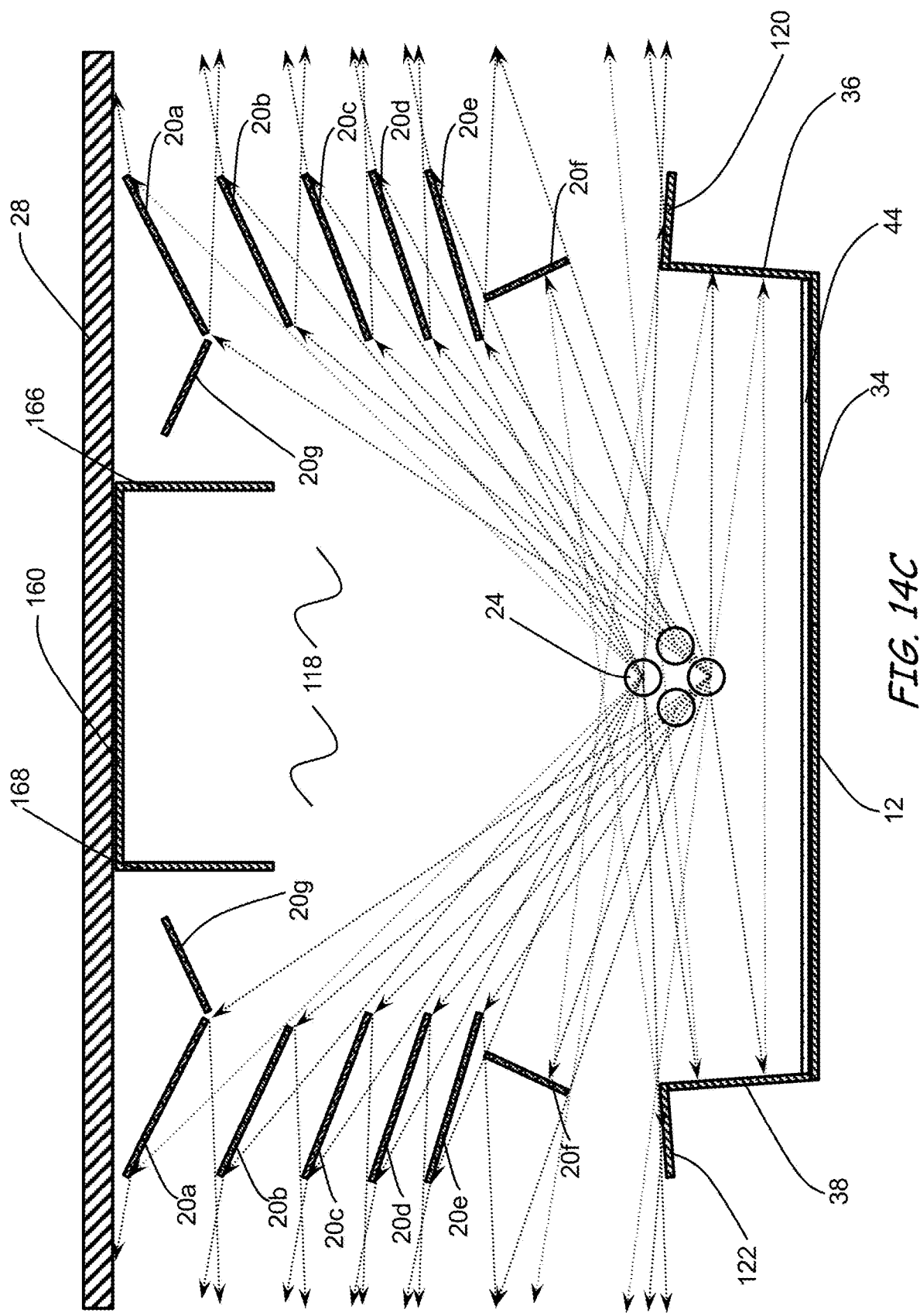
Figure 14D:
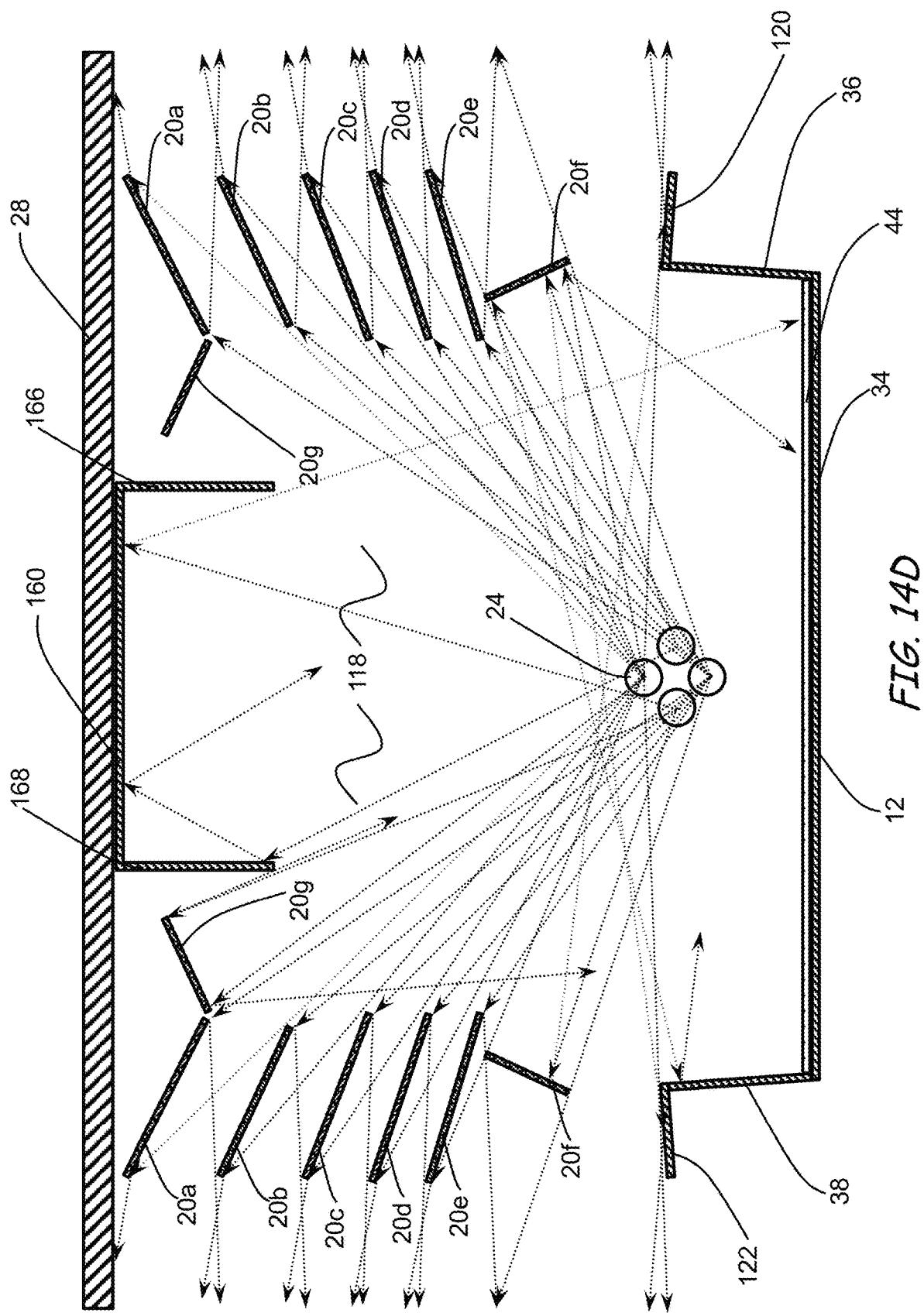
Figure 14E:
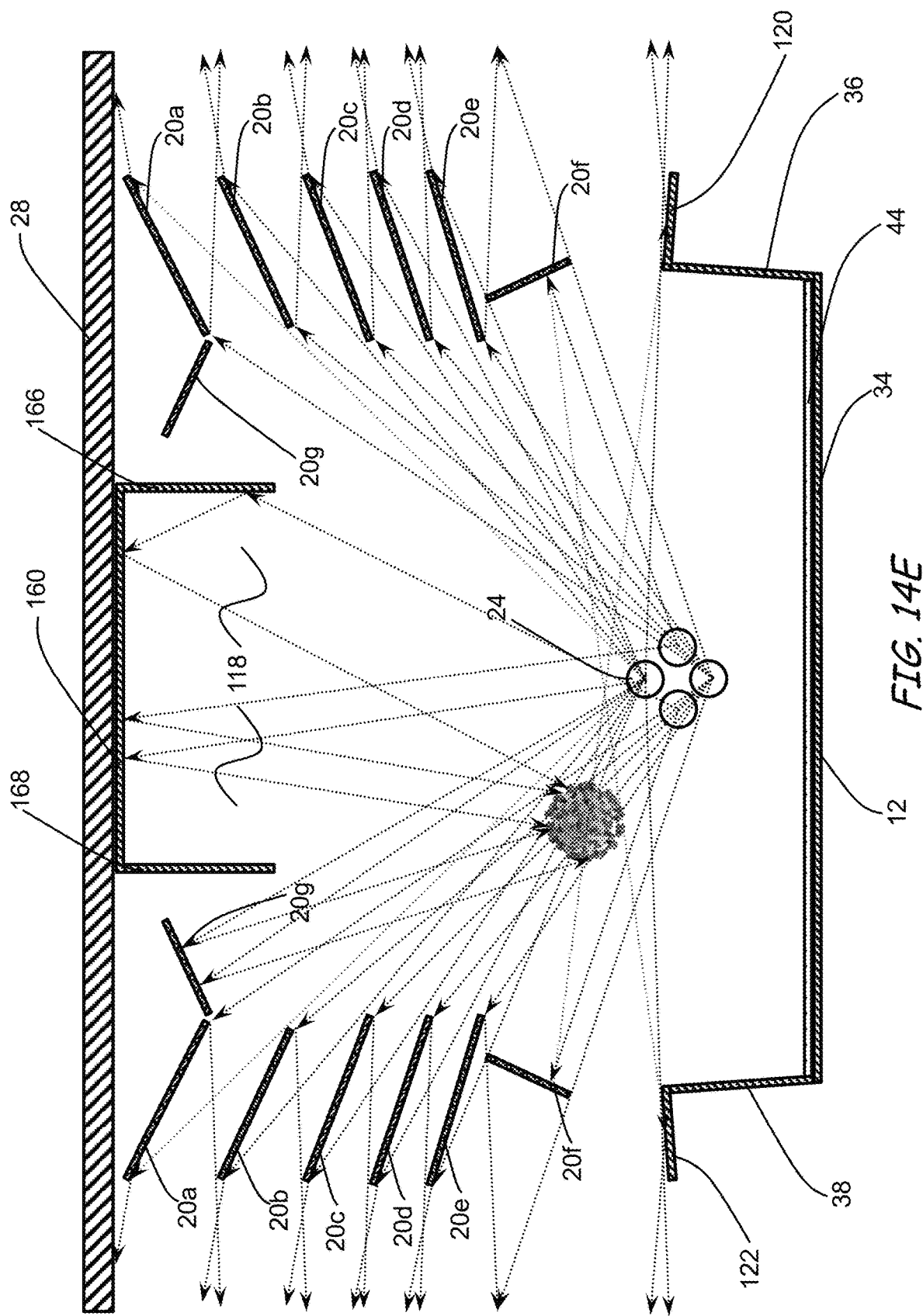
Figure 14F:
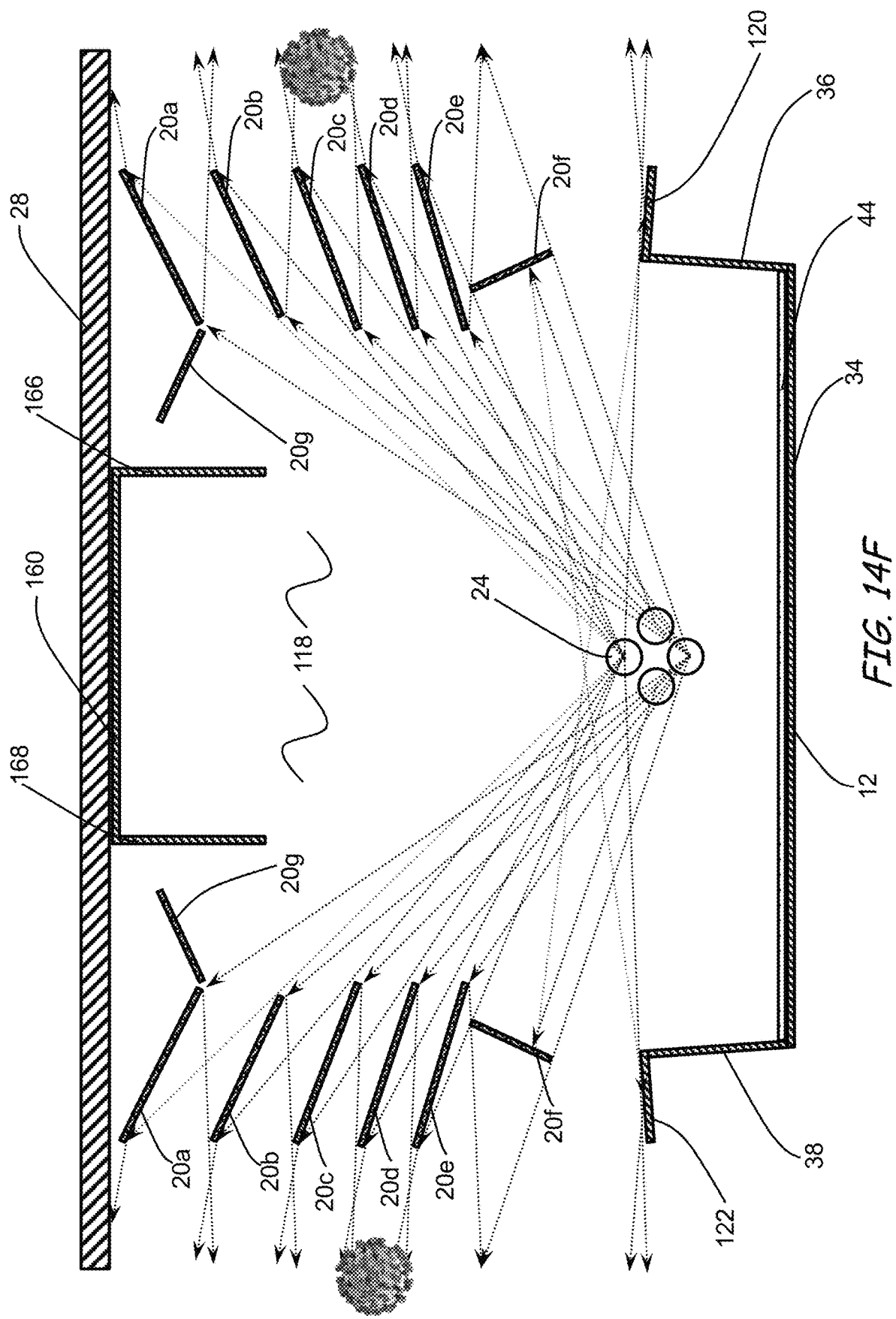
Figure 14G:
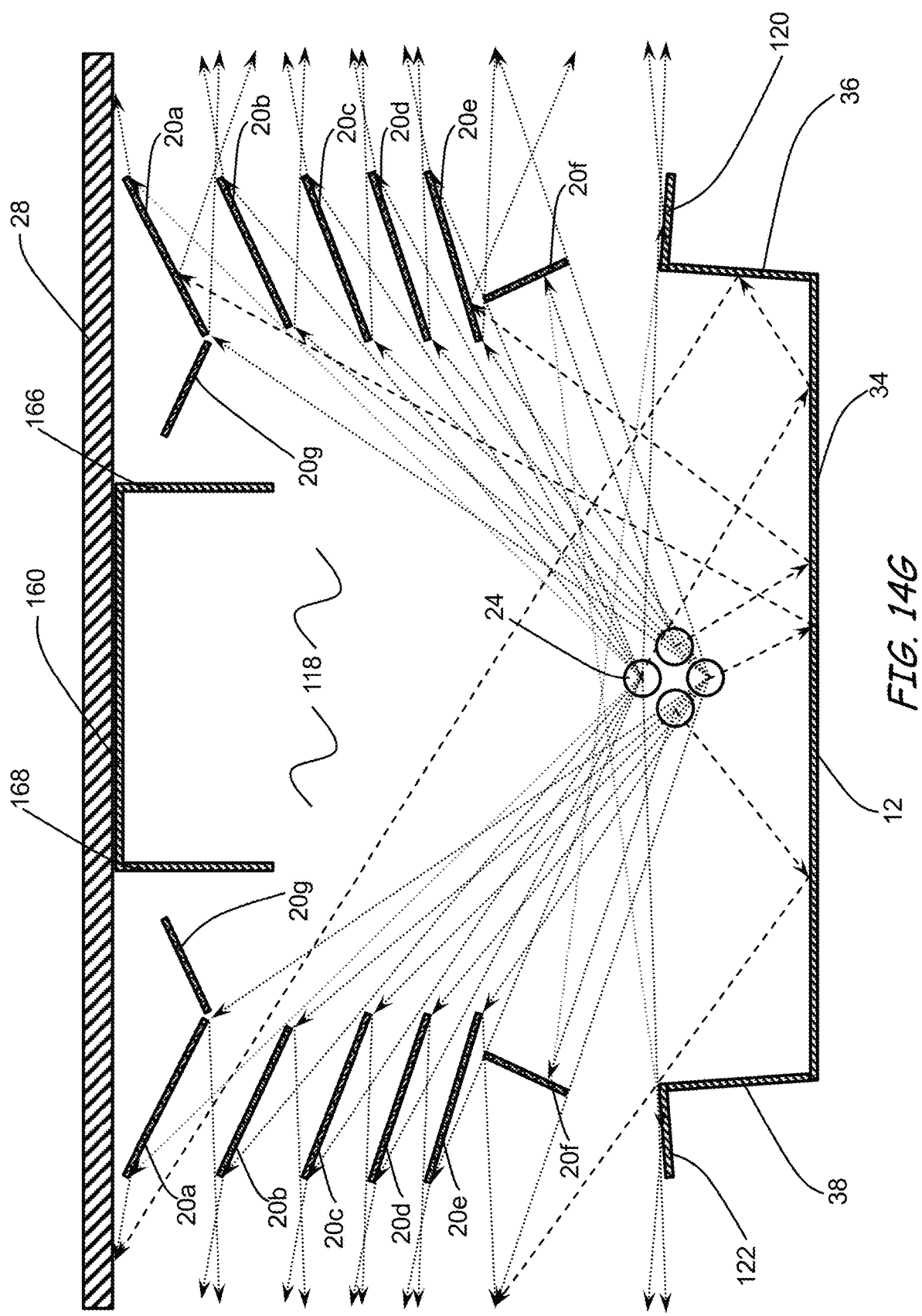
Figure 14H:
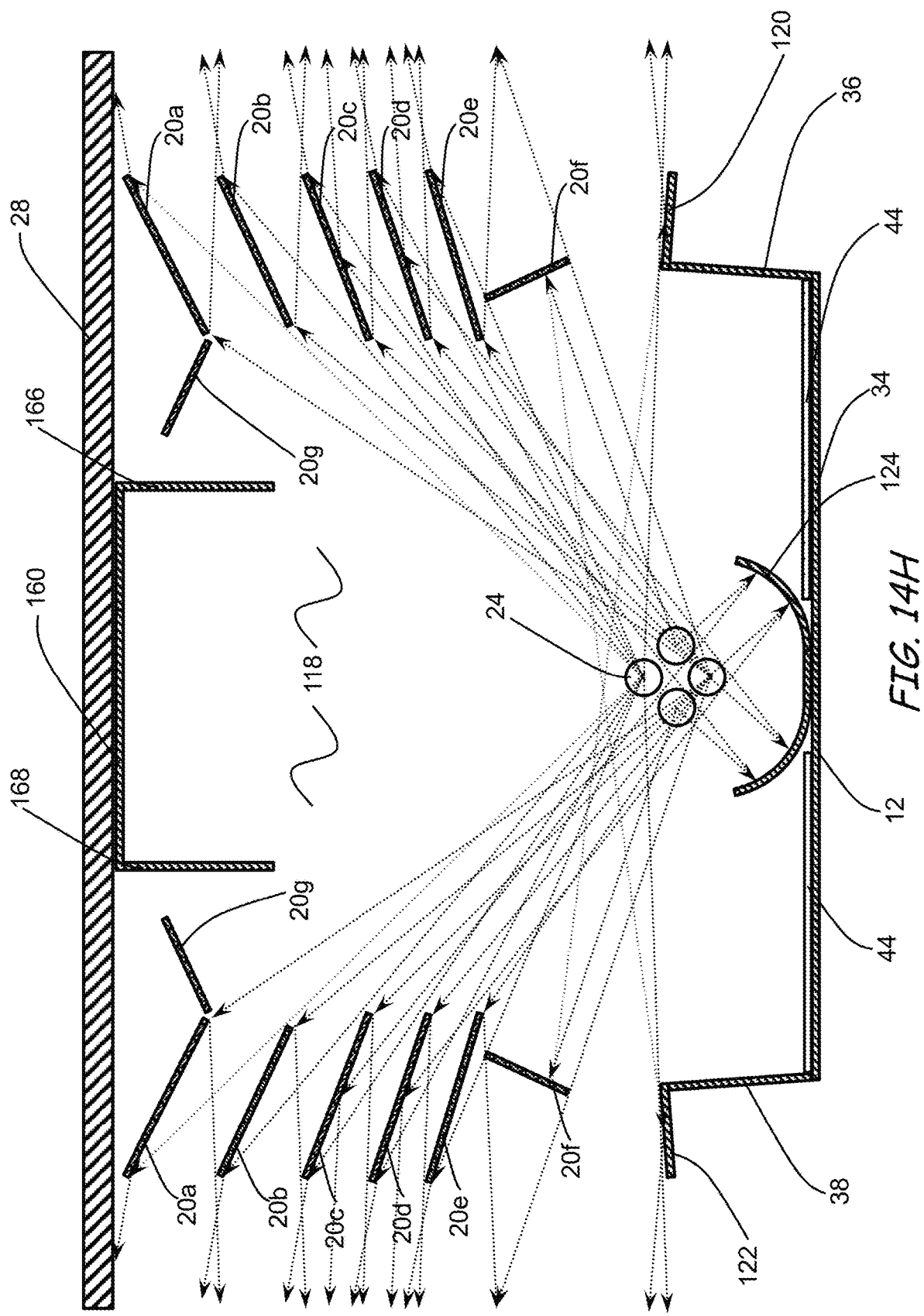
FIGS. 14H-14J are cross-sectional views of the ultraviolet light disinfection fixture according to another embodiment of the present invention illustrating the reflectance of ultraviolet light within the fixture and exiting the fixture.

According to another embodiment of the present invention, FIGS. 5B, 5C and 14H-14J illustrate the addition of a bottom reflective arc 124 and a top reflective arc 126 to fixture 10. FIG. 14H depicts bottom reflective arc 124 secured to base plate 34 of tray 12 at approximately the center of base plate 34. Bottom reflective arc 124 extends approximately the length of the glass cylinders of bulb 24 in fixture 10. Absorption pad 44 is split into two pieces to enable bottom arc 124 to interface with base plate 34. Bottom reflective arc 124 is curved at approximately 180 degrees to create the arc and may be fabricated from polished aluminum with a mirrored interior surface finish to maximize reflectance. Bottom reflective arc 124 will increase the ultraviolet-C light radiation of fixture 10 by approximately 40%. Ultraviolet-C light radiation that extends downward from bulb 24 will now be reflected upward from base plate 34 off reflective arc 124 and will not be absorbed by pad 44, thereby increasing the amount of ultraviolet-C light radiation produced by fixture 10.

Figure 14I:
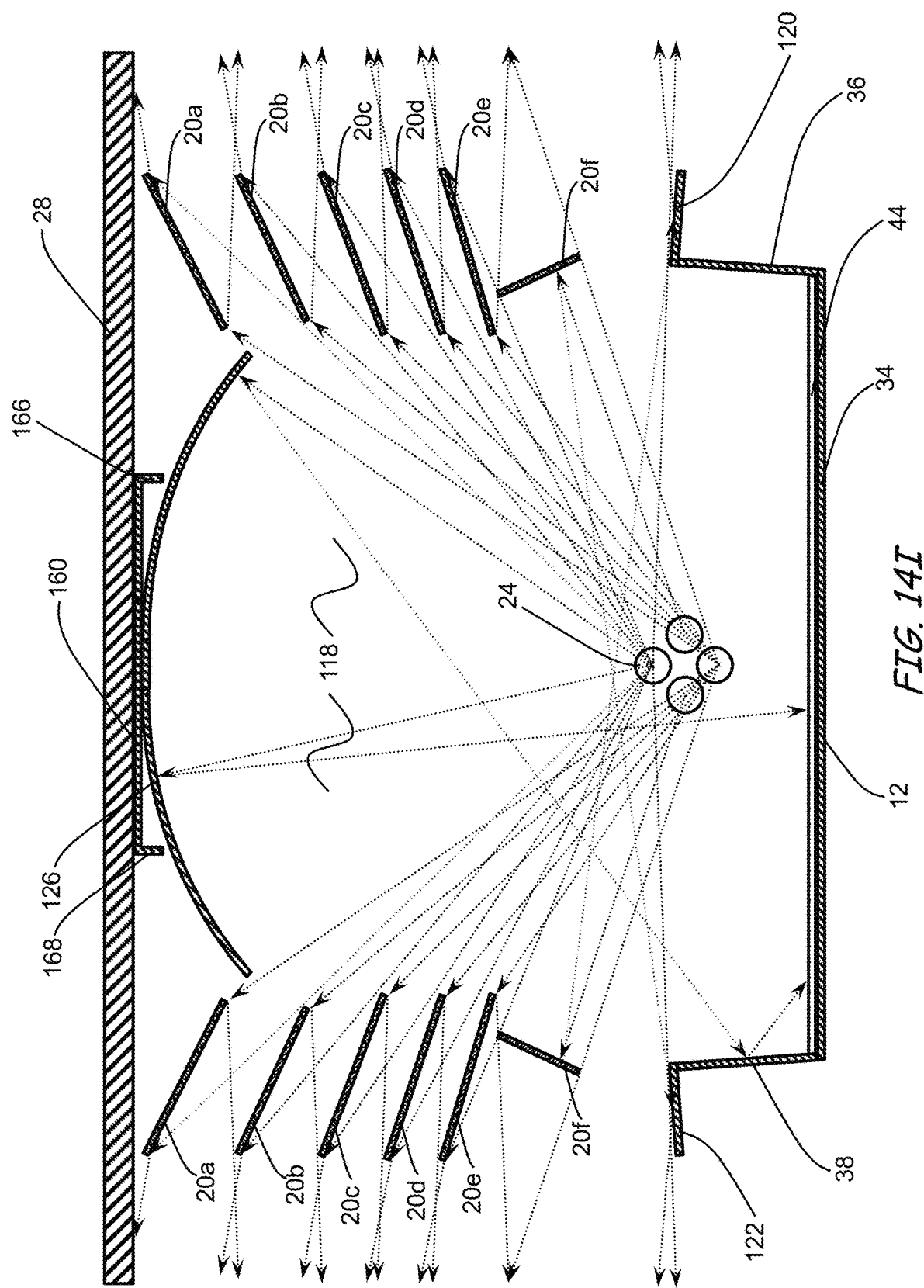

FIG. 14I depicts top reflective arc 126 secured to top plate 160 at approximately the center of top plate 160. Top reflective arc 126 extends approximately the length of the glass cylinders of bulb 24 in fixture 10. Top reflective arc 126 is curved at approximately 74 degrees to create the arc and may be fabricated from polished aluminum with a mirrored interior surface finish to maximize reflectance. Top reflective arc 126 will increase the ultraviolet-C light radiation of fixture 10 by approximately 20%. Top reflective arc 126 enables the removal of louver 20*g* from each of the two louver assemblies 88 of fixture 10. Edges 166, 168 of top plate 160 may also be shortened to enable clearance for top reflective arc 126. The smooth surface of top reflective arc 126 enables the removal of the corners of top plate 160 thereby improving the reflectance of the top of fixture 10. Ultraviolet-C light radiation that extends upward from bulb 24 will now be reflected downward from top plate 160 off reflective arc 126, thereby increasing the amount of ultraviolet-C light radiation produced by fixture 10.

Figure 5A:
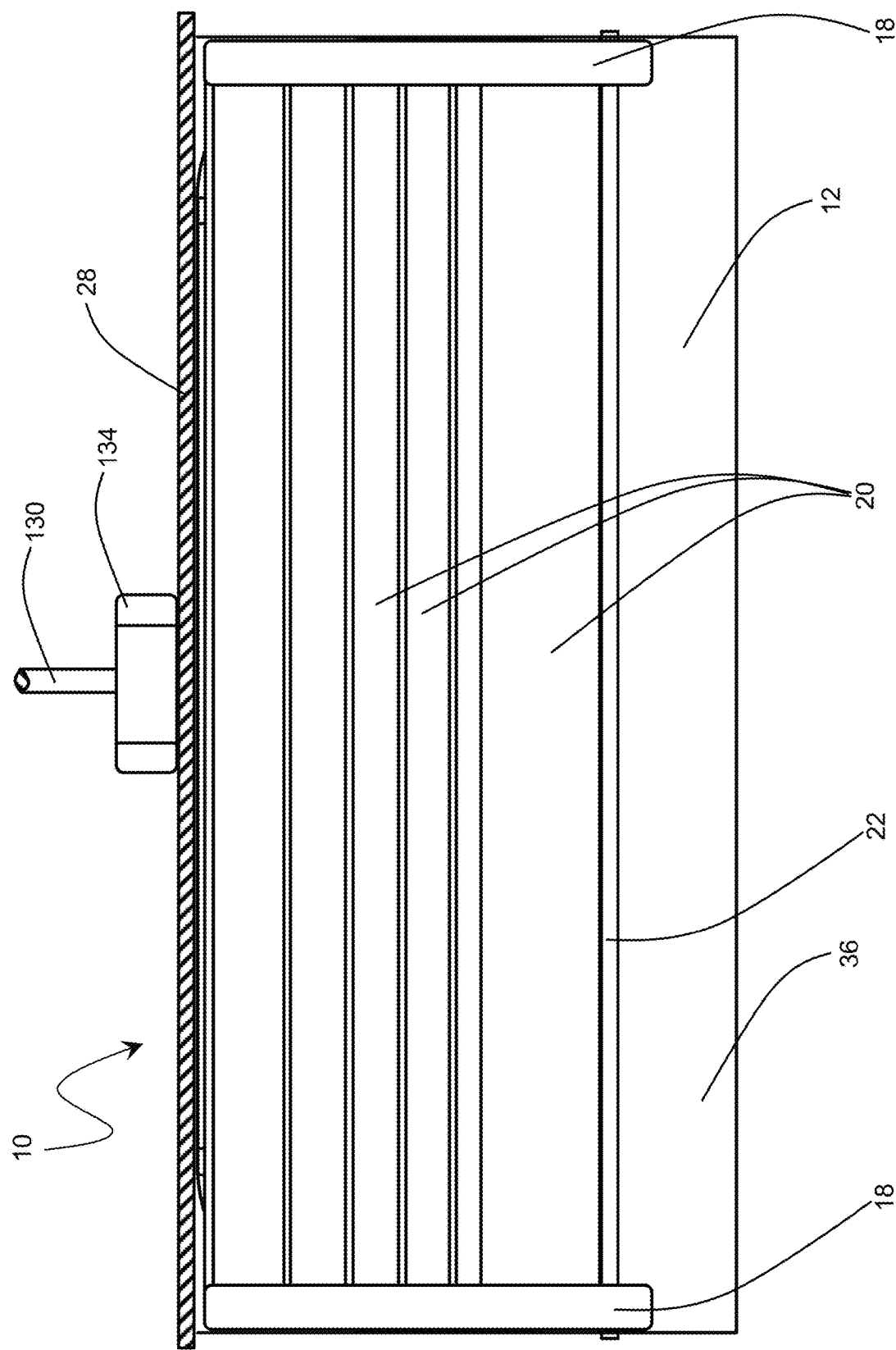
FIG. 5A is a front view of the ultraviolet light disinfection fixture according to the embodiment of the present invention.
Figure 5B:
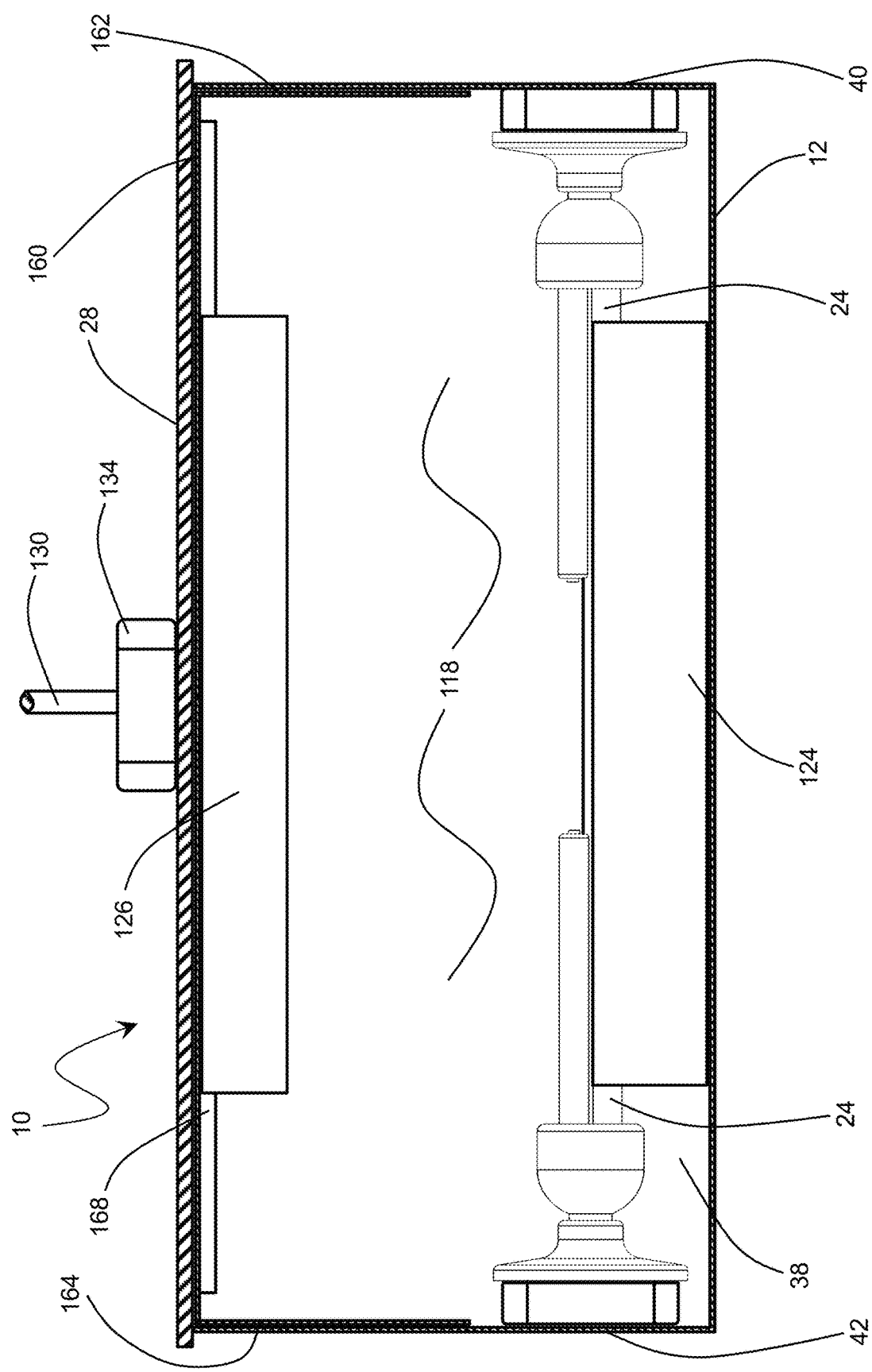
FIG. 5B is a front cross-sectional view of the ultraviolet light disinfection fixture according to another embodiment of the present invention depicting a bottom reflective arc and a top reflective arc.
Figure 5C:
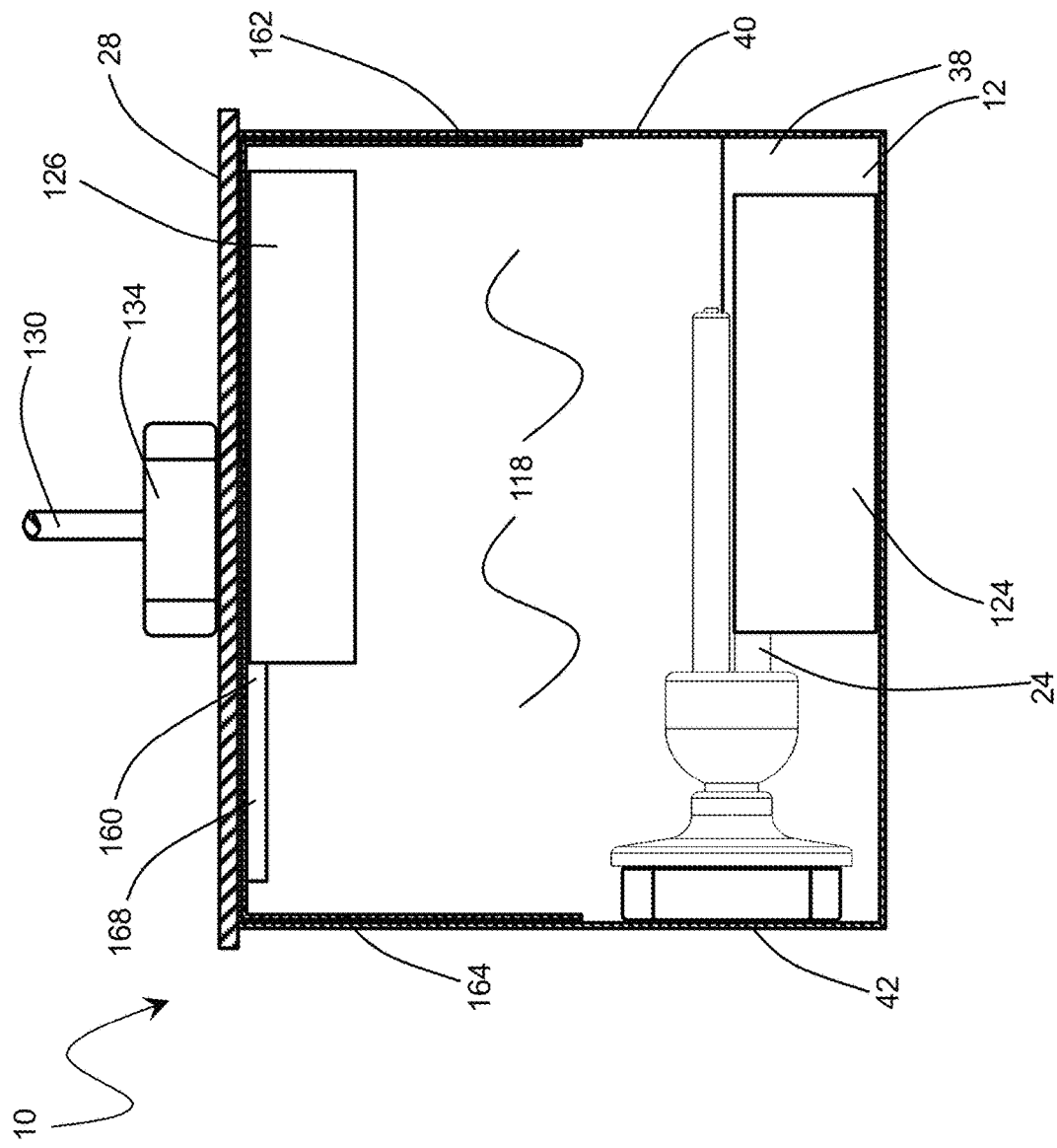
FIG. 5C is a front cross-sectional view of the ultraviolet light disinfection fixture according to yet another embodiment of the present invention depicting a single bulb ultraviolet light disinfection fixture.
Figure 5D:
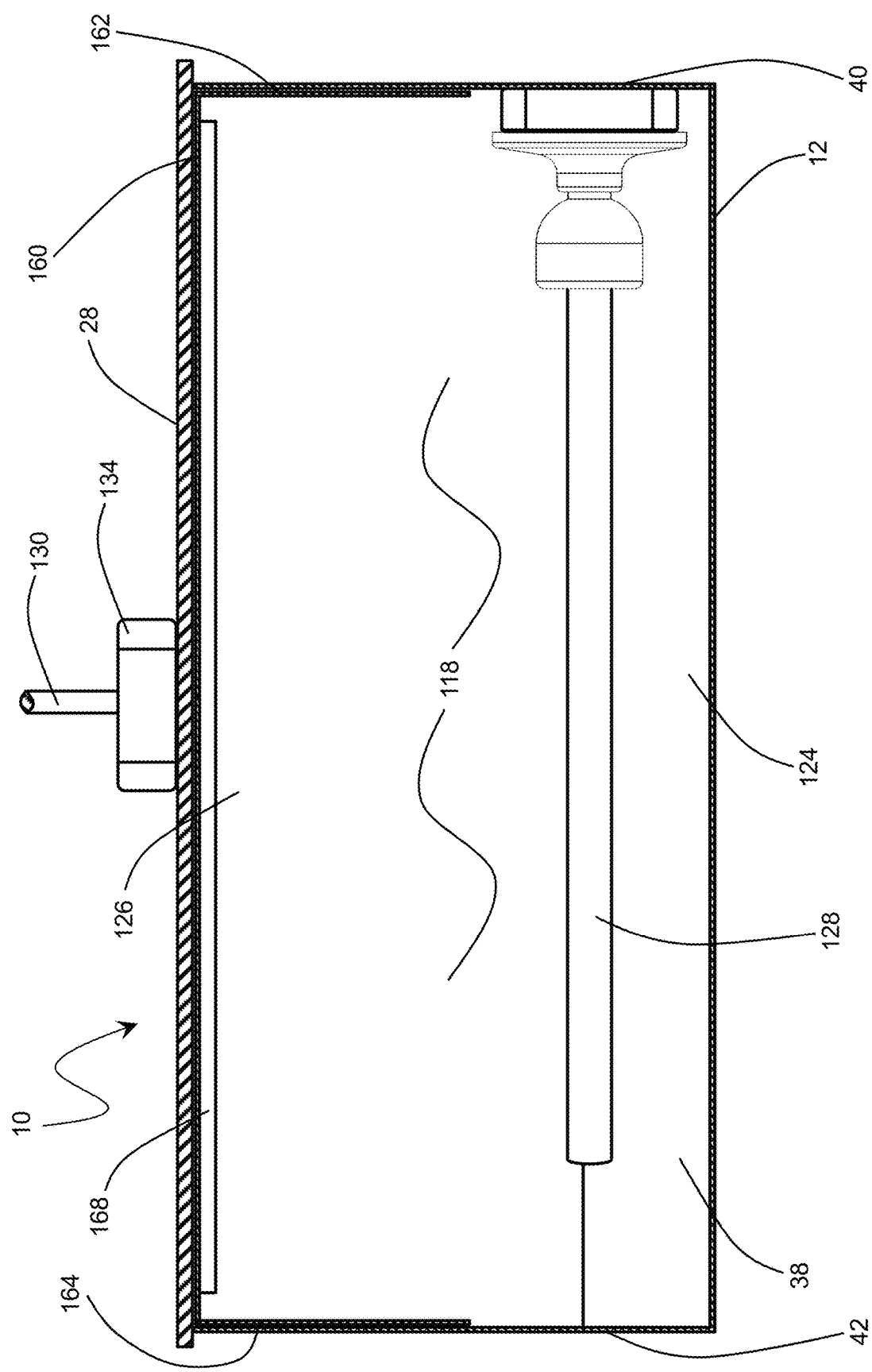
FIG. 5D is a front cross-sectional view of the ultraviolet light disinfection fixture according to still another embodiment of the present invention depicting an ultraviolet-C light radiation fluorescent tube.
Figure 6:
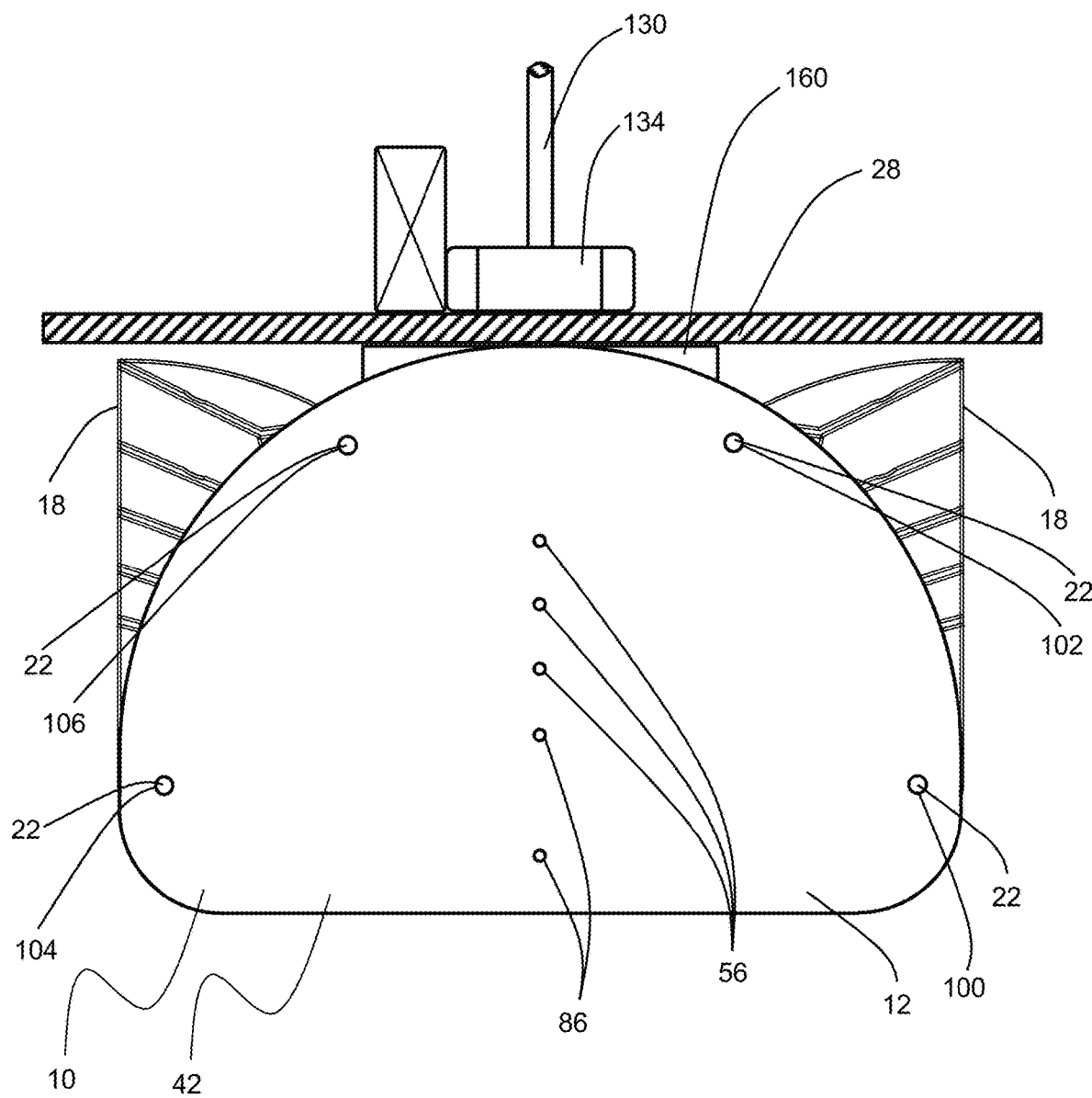
FIG. 6 is a side view of the ultraviolet light disinfection fixture according to the embodiment of the present invention.
Figure 7:
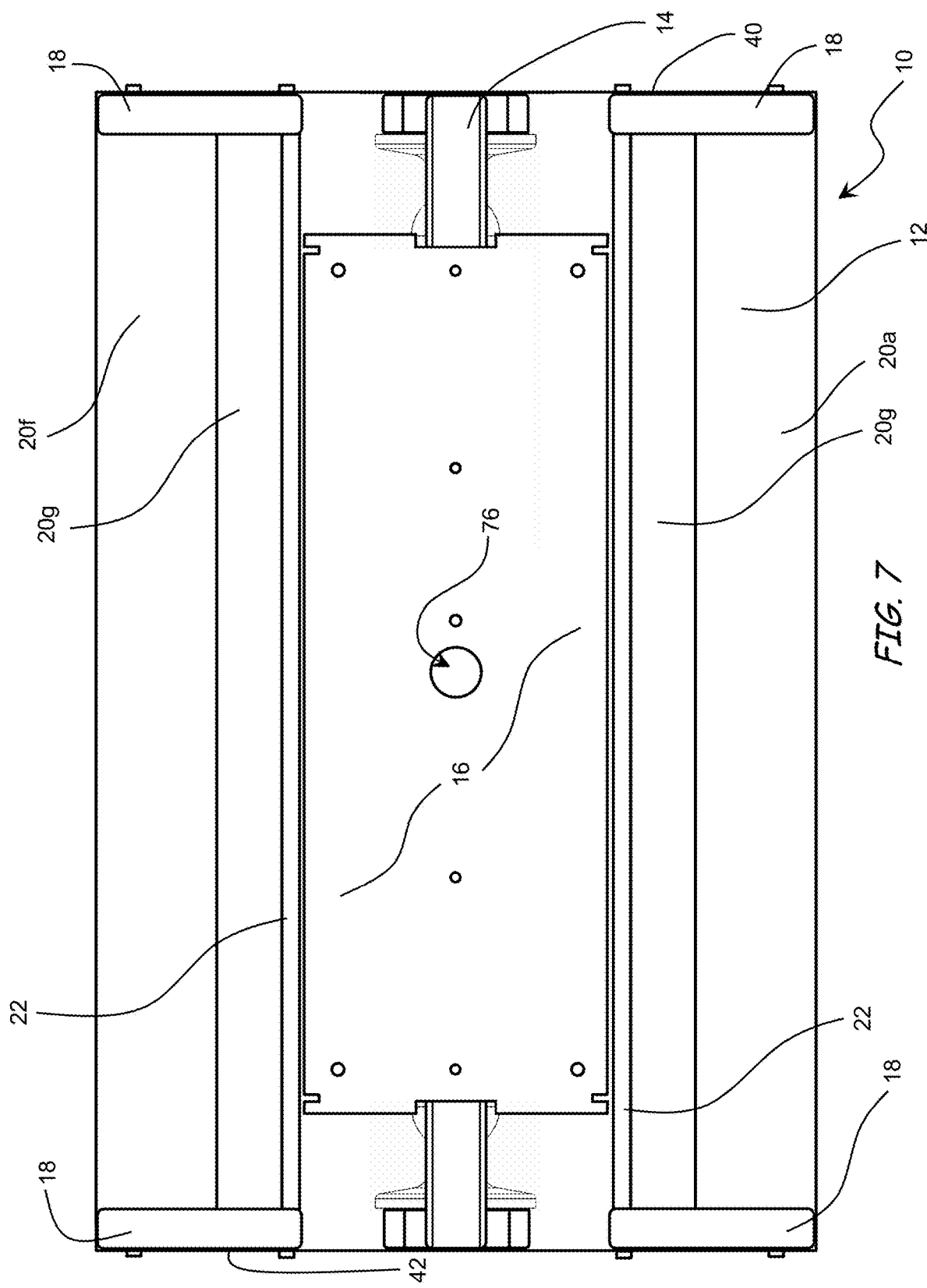
FIG. 7 is a top view of the ultraviolet light disinfection fixture of FIG. 2 according to the embodiment of the present invention.
Figure 8:
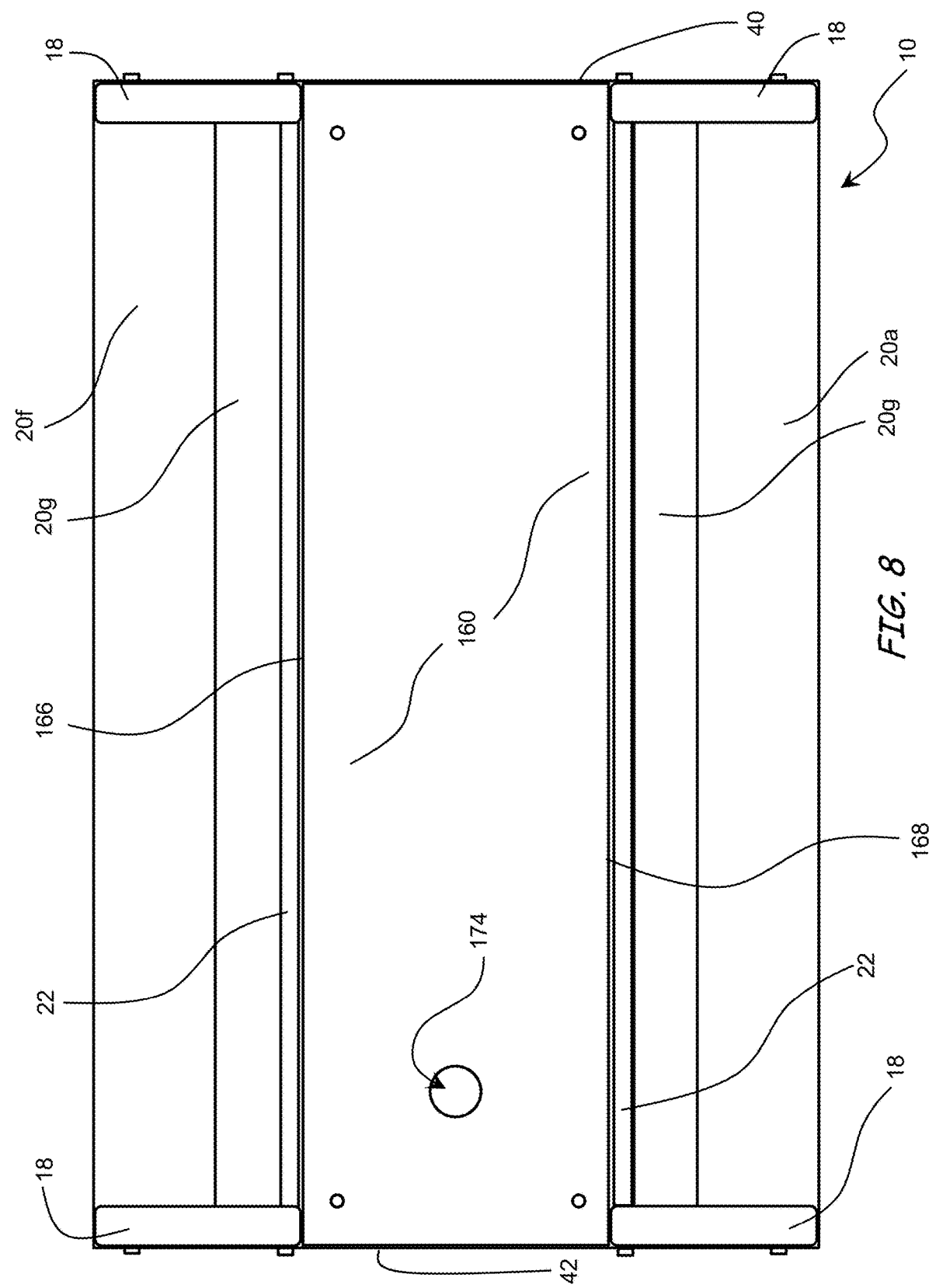
FIG. 8 is a top view of the ultraviolet light disinfection fixture of FIG. 3 according to the embodiment of the present invention.
Figure 9:
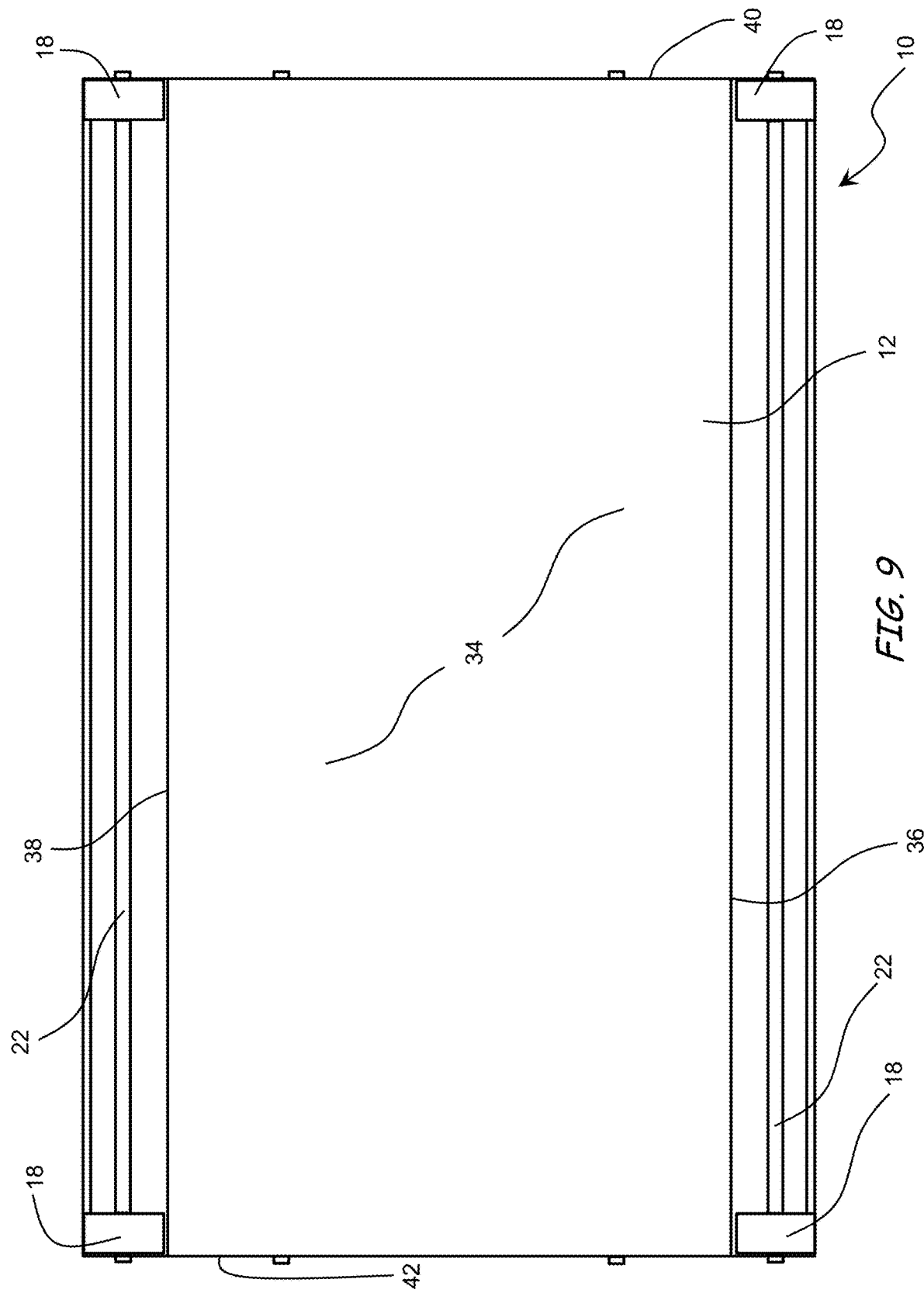
FIG. 9 is a bottom view of the ultraviolet light disinfection fixture according to the embodiment of the present invention.
Figures 10A, 10B:
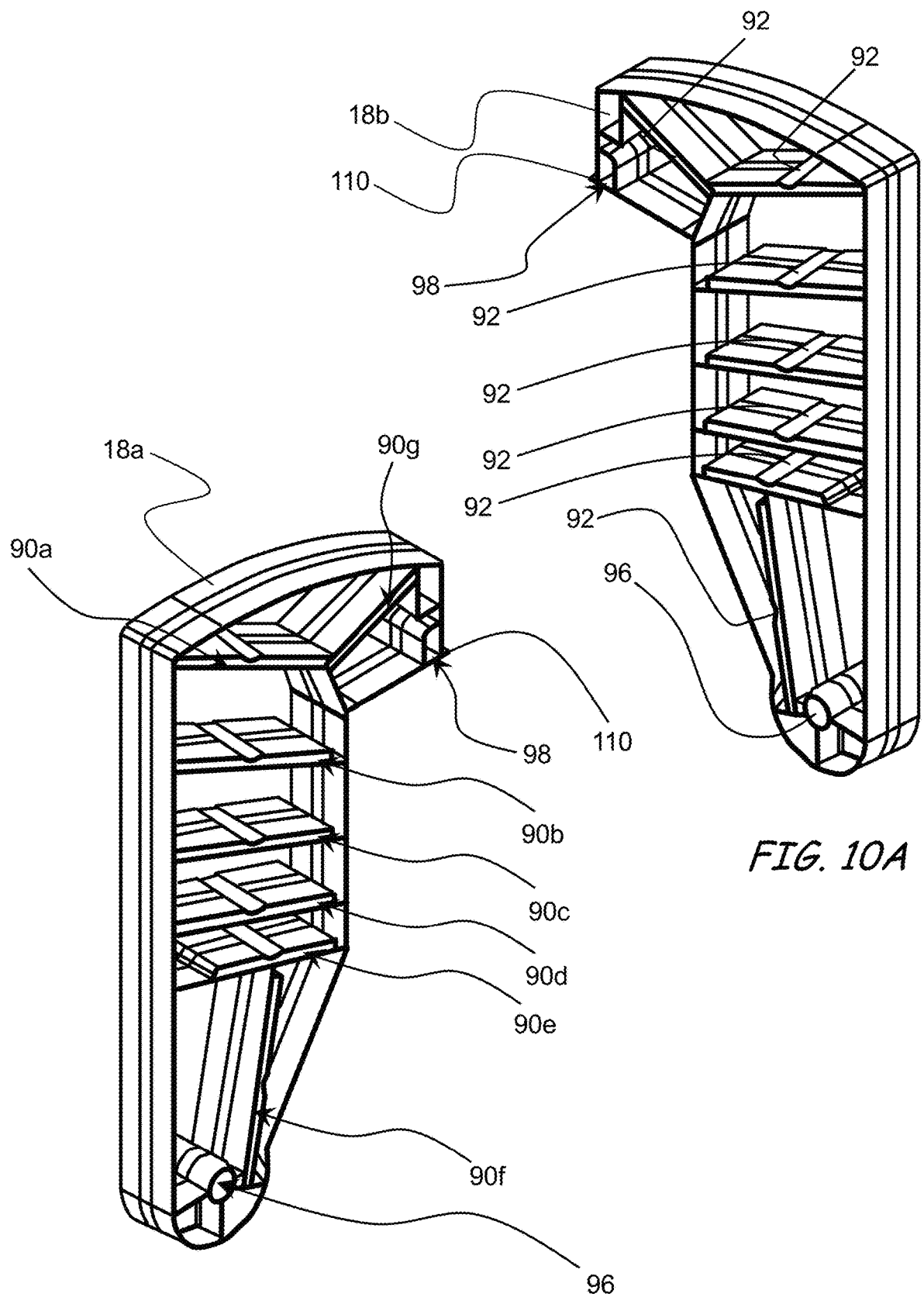
FIGS. 10A and 10B are isometric views louver supports of the ultraviolet light disinfection fixture according to the embodiment of the present invention.
Figure 10C:
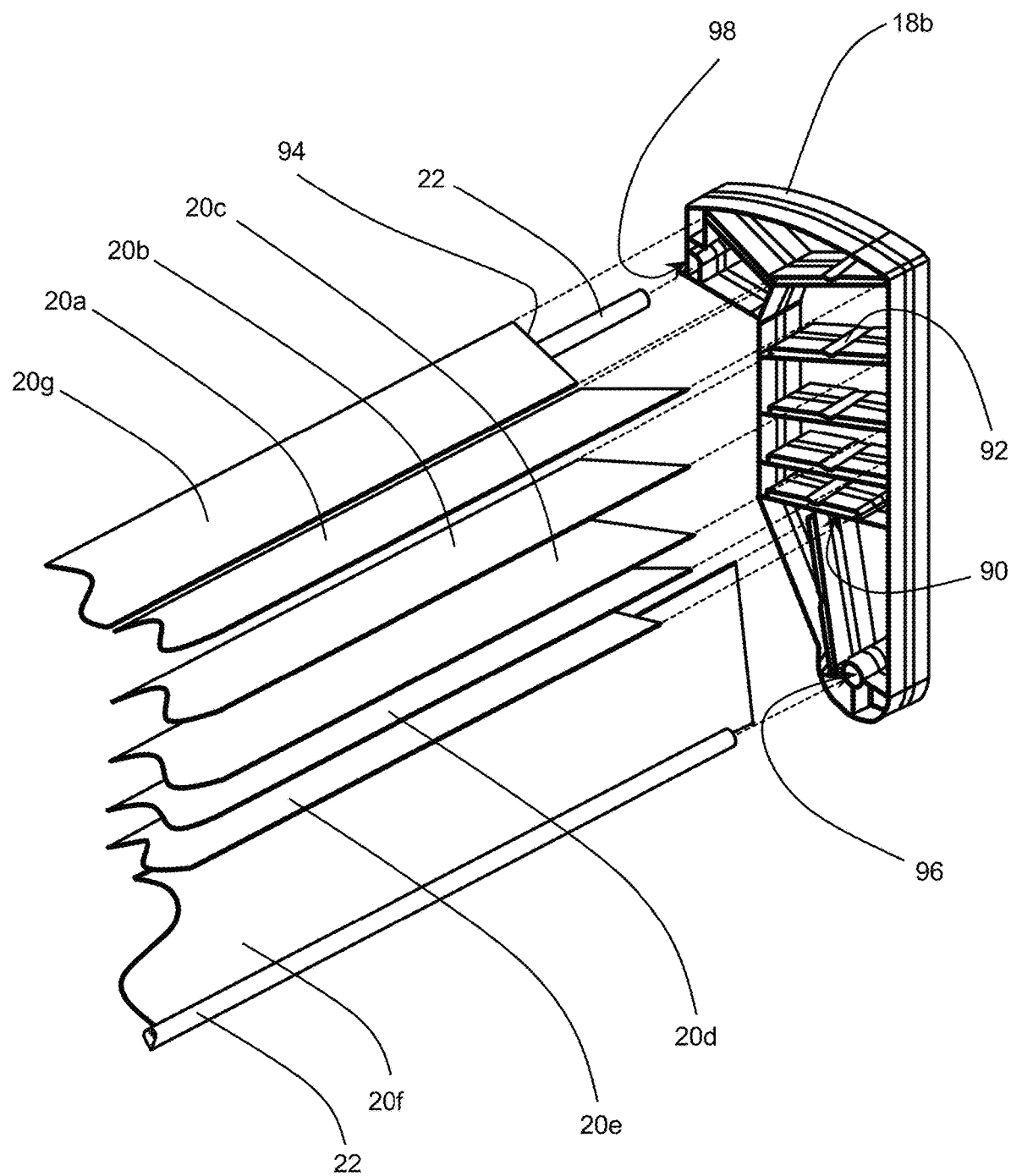
FIGS. 10C-10F are isometric views of the louver supports, ultraviolet-C light radiation reflective louvers and rods of the ultraviolet light disinfection fixture according to the embodiment of the present invention.
Figure 10D:
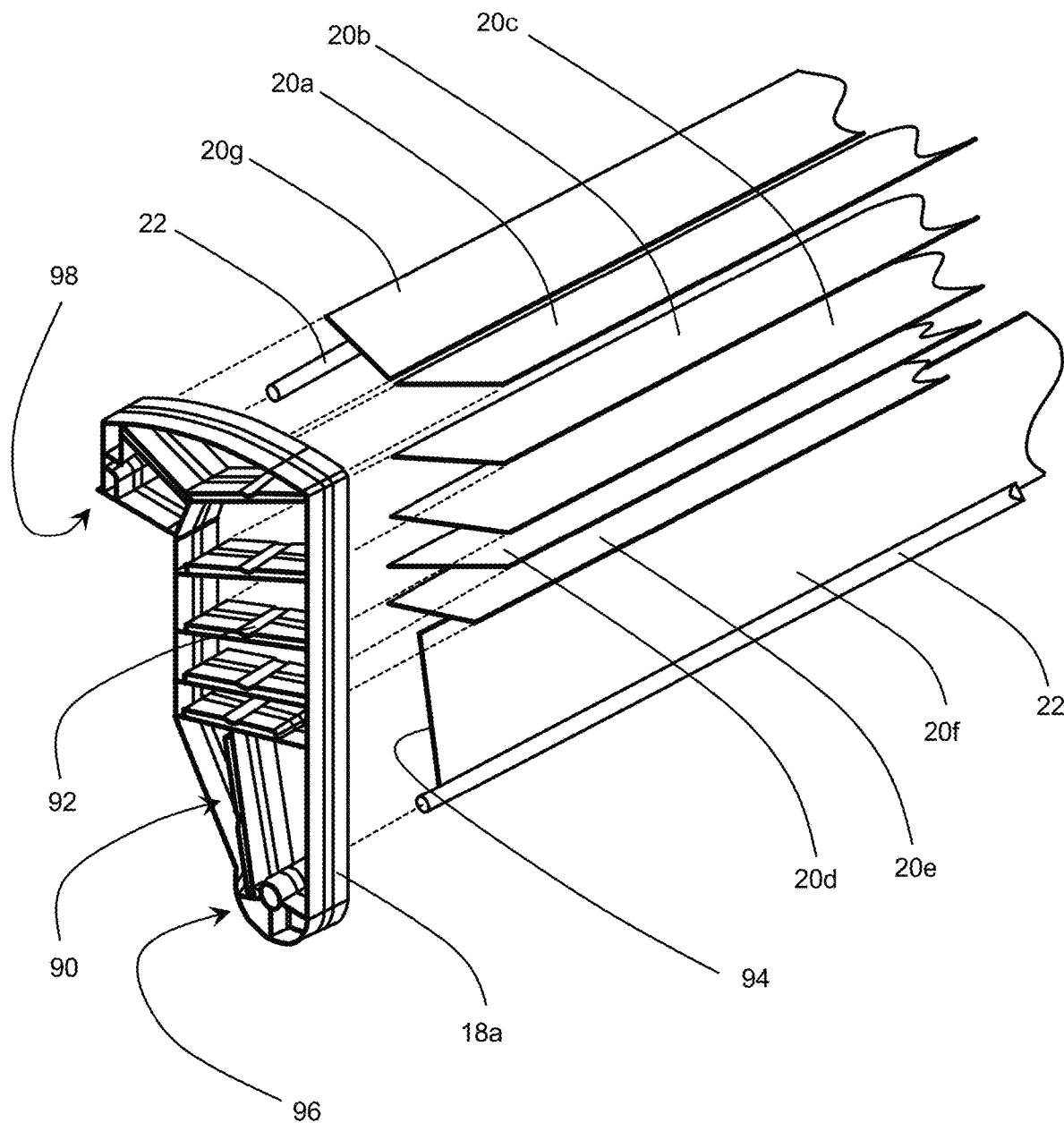
Figure 10E:
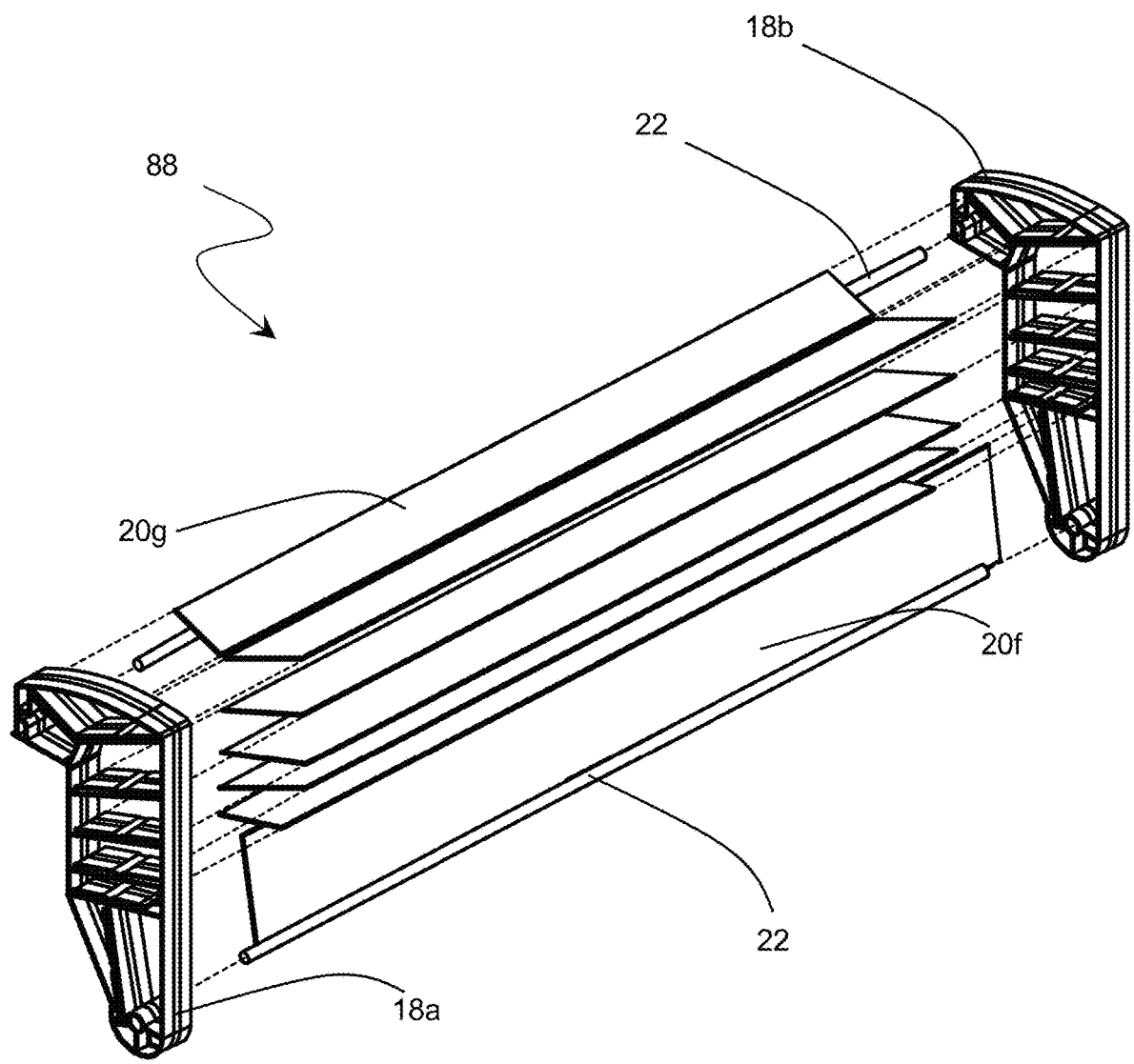
Figure 10F:
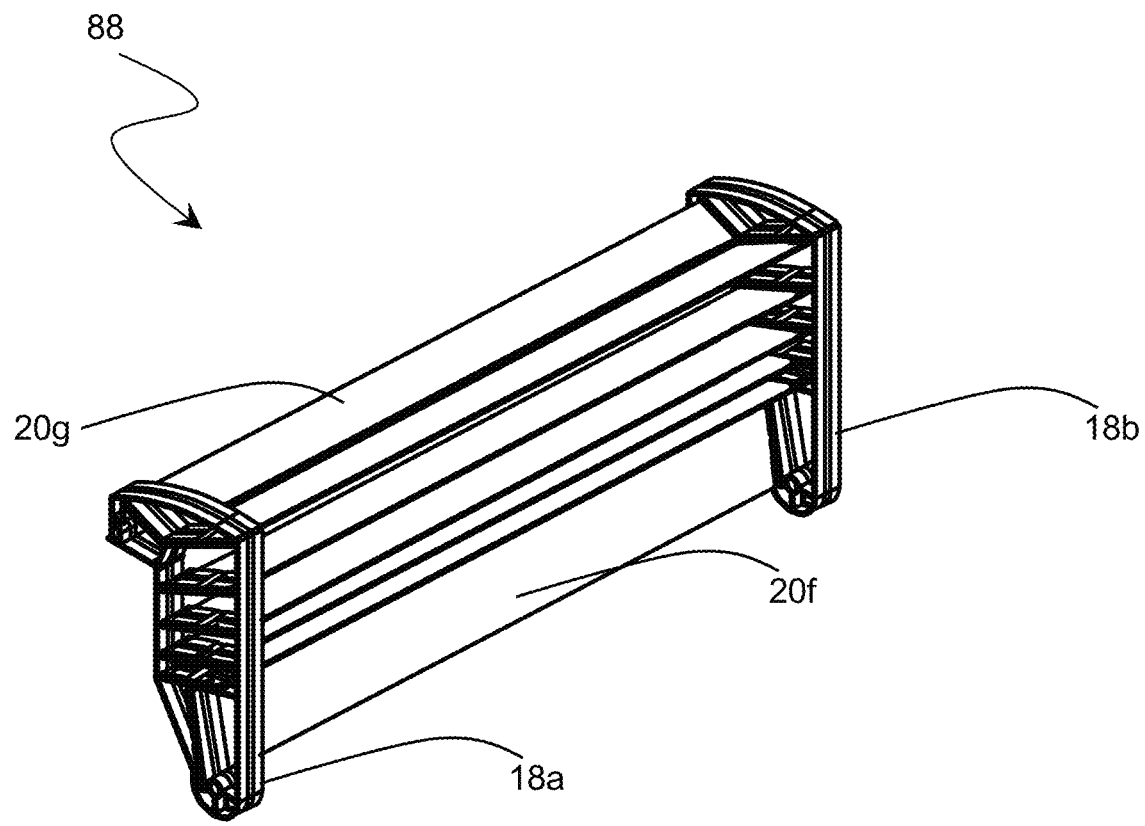
Figure 11A:
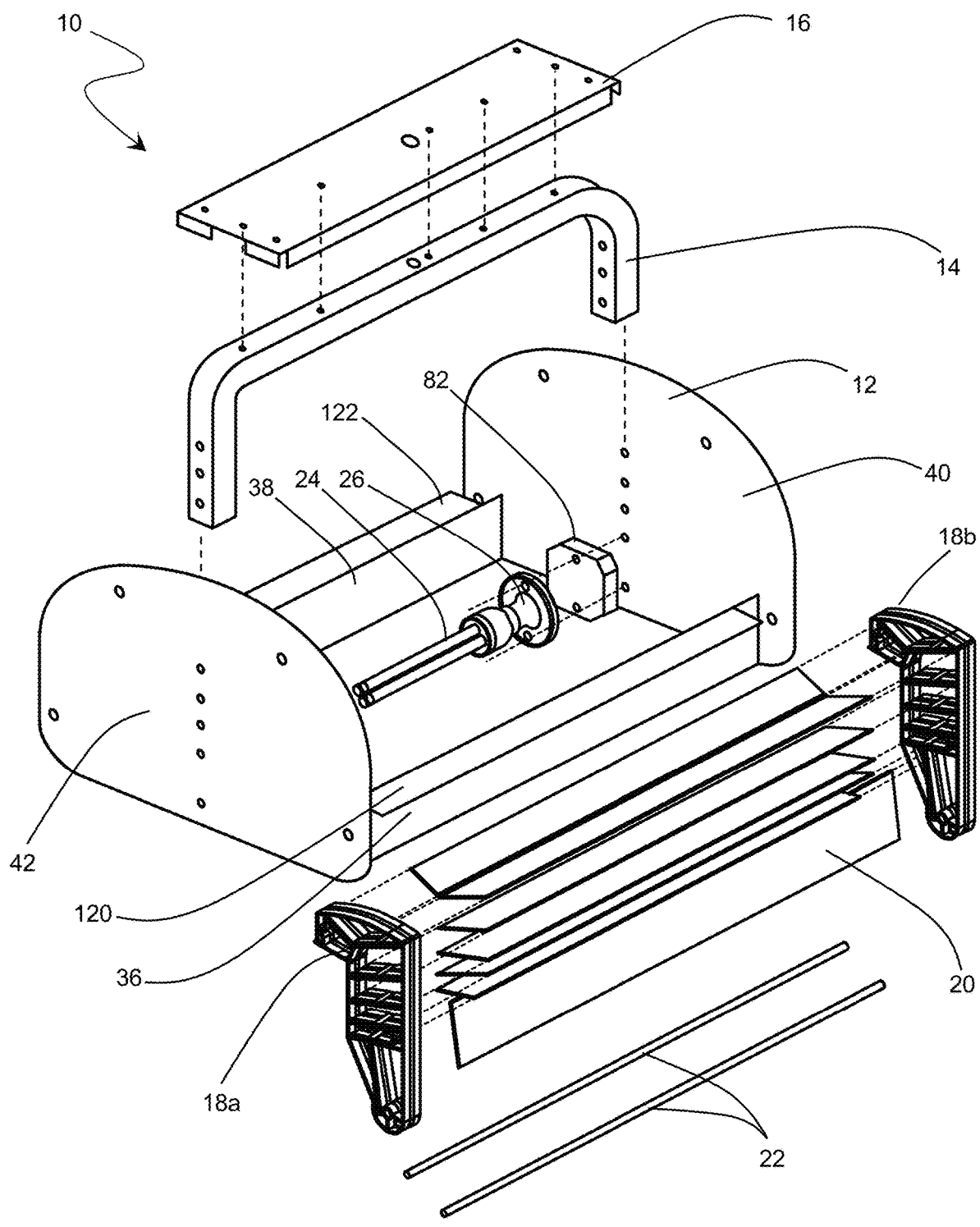
FIGS. 11A-11F are exploded views of the components of the ultraviolet light disinfection fixture of FIG. 2 according to the embodiment of the present invention.
Figure 11B:
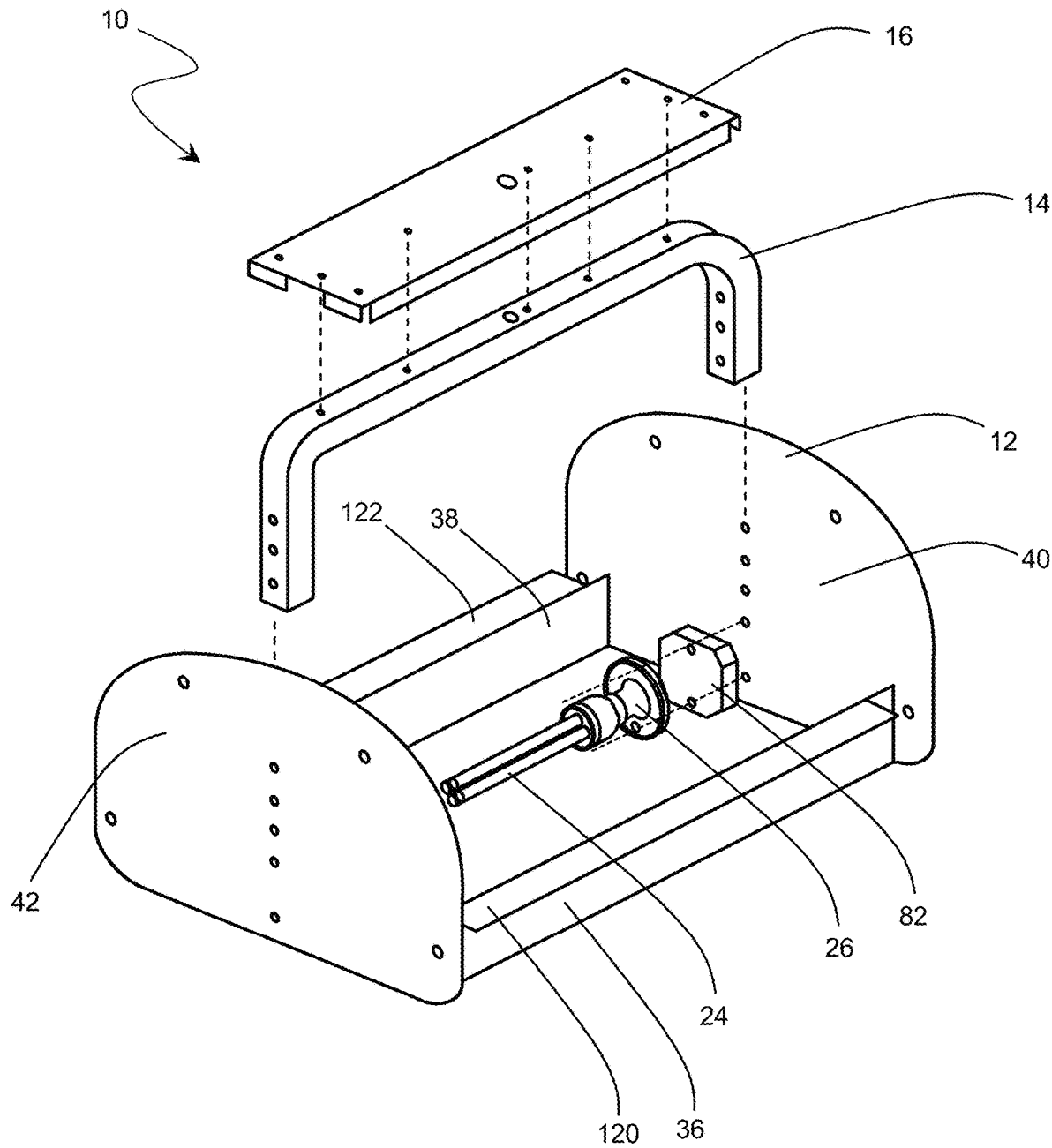
Figure 11C:
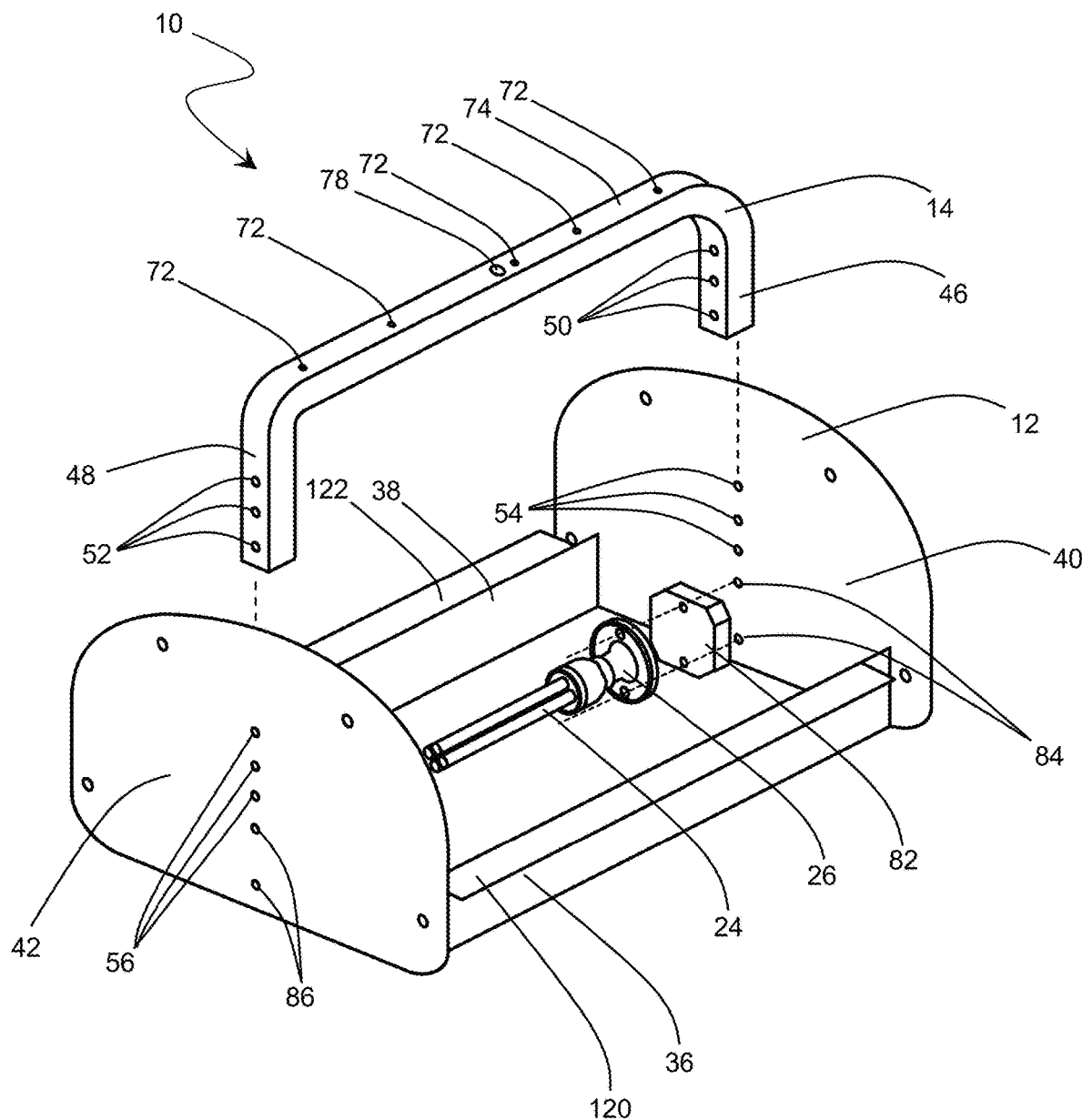
Figure 11D:
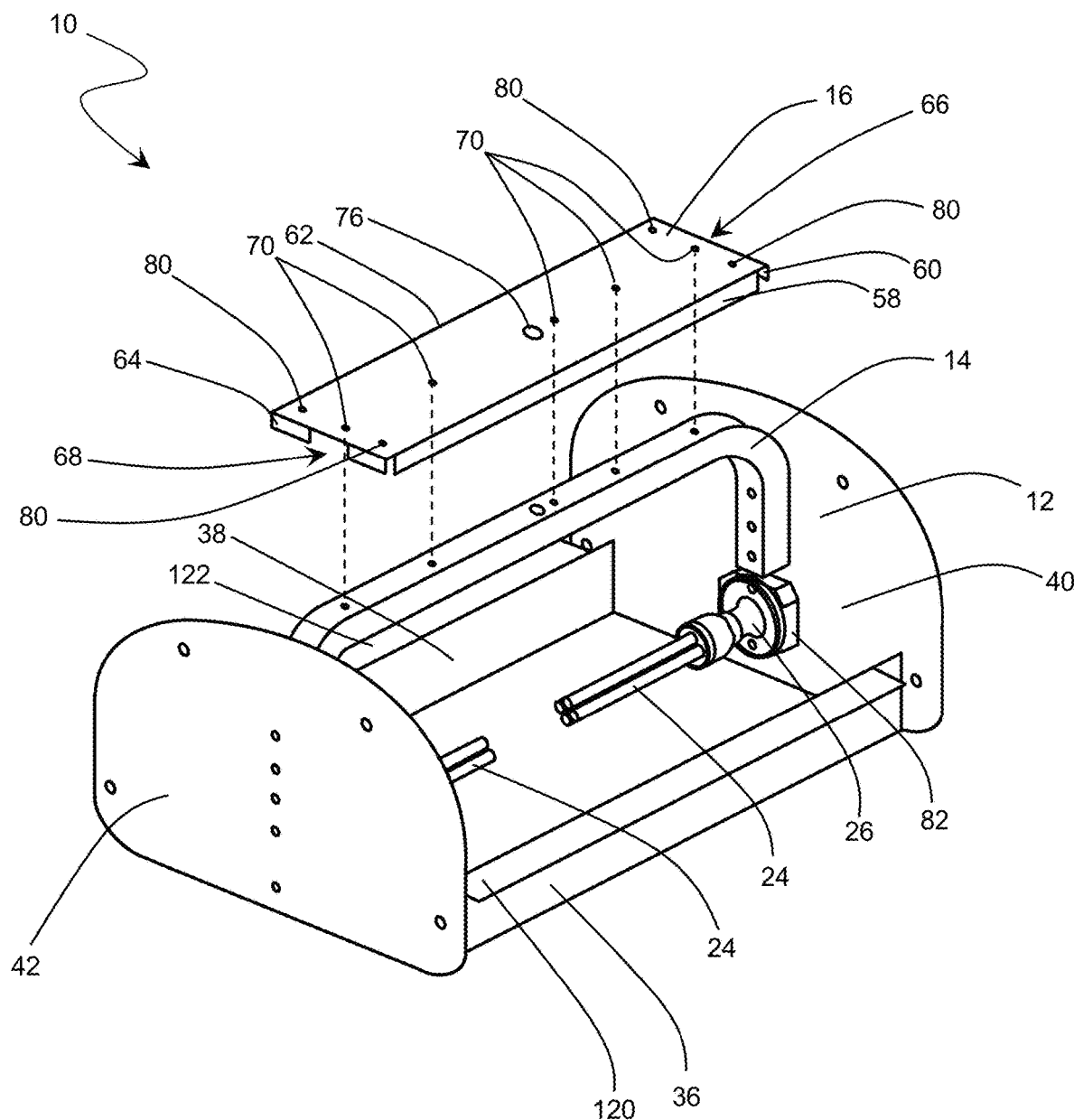
Figure 11E:
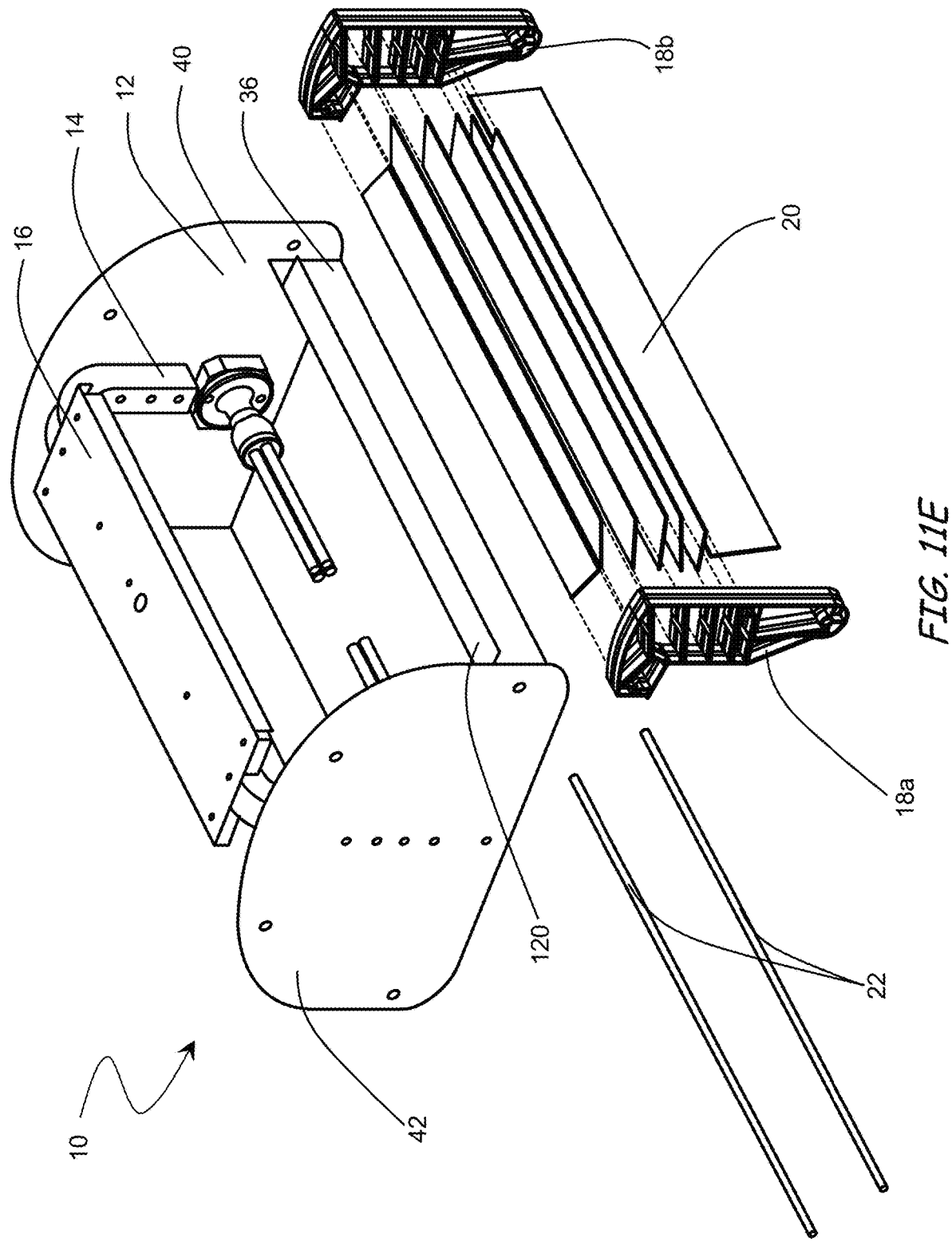
Figure 11F:
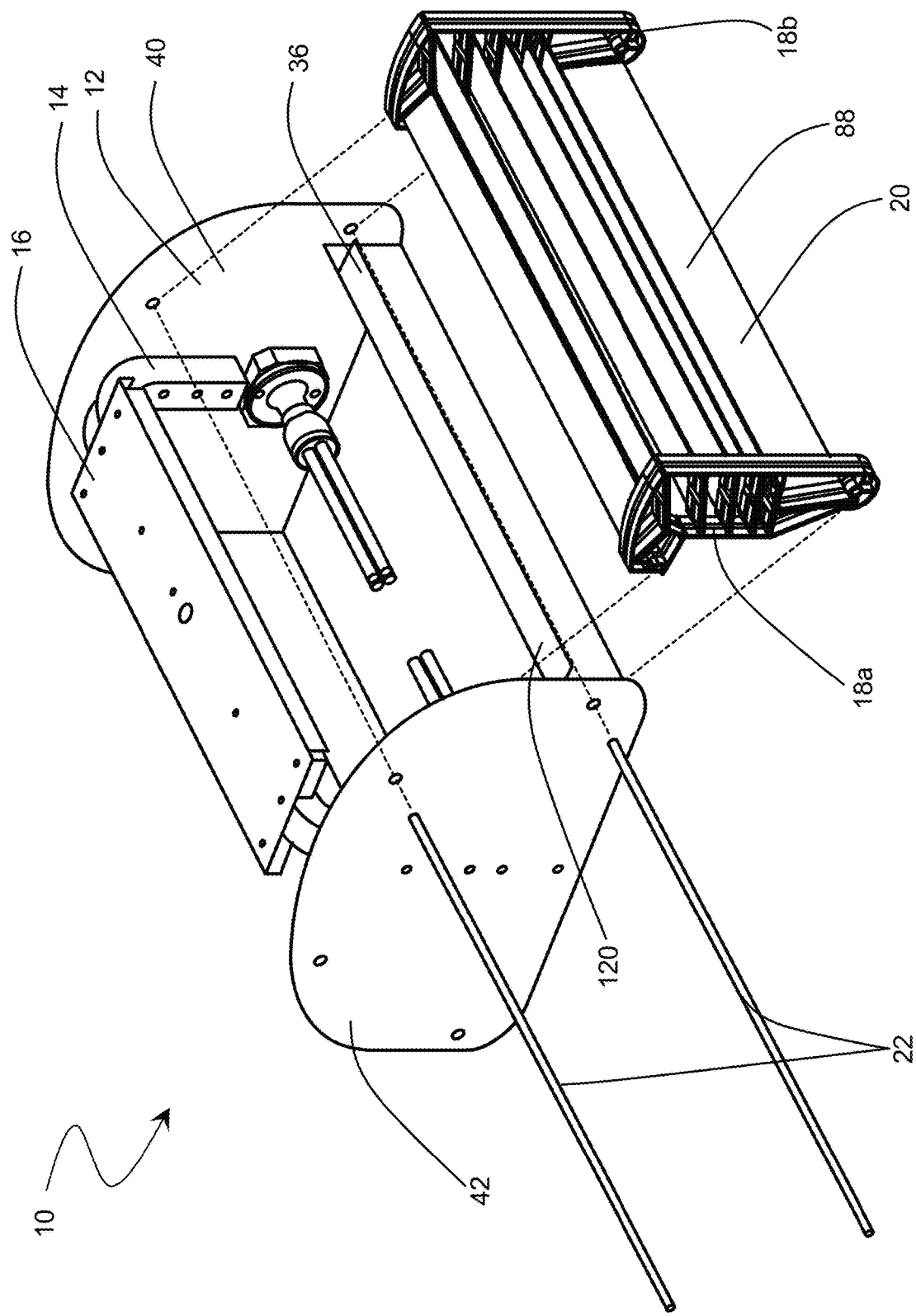
Figure 14J:
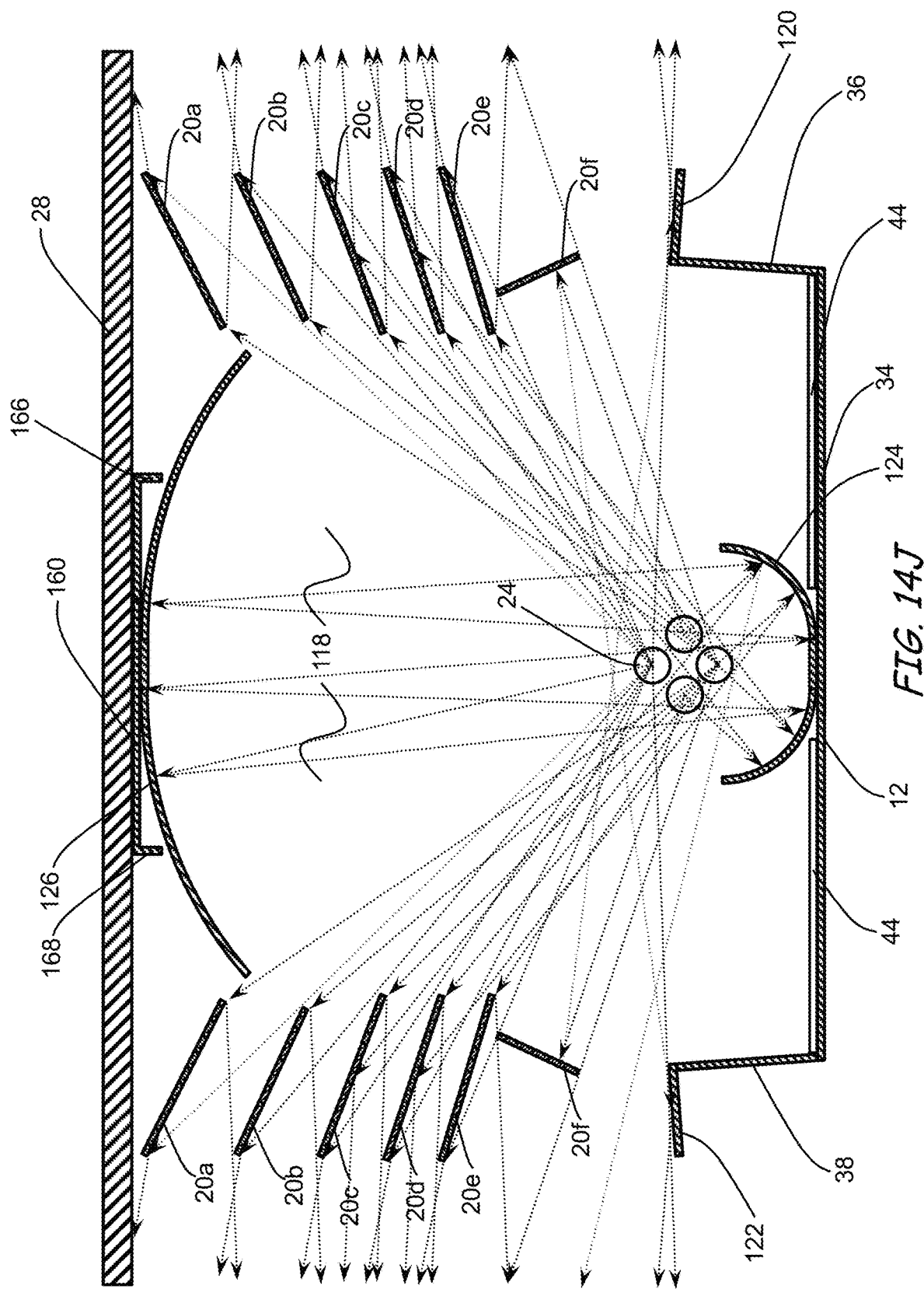

FIGS. 5B, 5C and 14J depict bottom reflective arc 124 secured to base plate 34 of tray 12 at approximately the center of base plate 34 and top reflective arc 126 secured to top plate 160 at approximately the center of top plate 160. Both reflective arcs 124, 126 may be used together with fixture 10 to increase the overall ultraviolet-C light radiation of fixture 10 by approximately 60%, thereby improving the overall efficiency of fixture 10.

Fixture 10 will provide the following advantages over the prior art references. Each of tray 12, tube 14, top plate 16 or top plate 160, louver mounts 18 and ultraviolet-C light radiation reflective louvers 20, dowel rods 22 are inexpensive to manufacture from inexpensive materials using inexpensive tooling and manufacturing means to produce each component and assemble the components to create fixture 10. Materials used in fixture 10 enable a smaller and lighter fixture that is less expensive than prior art units and may be adapted for many uses. Fixture 10 enables a wide range of flexibility to be used with a number of different sized and type of ultraviolet-C bulbs and in a variety of different areas or enclosures. The precision sizing and positioning of louvers 20 relative to each other louver 20, tray 12 and top plate 16 or top plate 160, ensure maximum ultraviolet-C light radiation and extension of a "kill zone" around the exterior of fixture 10 for the extermination of viruses, bacteria and pathogens while ensuring the safety of humans and animals from ultraviolet-C light radiation exposure when occupying a particular room or enclosure with an operational fixture 10.

Figure 17A:
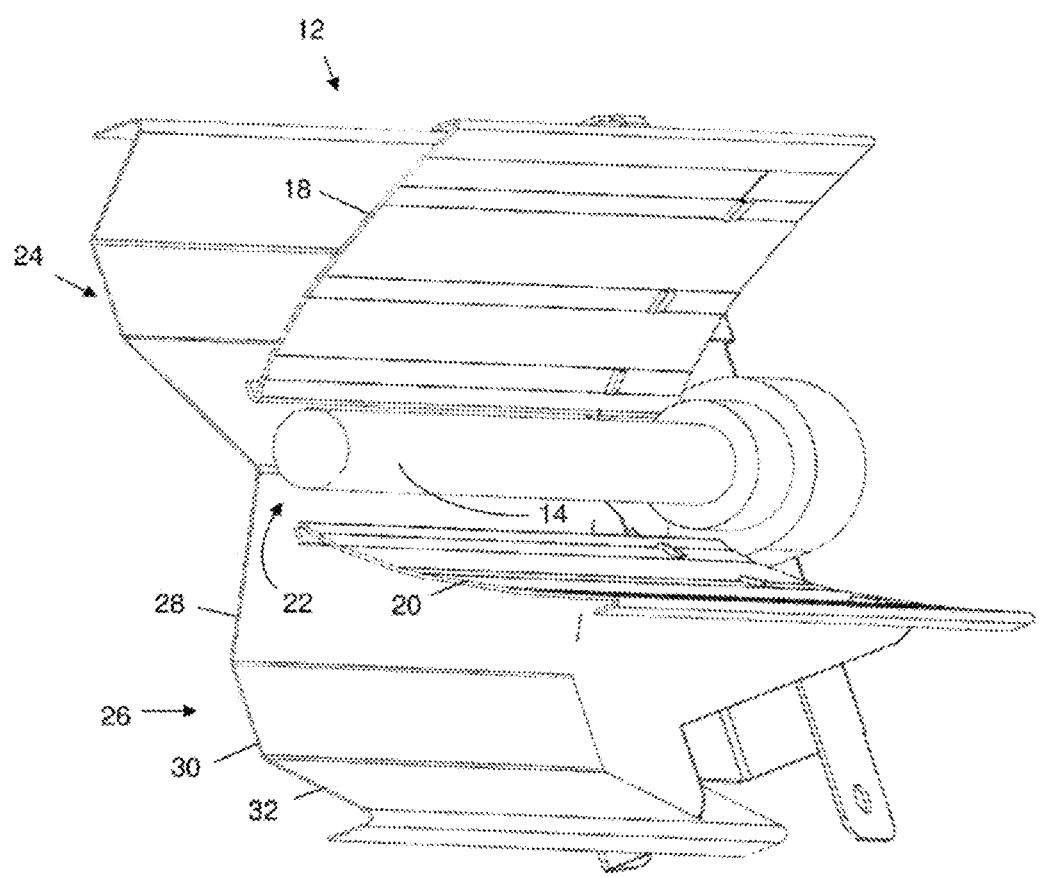
FIGS. 17A-17E are drawings from prior art references.
Figure 17B:
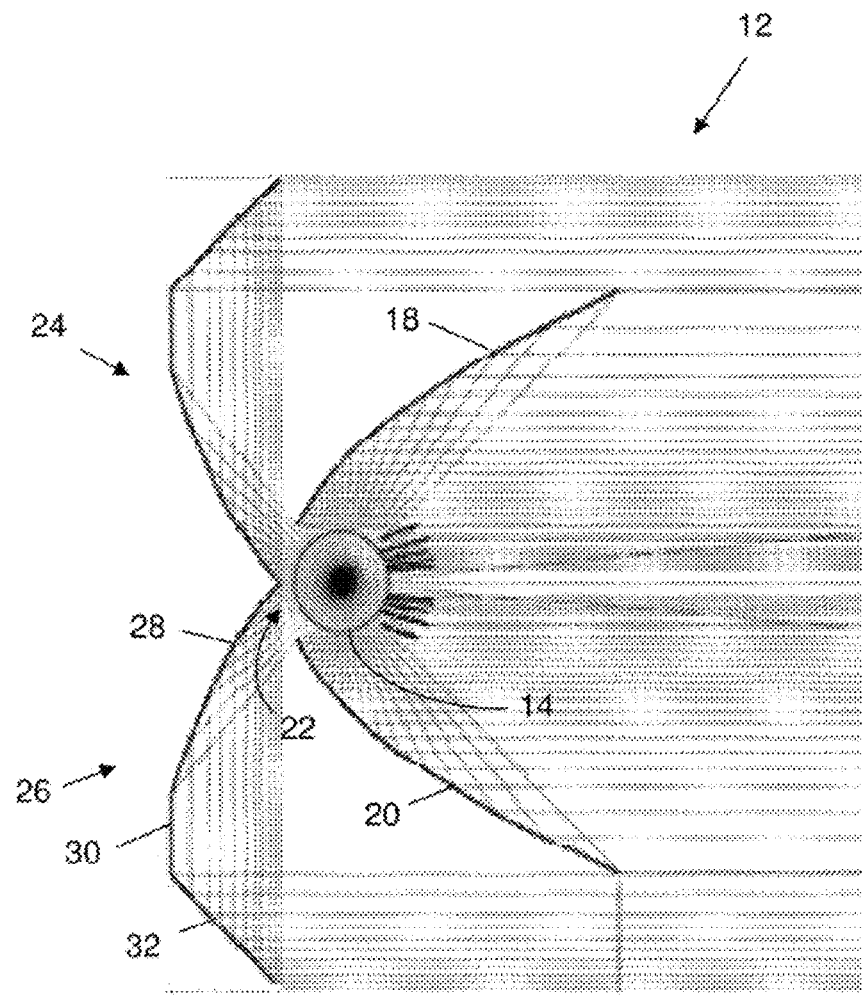
Figure 17C:
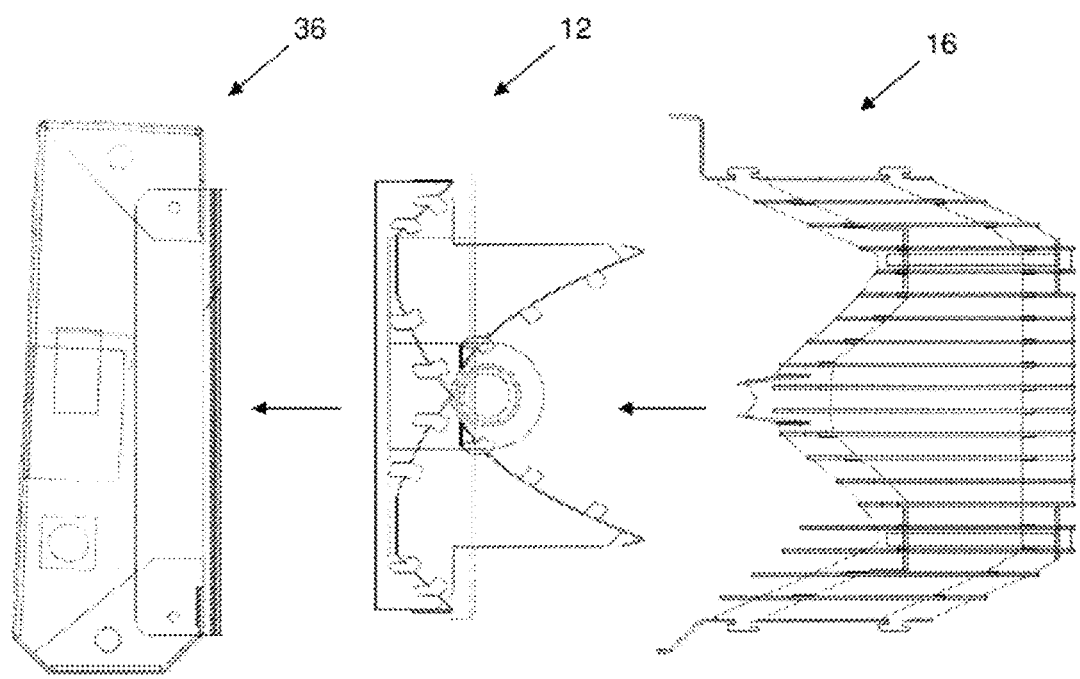

Elaborate parabolic reflectors are not required as they are in prior art ultraviolet-C lamps to facilitate ultraviolet-C light radiation outside of the lamp enclosure (see FIGS. 17A-17C; prior art from U.S. Pat. No. 8,921,893). Elaborate parabolic reflectors add expense to the prior art ultraviolet-C light radiation lamps. Further, 20 wide louvers are required with the '893 patent adding further complexity and expense. Fixture 10 may be configured for use with a number of different ceiling heights (see FIGS. 13A-13C) as well to ensure ample ultraviolet-C light radiation to sterilize the air while maintaining the safety of the individuals in the area while the ultraviolet-C light radiation lamp is in operation.

Figure 17D:
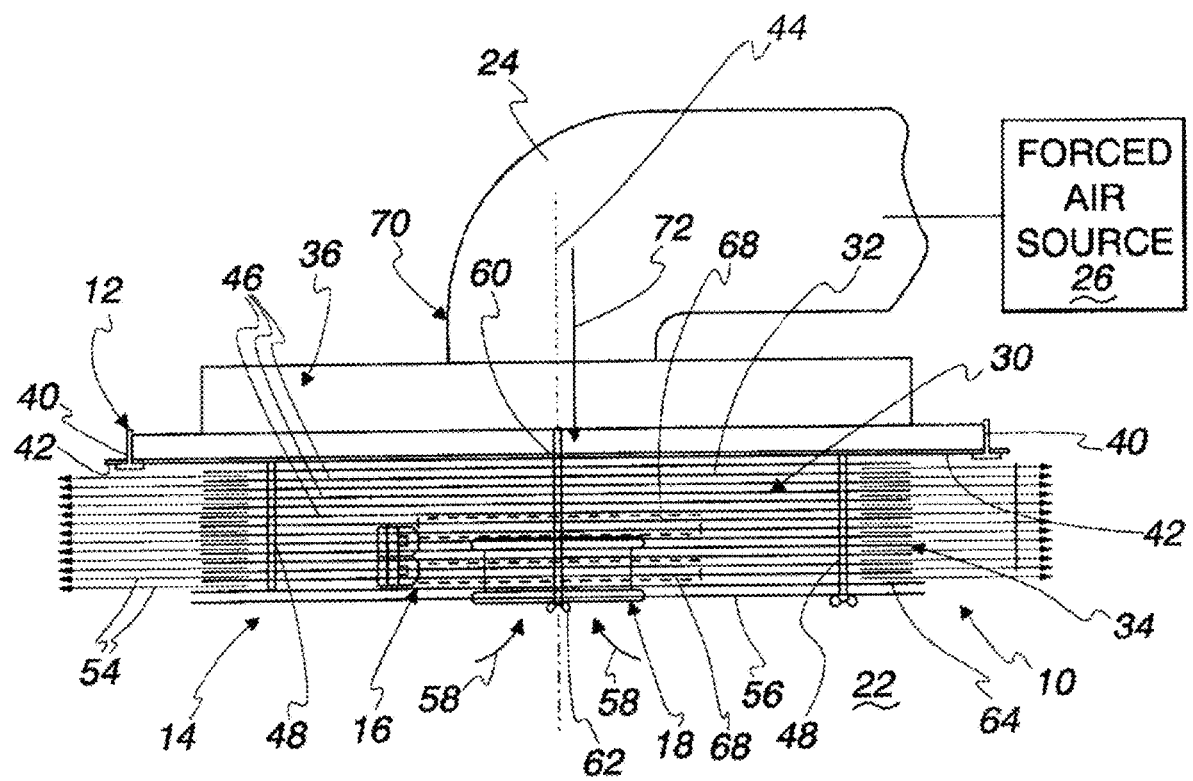
Figure 17E:
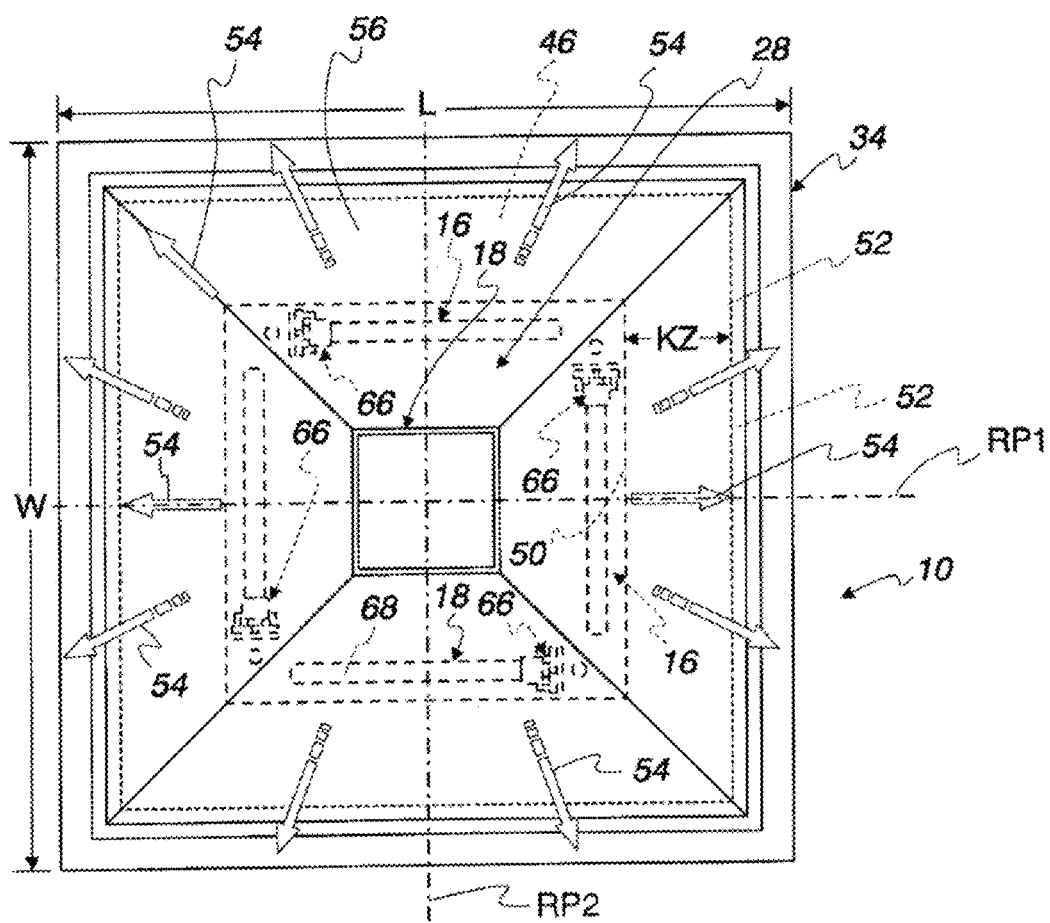

Ultraviolet-C light radiation reflective louvers 20 are assembled at the precise angles relative to base plate 34 as described above to enable the disinfection/sterilization field 30 or "kill zone" that is around the exterior of fixture 10. In contrast, the prior art reference, U.S. Pat. No. 10,753,626 (see FIGS. 17D and 17E). FIG. 17E depicts the disinfection/sterilization field or kill zone as "KZ" and clearly shows the kill zone within the air treatment unit 10. Further, the slats 46 and louvers 32 are positioned generally horizontal relative to the subframe 36. Still further, 14 very large louvers are required with the '626 patent adding further complexity and expense.

Figure 16:
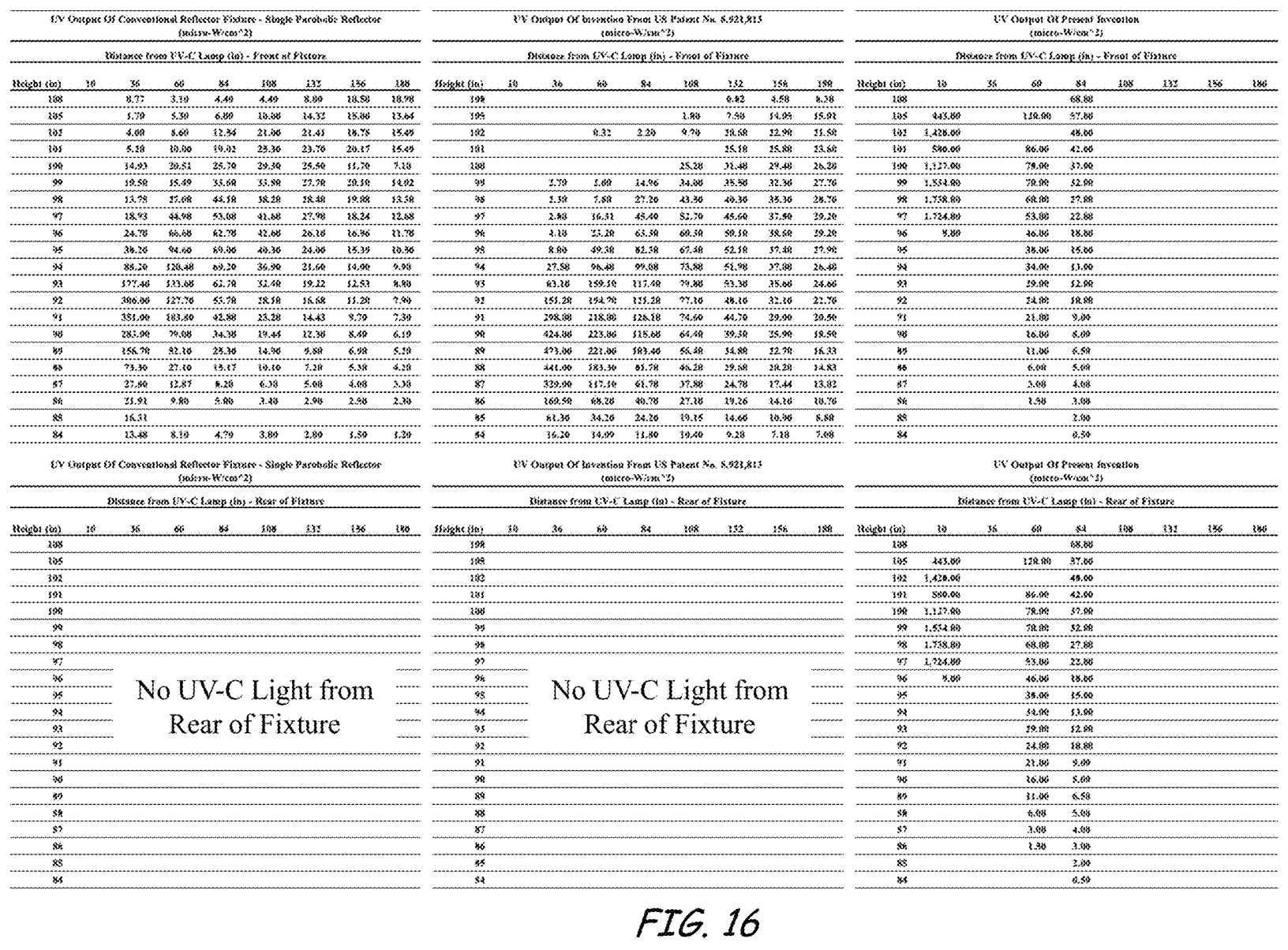

FIG. 16 is a table showing how the intensity of ultraviolet-C light radiation decreases for specific distances away from ultraviolet-C bulb 24. The table illustrates how fast the intensity of the ultraviolet-C light radiation decreases the further away from the ultraviolet-C bulb 24. Any absorption of the ultraviolet-C light radiation by any ultraviolet-C fixture will decrease the intensity of the radiation away from the lamp even further thus requiring more fixtures in a given area as dictated by the prior art. The table also indicates how important air flow through disinfection/sterilization chamber 118 and around bulb 26 is to adequately disinfect or sterilize the air. The present invention enables air flow to enter fixture 10 from both sides of fixture 10 thereby ensuring more air flow will enter disinfection/sterilization chamber 118 then any of the prior art that disclose wall mounted fixtures or fixtures having small gaps to allow airflow around the ultraviolet-C bulb. The present invention also limits the amount of ultraviolet-C light radiation being absorbed by the fixture 10 itself thus enabling a broader disinfection/sterilization field 30 around the exterior of fixture 10 than any of the prior art units. The present invention will enable more sterilization in a room having a given size with a lower number of fixtures and, therefore, less cost than any of the prior art units.

The present invention has been particularly shown and described with reference to the foregoing embodiments, which are merely illustrative of the best modes presently known for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method within the scope of these claims and their equivalents be covered thereby. This description of the invention should be understood to include all novel and non-obvious combination of elements described herein, and claims may be presented in this or a later application to any novel non-obvious combination of these elements. Moreover, the foregoing embodiments are illustrative, and no single feature or element is essential to all possible combinations that may be claimed in this or a later application.

What is claimed is:

1. An ultraviolet-C light radiation disinfection fixture comprising:
   a tray, said tray including:
      a base plate;
      at least one side wall, said at least one side wall is positioned at a ten degree outward angle relative to a perpendicular vertical that extends upward from said base plate; and
      at least one end plate;
   a top plate;
   at least one louver mount;
   at least one ultraviolet-C light radiation source to disinfect and sterilize an air flow;
   a sterilization field outside said ultraviolet-C light radiation disinfection fixture;
   a sterilization chamber within said ultraviolet-C light radiation disinfection fixture;
   a plurality of ultraviolet-C light radiation reflective louvers, said plurality of ultraviolet-C light radiation reflective louvers sized and positioned proximate one another, to direct ultraviolet-C light radiation from said ultraviolet-C light radiation source to the exterior of said ultraviolet-C light radiation disinfection fixture to create said sterilization field outside said ultraviolet-C light radiation disinfection fixture to eradicate bacterial, viral or pathogen particles from the air flow surrounding said ultraviolet-C light radiation disinfection fixture, said plurality of ultraviolet-C light radiation reflective louvers sized and positioned proximate one another to direct ultraviolet-C light radiation from said ultraviolet-C light radiation source in the interior of said ultraviolet-C light radiation disinfection fixture to create said sterilization chamber inside said ultraviolet-C light radiation disinfection fixture and said plurality of ultraviolet-C light radiation reflective louvers sized and positioned proximate one another to allow passage of the air flow containing a cloud of infectious bacterial, viral or pathogen particles to pass through said sterilization chamber within said ultraviolet-C light radiation disinfection fixture to eradicate bacterial, viral or pathogen particles from the air flow; and
   wherein said plurality of ultraviolet-C light radiation reflective louvers are positioned to limit the scatter of ultraviolet-C light radiation outside said ultraviolet-C light radiation disinfection fixture to protect humans and animals present in an enclosure while said ultraviolet-C light radiation disinfection fixture is operational.

2. The ultraviolet-C light radiation disinfection fixture as recited in claim 1, wherein said at least one side wall includes a wing, said wing is positioned at a four degree downward angle relative to said base plate.

3. The ultraviolet-C light radiation disinfection fixture as recited in claim 1, wherein said ultraviolet-C light radiation disinfection fixture includes a tube.

4. The ultraviolet-C light radiation disinfection fixture as recited in claim 1, wherein said ultraviolet-C light radiation disinfection fixture includes a bottom reflective arc.

5. The ultraviolet-C light radiation disinfection fixture as recited in claim 1, wherein said ultraviolet-C light radiation disinfection fixture includes a top reflective arc.

6. The ultraviolet-C light radiation disinfection fixture as recited in claim 1, wherein said ultraviolet-C light radiation disinfection fixture includes an absorption pad.

7. The ultraviolet-C light radiation disinfection fixture as recited in claim 1, wherein said ultraviolet-C light radiation disinfection fixture includes a dowel rod to secure said at least one louver mount to said ultraviolet light radiation disinfection fixture.

8. The ultraviolet-C light radiation disinfection fixture as recited in claim 1, wherein said plurality of ultraviolet-C light radiation reflective louvers include:
   a first ultraviolet-C light radiation reflective louver, said first ultraviolet-C light radiation reflective louver is positioned at a 26 degree upward angle relative to said base plate;
   a second ultraviolet-C light radiation reflective louver, said second ultraviolet-C light radiation reflective louver is positioned at a 23.5 degree upward angle relative to said base plate;
   a third ultraviolet-C light radiation reflective louver, said third ultraviolet-C light radiation reflective louver is positioned at a 20.5 degree upward angle relative to said base plate;
   a fourth ultraviolet-C light radiation reflective louver, said fourth ultraviolet-C light radiation reflective louver is positioned at an 18 degree upward angle relative to said base plate;
   a fifth ultraviolet-C light radiation reflective louver, said fifth ultraviolet-C light radiation reflective louver is positioned at a 15.5 degree upward angle relative to said base plate;
   a sixth ultraviolet-C light radiation reflective louver, said sixth ultraviolet-C light radiation reflective louver is positioned at a seven degree inward angle relative to a perpendicular vertical that extends upward from said base plate; and
   a seventh ultraviolet-C light radiation reflective louver, said seventh ultraviolet-C light radiation reflective louver is positioned at a 26 degree upward angle relative to said base plate.

9. The ultraviolet-C light radiation disinfection fixture as recited in claim 1, wherein said ultraviolet-C light radiation source operates at a wavelength of 200 nanometers to 280 nanometers.

10. The ultraviolet-C light radiation disinfection fixture as recited in claim 1, wherein said plurality of ultraviolet-C light radiation reflective louvers are positioned to ensure a maximum upward angle of reflection of ultraviolet-C light radiation at 14 degrees relative to base plate and a maximum downward angle of reflection of ultraviolet-C light radiation at 5 degrees relative to base plate to limit the scatter of ultraviolet-C light radiation outside said ultraviolet-C light radiation disinfection fixture.

11. The ultraviolet-C light radiation disinfection fixture as recited in claim 1, wherein said ultraviolet-C light radiation disinfection fixture includes at least one louver assembly.

\* \* \* \* \*